US009000018B2

(12) United States Patent
Binkert et al.

(10) Patent No.: US 9,000,018 B2
(45) Date of Patent: *Apr. 7, 2015

(54) THIAZOLIDIN-4-ONE-DERIVATIVES

(71) Applicant: Actelion Pharmaceuticals Ltd., Allschwil (CH)

(72) Inventors: Christoph Binkert, Basel (CH); Martin Bolli, Allschwil (CH); Boris Mathys, Egerkingen (CH); Claus Mueller, Weil am Rhein (CH); Michael Scherz, Ettingen (CH); Oliver Nayler, Arlesheim (CH)

(73) Assignee: Actelion Pharmaceuticals, Ltd, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/951,954

(22) Filed: Jul. 26, 2013

(65) Prior Publication Data

US 2013/0310432 A1    Nov. 21, 2013

Related U.S. Application Data

(60) Continuation of application No. 13/570,956, filed on Aug. 9, 2012, now Pat. No. 8,524,752, which is a division of application No. 12/496,945, filed on Jul. 2, 2009, now Pat. No. 8,273,779, which is a division of application No. 12/132,443, filed on Jun. 3, 2008, now Pat. No. 7,875,726, which is a division of application No. 10/580,169, filed on Dec. 1, 2006, now Pat. No. 7,435,828, which is a continuation-in-part of application No. PCT/EP2004/012953, filed on Nov. 16, 2004.

(30) Foreign Application Priority Data

Nov. 21, 2003 (WO) ................. PCT/EP2003/013072

(51) Int. Cl.
*A01N 43/78* (2006.01)
*A61K 31/425* (2006.01)
*C07D 277/00* (2006.01)
*C07D 277/54* (2006.01)
*A61K 31/426* (2006.01)
*C07D 277/20* (2006.01)
*C07D 277/42* (2006.01)
*C07D 417/06* (2006.01)

(52) U.S. Cl.
CPC ............ *C07D 277/54* (2013.01); *A61K 31/426* (2013.01); *C07D 277/20* (2013.01); *C07D 277/42* (2013.01); *C07D 417/06* (2013.01)

(58) Field of Classification Search
USPC .......................................... 514/369; 548/184
See application file for complete search history.

(56) References Cited

U.S. PATENT DOCUMENTS

| | | | |
|---|---|---|---|
| 3,077,402 A | 2/1963 | Blout et al. | |
| 3,175,905 A | 3/1965 | Stahlhofen | |
| 3,759,938 A | 9/1973 | Giraudon | |
| 5,422,360 A | 6/1995 | Miyajima et al. | |
| 5,677,322 A | 10/1997 | Yasumura et al. | |
| 6,353,006 B1 | 3/2002 | Dixon et al. | |
| 6,380,229 B1 | 4/2002 | Yoneda et al. | |
| 7,435,828 B2 | 10/2008 | Binkert et al. | |
| 7,626,037 B2 | 12/2009 | Binkert et al. | |
| 7,767,701 B2 | 8/2010 | Hasegawa et al. | |
| 7,875,726 B2 | 1/2011 | Binkert et al. | |
| 8,263,780 B2 | 9/2012 | Abele et al. | |
| 8,273,779 B2 | 9/2012 | Binkert et al. | |
| RE43,728 E | 10/2012 | Binkert et al. | |
| RE43,833 E | 11/2012 | Binkert et al. | |
| 8,524,752 B2 | 9/2013 | Binkert et al. | |
| 2004/0009527 A1 | 1/2004 | Dong et al. | |
| 2004/0167192 A1 | 8/2004 | Solow-Cordero et al. | |
| 2005/0019825 A9 | 1/2005 | Dong et al. | |
| 2005/0096364 A1 | 5/2005 | Romine et al. | |
| 2007/0249599 A1 | 10/2007 | Duffy et al. | |
| 2011/0021581 A1 | 1/2011 | Brossard et al. | |
| 2011/0196004 A1 | 8/2011 | Bonham et al. | |
| 2012/0302758 A1 | 11/2012 | Abele et al. | |

FOREIGN PATENT DOCUMENTS

| | | |
|---|---|---|
| EP | 1219612 | 7/2002 |
| GB | 999796 | 7/1965 |
| WO | WO 91/17151 | 11/1991 |
| WO | WO 96/20936 | 7/1996 |
| WO | WO 2004/007491 | 1/2004 |
| WO | WO 2004/010987 | 2/2004 |
| WO | WO 2005/054215 | 6/2005 |
| WO | WO 2006/094233 | 9/2006 |

OTHER PUBLICATIONS

Ellis et. al., The New England Journal of Medicine, 2001, Massachusetts Medical Society, vol. 345, No. 4, pp. 248-255.*
Anonymous, "Actelion's Orally Active Selective S1P1 Receptor Agonist to be Jointly Developed/Promoted with Roche in Autoimmune Disorders and Transplantation Deal Potentially Worth Well Over US $630 Million to Actelion", Muscoskeletal Report, [Online], Jul. 20, 2006, pp. 1, New York, NY 10016, USA, Retrieved from the Internet: URL: http://www.mscreport.com/print.cfm?articleID=827>.
Bailar et al.; The New England Journal of Medicine; 1997; Massachusetts Medical Society, vol. 336, Issue 22, pp. 1569-1574.
Baker; Journal of Applied Physiology; 2002; American Physiological Society; vol. 92; pp. 1779-1780.
Beger et al; World Journal of Surgery; 2003; Societe Internationale de Chirugie; vol. 27; pp. 1075-1084.
Berge et al; "Pharmaceutical Salts"; Journal of Pharmaceutical Sciences; vol. 66, No. 1; 1977; pp. 1-19.
Braun-Moscovici et al; Current Opinion in Rheumatology; 2002; Lippincott Williams and Wilkins; vol. 14; pp. 711-716.

(Continued)

*Primary Examiner* — Sarah Pihonak
(74) *Attorney, Agent, or Firm* — Hoxie & Associates, LLC

(57) ABSTRACT

The invention relates to pharmaceutical compositions containing at least one thiazolidin-4-one derivative to prevent or treat disorders associated with an activated immune system. Furthermore, the invention relates to novel thiazolidin-4-one derivatives notably for use as pharmaceutically active compounds. Said compounds particularly act also as immunosuppressive agents.

21 Claims, No Drawings

(56) References Cited

OTHER PUBLICATIONS

Bunemann et al; "Activation of Muscarinic K+ Current in Guinea-Pig Atrial Myocytes by Sphingosine-1 phosphate", Journal of Physiology, vol. 489, pp. 701-707, (1995).

Carter et al; "Photochemically enhanced Binding of Samll Molecules to the Tumor Necrosis Factor Receptor-1 Inhibits the binding of TNF-alpha"; PNAS. vol. 98, No. 21, Oct. 9, 2001; pp. 11879-11884.

Davidov et al; "Chronic Nitric Oxide Synthase Blockade Desensitizes the Heart to the Negative Metabolic Effects of Nitric Oxide", Life Sciences, Pergamon Press, Oxford, GB, vol. 79, pp. 1674-1680, (2006).

Ehrlenmeyer et al; "Structural Chemical Investigations. VII. Reactive Behavior of Thiourea to Unsaturated Acids"; CA 37:10142, 1943.

Frolkis et al; "The Role of 'Invertors' (Intracellular Activators) in Age-related Changes in Cell Response to Hormones", Experimental Gerontology, vol. 30, pp. 401-414, (1995).

Fujishiro et al; "Use of Sphingosine-1-Phosphate 1 Receptor Agonist, KRP-203, in Combination with a Subtherapeutic Dose of Cyclosporine A for Rat Renal Transplantation", Transplantation, vol. 82(6), pp. 804-812, (2006).

Gibson; "Pharmaceutical Preformulation of Formulation"; HIS Health Group, Englewood, CO, USA 2001; Table of Contents.

Giese et al; Journal of Cancer Research and Clinical Oncology; 2001; Springer-Verlag; vol. 127, pp. 217-225.

Gould et al; "Salt Selections for Basic Drugs"; Int. J. Pharm.; vol. 33; 1986; pp. 201-217.

Guo et al; "Effects of Sphingosine 1-phosphate on Pacemaker Activity in Rabbit Sino-atrial Node Cells", Pflugers Arch, vol. 438, pp. 642-648, (1999).

Hale et al; "Selecting Against S1P3 Enhances the Acute Cardiovascular Tolerability of 3-(N-benzyl)aminopropylphosphonic Acid S1P Receptor Agonists", Bioorganic & Medicinal Chemistry Letters, vol. 14(13), pp. 3501-3505, (2004).

Himmel et al; "Evidence for Edg-3 Receptor-Mediated Activation of IK.Ach by Sphingosine-1-Phosphate in Human Atrial Cardiomyocytes", Molecular Pharmacology, vol. 58, pp. 449-454, (2000).

Huwiler et al; "New Players on the Center Stage: Sphingosine 1-Phosphate and its Receptors as Drug Targets", Biochemical Pharmacology, Pergamon Press, Oxford, GB, vol. 75, pp. 1893-1900, (2008).

Janusz et al; "New Cyclooxygenase-2/5-Lipoxyfenase Inhibitors, 3, 7-tert-Butyl-2,3-dihydro-3, 3-dimethylbenzofuran Derivatives as Gastrointestinal Safe Antiinflammatory and Analgesic Agents: Variations at the 5 Position"; J. Medicinal Chemistry, vol. 41, 1998, pp. 3515-3529.

Kappos et al; "Oral Fingolimod (FTY720) for Relapsing Multiple Sclerosis", The New England Journal of Medicine, vol. 355(11), pp. 1124-1140, (2006).

Klika et al; "Regioselective Synthesis of 2-imino-1,3-thiazolidin-4-ones by Treatment of N-(Anthracen-9-yl)-N9-ehylthiourea [ . . . ]" Eur. J. Org. Chem. 2002, pp. 1248-1255.

Kovarik et al; "A Mechanistic Study to Assess Whether Isoproterenol Can Reverse the Negative Chronotropic Effect of Fingolimod", Journal of Clinical Pharmacology, vol. 48, No. 3, pp. 303-310 (2008).

Koyrakh et al; "The Heart Rate Decrease Caused by Acute FTY720 Administration is Mediated by the G Protein-Gated Potassium Channel IKACh", American Journal of Transplantation, vol. 5, pp. 529-536, (2005).

Ma; "High-Affinity Activators of Cystic Fibrosis Transmembrance Conductance Regulator (CFTR) Chloride Conductance Identified by High-Throughout Screening"; The Journal of Biological Chemistry, vol. 277, No. 40, Issue of Oct. 4, pp. 37235-37241; [2002].

Martinet et al; Journal of the National Cancer Institute; 2000; National Cancer Institute; vol. 92; No. 11; pp. 931-936.

Non-Final Office Action dated Feb. 1. 2011, U.S. Appl. No. 12/516,055.

Ochi et al; "Sphingosine-1-Phosphate Effects on Guinea Pig Atrial Myocytes: Alterations in Action Potentials and K+ Currents", Cardiovascular Research, vol. 70, pp. 88-96, (2006).

Ottana et al; 5-Arylidene-2-imino-4-thiazolidinones: Design and Synthesis of Novel Anti-Inflammatory Agents, Biorganic and Medicinal Chemistry, 13(13) (2005) pp. 4243-4252.

Peters et al; "Sphingosine-1-Phosphate Signaling in the Cardiovascular System", Current Opinion in Pharmacology, vol. 7(2), pp. 156-192, (2007).

Remington; "The Science and Practice of Pharmacy"; 20th Edition; Philadelphia College of Pharmacy and Science; 2003; Table of Contents.

Sanna et al; "Sphingosine 1-Phosphate (S1P) Receptor Subtypes S1P1 and S1P3, Respectively, Regulate Lymphocyte Recirculation and Heart Rate", The Journal of Biological Chemistry, vol. 279(14), pp. 13839-13848, (2004).

Smith et al; Annals of Neurology; 2003; American Neurological Association; vol. 54; pp. 186-196.

Surh; Nature Reviews Cancer; 2003; Nature Publishing Group; vol. 3; pp. 763-780.

Notices of Allowance dated Jul. 21, 2011, Nov. 15, 2011 and May 3, 2012, U.S. Appl. No. 12/516,055.

Ottana et al; 5-Arylidene-2-imino-4-thiazolidinones: Design and Synthesis of Novel Anti-Inflammatory Agents, Bioorganic and Medicinal Chemistry, 13(13) (2005) pp. 4243-4252. (available online May 17, 2005).

U.S. Appl. No. 14/028,712, filed Sep. 17, 2013, Binkert et al.

* cited by examiner

THIAZOLIDIN-4-ONE-DERIVATIVES

CROSS REFERENCE TO RELATED APPLICATIONS

This application is a continuation of U.S. application Ser. No. 13/570,956, filed Aug. 9, 2012, which is a divisional of U.S. application Ser. No. 12/496,945, filed Jul. 2, 2009, now U.S. Pat. No. 8,273,779, which is a divisional of U.S. application Ser. No. 12/132,443, filed on Jun. 3, 2008, now U.S. Pat. No. 7,875,726, which is a divisional of U.S. application Ser. No. 10/580,169, filed on Dec. 1, 2006 (issued as U.S. Pat. No. 7,435,828, now U.S. Pat. No. RE 43,728), which is a continuation-in-part of Application of PCT/EP2004/012953, filed Nov. 16, 2004, which claims priority to PCT/EP03/13072, filed on Nov. 21, 2003, the contents of each of which are incorporated herein by reference in their entirety.

FIELD OF THE INVENTION

The present invention relates to novel thiazolidin-4-one derivatives of the General Formula (I) and their use as active ingredients in the preparation of pharmaceutical compositions. The invention also concerns related aspects including processes for the preparation of the compounds, pharmaceutical compositions containing one or more compounds of the General Formula (I), and their use as immunosuppressant agents, either alone or in combination with other immunosuppressant therapies.

BACKGROUND OF THE INVENTION

The immune system attempts to fight a transplanted organ in the same way it fights an infection or a cancer. Without immunosuppressive medication to inhibit the immune system's action, a transplanted organ is quickly rejected and stops functioning. Organ transplant recipients can experience some organ rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathiopirene or leflunomide, which inhibit nucleotide synthesis; or 15-deoxyspergualin, an inhibitor of leukocyte differentiation. The beneficial effects of these therapies relate to their broad immunosuppressive effects; however, the generalized immunosuppression which these drugs produce also diminishes the immune system's defense against infection and malignancies. Furthermore, standard immunosuppressive drugs are often used at high dosages and can themselves cause or accelerate organ damage in either the transplanted organ itself, or in other target organs of the transplant recipient.

DESCRIPTION OF THE INVENTION

The present invention provides compounds having a powerful and long-lasting immunosuppressive effect which is achieved by reducing the number of circulating and infiltrating T- and B-lymphocytes, without affecting their maturation, memory, or expansion. In consequence, the compounds of the present invention can be utilized alone or in combination with standard T-cell activation inhibiting drugs, to provide a new immunosuppressive therapy with a reduced propensity for infections or malignancies when compared to standard immunosuppressive therapy. Furthermore, the compounds of the present invention can be used in combination with reduced dosages of traditional immunosuppressant therapies, to provide on the one hand effective immunosuppressive activity, while on the other hand reducing end organ damage associated with higher doses of standard immunosuppressive drugs.

Biological Assay

The immunosuppressive activity of the compounds of the invention can be demonstrated by measuring the number of circulating lymphocytes in whole blood of rats as follows.

Normotensive male Wistar rats are housed in climate-controlled conditions with a 12-hour light/dark cycle, and have free access to normal rat chow and drinking water. Blood (0.5 mL) is collected by retro-orbital sampling before drug administration, and 3 and 6 h thereafter. Blood cell count is measured in whole blood using a Beckman-Coulter Synchron CX5 Pro cytometer. Statistical analysis of lymphocyte counts are performed by analysis of variance (ANOVA) using Statistica (StatSoft) and the Student-Newman-Keuls procedure for multiple comparisons.

Thus, compounds of the invention decrease the number of circulating lymphocytes in whole blood when compared to pre-drug values.

Table 1 shows the effect on lymphocyte counts 6 h after oral administration of 10 mg/kg of a compound of the present invention to normotensive male Wistar rats as compared to a group of animals treated with vehicle only.

TABLE 1

| Compound of Example | Lymphocyte counts [%] |
| --- | --- |
| 4 | −32 |
| 7 | −67 |
| 24 | −54 |
| 42 | −23 |
| 46 | −37 |
| 75 | −47 |
| 76 | −58 |
| 77 | −55 |
| 84 | −68 |
| 85 | −63 |
| 86 | −30* |
| 91 | −35 |
| 95 | −53 |
| 100 | −53 |
| 103 | −47 |
| 110 | −30 |
| 130 | −26 |

*at 3 mg/kg p.o.

The following paragraphs provide definitions of the various chemical moieties that make up the compounds according to the invention and are intended to apply uniformly throughout the specification and claims unless an otherwise expressly set out definition provides a broader definition.

The term lower alkyl, alone or in combination with other groups, means saturated, straight or branched chain groups with one to seven carbon atoms, preferably one to four carbon atoms. Examples of lower alkyl groups are methyl, ethyl, n-propyl, iso-propyl, n-butyl, iso-butyl, sec-butyl, tert-butyl, n-pentyl, n-hexyl or n-heptyl.

The term lower alkoxy means a R—O group, wherein R is a lower alkyl. Preferred examples of lower alkoxy groups are methoxy, ethoxy, propoxy, iso-propoxy, iso-butoxy, sec-butoxy or tert-butoxy.

The term mono- or di-lower alkylamino means a R'—NH— or a R'—NR"— group, wherein R' and R" are each independently a lower alkyl. Preferred examples of mono- or di-lower alkylamino groups are methylamino, ethylamino, N,N-dimethylamino, or N-methyl-N-ethyl-amino.

The term lower alkenyl, alone or in combination with other groups, means straight or branched chain groups comprising an olefinic bond and three to seven carbon atoms, preferably three to five carbon atoms. Examples of lower alkenyl are allyl, (E)-but-2-enyl, (Z)-but-2-enyl, or but-3-enyl.

The term halogen means fluoro, chloro, bromo or iodo.

The term cycloalkyl alone or in combination, means a saturated cyclic hydrocarbon ring system with 3 to 7 carbon atoms, preferably three to six carbon atoms. Examples of cycloalkyl are cyclopropyl, cyclobutyl, cyclopentyl, cyclohexyl or cycloheptyl.

The expression pharmaceutically acceptable salts encompasses either salts with inorganic acids or organic acids like hydrochloric or hydrobromic acid, sulfuric acid, phosphoric acid, citric acid, formic acid, acetic acid, maleic acid, tartaric acid, benzoic acid, methanesulfonic acid, and the like that are non-toxic to living organisms. In case the compound of General Formula (I) or General Formula (II) is acidic in nature the expression encompasses salts with an inorganic base like an alkali or earth alkali base, e.g. sodium hydroxide, potassium hydroxide, calcium hydroxide, or with an organic base such as benzathine, choline, meglumine, and the like which are also non-toxic to living organisms (S. M. Berge, L. D. Bighley and D. C. Monkhouse, Pharmaceutical salts, *J. Pharm. Sci.*, 66 (1977), 1-19; P. L. Gould, Salt selection of basic drugs, *Int. J. Pharmaceutics* 33 (1986), 201-217).

The compounds of the General Formula (I) and General Formula (II) can contain one or more asymmetric carbon atoms and may be prepared in form of optically pure enantiomers, mixtures of enantiomers such as racemates, diastereomers, mixtures of diastereomers, diastereomeric racemates, mixtures of diastereomeric racemates, and meso-forms. The present invention encompasses all these forms.

A first aspect of the invention consists of a novel pharmaceutical composition comprising at least one thiazolidin-4-one derivative of the General Formula (I):

General Formula (I)

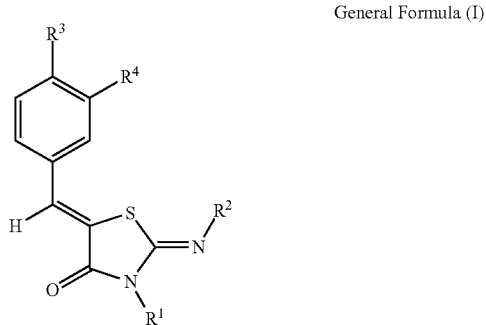

wherein:
$R^1$ represents lower alkyl, lower alkenyl; cycloalkyl; 5,6,7,8-tetrahydronaphth-1-yl; 5,6,7,8-tetrahydronaphth-2-yl; a phenyl group; a phenyl group independently mono-, di- or trisubstituted with lower alkyl, halogen, lower alkoxy, or —$CF_3$;

$R^2$ represents lower alkyl; allyl; cyclopropyl; cyclobutyl; cyclopentyl; mono- or di-lower alkylamino;

$R^3$ represents —$NR^5R^6$; —O—$CR^7R^8$—$CR^9R^{10}$—$(CR^{11}R^{12})_n$—O—$R^{13}$;

$R^4$ represents hydrogen; hydroxy; lower alkoxy; lower alkyl; halogen; or $R^3$ and $R^4$ together may form a methylenedioxy or ethylenedioxy ring optionally further substituted with a hydroxy methyl group;

$R^5$ and $R^6$ each represents independently lower alkyl;

$R^7$ represents hydrogen, lower alkyl, or hydroxymethyl;

$R^8$, $R^9$, $R^{11}$ and $R^{12}$ each represents independently hydrogen or methyl;

$R^{10}$ represents hydrogen or lower alkyl; in case n represents the integer 1, $R^{10}$ in addition represents lower alkoxy, hydroxy, —$NH_2$, —$NHR^5$ or —$NR^5R^6$;

$R^{13}$ represents hydrogen; lower alkyl; hydroxycarbonyl-lower alkyl; 1-glyceryl or 2-glyceryl;

n represents the integer 0 or 1;

and configurational isomers, optically pure enantiomers, mixtures of enantiomers such as racemates, diastereomers, mixtures of diastereomers, diastereomeric racemates, mixtures of diastereomeric racemates and the meso-form, as well as pharmaceutically acceptable salts, solvent complexes, and morphological forms, and inert carrier material.

The compounds of General Formula (I) and their pharmaceutically acceptable salts can be used as medicaments, e.g. in the form of pharmaceutical preparations for enteral, parental or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, cream or oils.

The production of the pharmaceutical preparations can be effected in a manner which will be familiar to any person skilled in the art (see for example Mark Gibson, Editor, Pharmaceutical Preformulation and Formulation, IHS Health Group, Englewood, Colo., USA, 2001; Remington, The Science and Practice of Pharmacy, 20th Edition, Philadelphia College of Pharmacy and Science) by bringing the described compounds of General Formula (I) and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable inert carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of General Formula (I) can vary within wide limits depending on the disease to be controlled, the age and the individual condition of the patient and the mode of administration, and will, of course, be fitted to the individual requirements in each particular case. For adult patients a daily dosage of about 0.5 mg to about 1000 mg, especially about 1 mg to about 500 mg, comes into consideration for the treatment of disorders associated with an activated immune system for adult patients. Depending on the dosage it may be convenient to administer the daily dosage in several dosage units.

The pharmaceutical preparations conveniently contain about 0.5 to 500 mg, preferably 1 to 250 mg, of a compound of General Formula (I).

In a preferred embodiment according to the invention, the above-mentioned pharmaceutical composition comprises the (Z,Z)-isomers of the thiazolidin-4-one derivatives of the General Formula (I).

The above-mentioned pharmaceutical composition is useful for the prevention and treatment of disorders associated with an activated immune system.

Such diseases or disorders are selected from the group consisting of rejection of transplanted organs or tissue; graft-versus-host diseases brought about by transplantation; autoimmune syndromes including rheumatoid arthritis; systemic lupus erythematosus; Hashimoto's thyroiditis; lymphocytic thyroiditis; multiple sclerosis; myasthenia gravis; type I diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; coeliac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; psoriasis; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure.

Particularly preferred diseases comprise the group consisting of rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; post-infectious autoimmune diseases including rheumatic fever and post-infectious glomerulonephritis; and metastasis of carcinoma.

Furthermore, compounds of the General Formula (I) are also useful, in combination with one or several immunosuppressant agents, for the treatment of disorders associated with an activated immune system and selected from the list as above-mentioned. According to a preferred embodiment of the invention, said immunosuppressant agent is selected from the group comprising or consisting of cyclosporin, daclizumab, basiliximab, everolimus, tacrolimus (FK506), azathiopirene, leflunomide, 15-deoxyspergualin, or other immunosuppressant drugs.

Another aspect of the invention concerns a method for the prevention or treatment of disorders associated with an activated immune system comprising the administration to the patient of a pharmaceutical composition containing a compound of the General Formula (I). A suitable dose of the compound of General Formula (I) in the pharmaceutical composition is between 0.5 mg and 1000 mg per day. In a preferred embodiment of the invention, said dose is comprised between 1 mg and 500 mg per day and more particularly between 5 mg and 200 mg per day.

A further aspect of the invention are novel thiazolidin-4-one derivatives of the following General Formula (II):

General Formula (II)

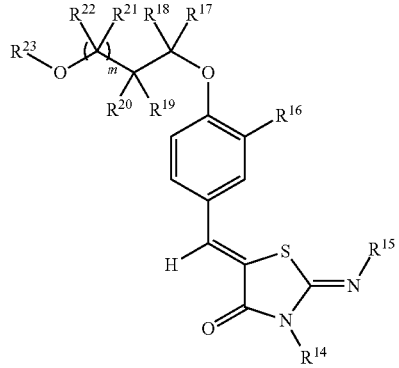

wherein:
$R^{14}$ represents lower alkyl, lower alkenyl; cycloalkyl; 5,6,7,8-tetrahydronaphth-1-yl; 5,6,7,8-tetrahydronaphth-2-yl; a phenyl group; a phenyl group mono-, di- or trisubstituted independently with lower alkyl, halogen, lower alkoxy, or —CF$_3$;

$R^{15}$ represents lower alkyl; allyl; cyclopropyl; cyclobutyl; cyclopentyl; mono- or di-lower alkylamino;

$R^{16}$ represents hydrogen; hydroxy; lower alkoxy; lower alkyl or halogen;

$R^{17}$ represents hydrogen, lower alkyl, or hydroxymethyl;

$R^{18}$, $R^{19}$, $R^{21}$ and $R^{22}$ each represents independently hydrogen or methyl;

$R^{20}$ represents hydrogen or lower alkyl; and in case m represents the integer 1, $R^{20}$ in addition represents lower alkoxy, hydroxy, —NH$_2$, —NHR$^5$ or —NR$^5$R$^6$;

$R^{23}$ represents hydrogen; lower alkyl; hydroxycarbonyl-lower alkyl; 1-glyceryl or 2-glyceryl;

m represents the integer 0 or 1;

and configurational isomers, optically pure enantiomers, mixtures of enantiomers such as racemates, diastereomers, mixtures of diastereomers, diastereomeric racemates, mixtures of diastereomeric racemates and the meso-form, as well as pharmaceutically acceptable salts.

Preferred thiazolidin-4-one derivatives according to General Formula (II) are (Z,Z) isomers of General Formula (II).

In a preferred embodiment, $R^{14}$ represents an unsubstituted, a mono- or disubstituted phenyl group.

In another preferred embodiment, $R^{14}$ represents an unsubstituted, a mono- or disubstituted phenyl group, substituted with methyl or halogen.

In a further preferred embodiment, $R^{15}$ represents lower alkyl.

In another preferred embodiment, $R^{16}$ represents halogen or methyl.

In another preferred embodiment, m represents the integer 0; and $R^{17}$, $R^{18}$, $R^{19}$, and $R^{20}$ represent hydrogen.

In yet another preferred embodiment, m represents the integer 1, $R^{17}$, $R^{18}$, $R^{19}$, $R^{21}$, $R^{22}$ represent hydrogen, and $R^{20}$ represents hydroxy.

In a particularly preferred embodiment, $R^{23}$ represents hydrogen.

In another particularly preferred embodiment, m represents the integer 0; $R^{17}$, $R^{18}$, $R^{19}$, $R^{20}$, and $R^{23}$ represents hydrogen.

In another particularly preferred embodiment, m represents the integer 1, $R^{17}$, $R^{18}$, $R^{19}$, $R^{21}$, $R^{22}$, and $R^{23}$ represent hydrogen, and $R^{20}$ represents hydroxy.

In a further preferred embodiment, $R^{14}$ represents an unsubstituted, a mono- or disubstituted phenyl group, substituted with methyl or halogen, and $R^{15}$ represents lower alkyl.

In another further preferred embodiment, $R^{14}$ represents an unsubstituted, a mono- or disubstituted phenyl group, substituted with methyl or halogen, m represents the integer 0; $R^{17}$, $R^{18}$, $R^{19}$, $R^{20}$, and $R^{23}$ represents hydrogen.

In another further preferred embodiment, $R^{14}$ represents an unsubstituted, a mono- or disubstituted phenyl group, substituted with methyl or halogen, m represents the integer 1, $R^{17}$, $R^{18}$, $R^{19}$, $R^{21}$, $R^{22}$, and $R^{23}$ represent hydrogen, and $R^{20}$ represents hydroxy.

In particularly preferred embodiment, $R^{14}$ represents an unsubstituted, a mono- or disubstituted phenyl group, substituted with methyl or halogen, $R^{15}$ represents lower alkyl; $R^{16}$ represents halogen or methyl, m represents the integer 0, and $R^{17}$, $R^{18}$, $R^{19}$, $R^{20}$ and $R^{23}$ each represent hydrogen.

In another particularly preferred embodiment, $R^{14}$ represents an unsubstituted, a mono- or disubstituted phenyl group, substituted with methyl or halogen, $R^{15}$ represents lower alkyl; $R^{16}$ represents halogen or methyl, m represents the integer 1, $R^{17}$, $R^{18}$, $R^{19}$, $R^{21}$, $R^{22}$, and $R^{23}$ represent hydrogen, and $R^{20}$ represents hydroxy.

Specific thiazolidin-4-one derivatives according to formula (II) are:
- 5-[4-(2-hydroxy-ethoxy)-benz[Z]ylidene]-2-([Z]-isopropylimino)-3-phenyl-thiazolidin-4-one,
- {2-[4-(2-([Z]-isopropylimino)-4-oxo-3-phenyl-thiazolidin-5-[Z]-ylidenemethyl)-phenoxy]-ethoxy}-acetic acid,
- rac-5-{4-[2-(2,3-dihydroxy-propoxy)-ethoxy]-benz[Z]ylidene}-2-([Z]-isopropylimino)-3-phenyl-thiazolidin-4-one,
- 5-[3-chloro-4-(2-hydroxy-ethoxy)-benz[Z]ylidene]-2-([Z]-isopropylimino)-3-phenyl-thiazolidin-4-one,
- 5-[3-fluoro-4-(2-hydroxy-ethoxy)-benz[Z]ylidene]-2-([Z]-isopropylimino)-3-phenyl-thiazolidin-4-one,
- 5-[4-(2-hydroxy-ethoxy)-3-methyl-benz[Z]ylidene]-2-([Z]-isopropylimino)-3-phenyl-thiazolidin-4-one,
- 5-[4-(2-hydroxy-ethoxy)-3-methoxy-benz[Z]ylidene]-2-([Z]-isopropylimino)-3-phenyl-thiazolidin-4-one,
- 5-[4-(3-hydroxy-propoxy)-benz[Z]ylidene]-2-([Z]-isopropylimino)-3-phenyl-thiazolidin-4-one,
- rac-5-[4-(2,3-dihydroxy-propoxy)-benz[Z]ylidene]-2-([Z]-isopropylimino)-3-phenyl-thiazolidin-4-one,
- rac-5-[3-chloro-4-(2,3-dihydroxy-propoxy)-benz[Z]ylidene]-2-([Z]-isopropylimino)-3-phenyl-thiazolidin-4-one,
- 5-[4-(2-hydroxy-ethoxy)-benz[Z]ylidene]-2-([Z]-isopropylimino)-3-o-tolyl-thiazolidin-4-one,
- rac-5-{4-[2-(2,3-dihydroxy-propoxy)-ethoxy]-benz[Z]ylidene}-2-([Z]-isopropylimino)-3-o-tolyl-thiazolidin-4-one,
- 5-[3-chloro-4-(2-hydroxy-ethoxy)-benz[Z]ylidene]-2-([Z]-isopropylimino)-3-o-tolyl-thiazolidin-4-one,
- 5-[3-chloro-4-(2-hydroxy-ethoxy)-benz[Z]ylidene]-2-([Z]-isopropylimino)-3-o-tolyl-thiazolidin-4-one,
- 5-[4-(2-hydroxy-ethoxy)-3-methoxy-benz[Z]ylidene]-2-([Z]-isopropylimino)-3-o-tolyl-thiazolidin-4-one,
- 5-[4-(3-hydroxy-propoxy)-benz[Z]ylidene]-2-([Z]-isopropylimino)-3-o-tolyl-thiazolidin-4-one,
- rac-5-[3-chloro-4-(2,3-dihydroxy-propoxy)-benz[Z]ylidene]-2-([Z]-isopropylimino)-3-o-tolyl-thiazolidin-4-one,
- 5-[4-(2-hydroxy-ethoxy)-benz[Z]ylidene]-2-([Z]-isopropylimino)-3-m-tolyl-thiazolidin-4-one,
- 5-[3-chloro-4-(2-hydroxy-ethoxy)-benz[Z]ylidene]-2-([Z]-isopropylimino)-3-m-tolyl-thiazolidin-4-one,
- rac-5-[3-chloro-4-(2,3-dihydroxy-propoxy)-benz[Z]ylidene]-2-([Z]-isopropylimino)-3-m-tolyl-thiazolidin-4-one,
- 5-[4-(2-hydroxy-ethoxy)-benz[Z]ylidene]-2-([Z]-isopropylimino)-3-p-tolyl-thiazolidin-4-one,
- 5-[3-chloro-4-(2-hydroxy-ethoxy)-benz[Z]ylidene]-2-([Z]-isopropylimino)-3-p-tolyl-thiazolidin-4-one,
- rac-5-[3-chloro-4-(2,3-dihydroxy-propoxy)-benz[Z]ylidene]-2-([Z]-isopropylimino)-3-p-tolyl-thiazolidin-4-one,
- 3-(2,3-dimethyl-phenyl)-5-[4-(2-hydroxy-ethoxy)-benz[Z]ylidene]-2-([Z]-isopropylimino)-thiazolidin-4-one,
- rac-5-{4-[2-(2,3-dihydroxy-propoxy)-ethoxy]-benz[Z]ylidene}-3-(2,3-dimethyl-phenyl)-2-([Z]-isopropylimino)-thiazolidin-4-one,
- 5-[3-chloro-4-(2-hydroxy-ethoxy)-benz[Z]ylidene]-3-(2,3-dimethyl-phenyl)-2-([Z]-isopropylimino)-thiazolidin-4-one, 3-(2,3-dimethyl-phenyl)-5-[3-fluoro-4-(2-hydroxy-ethoxy)-benz[Z]ylidene]-2-([Z]-isopropylimino)-thiazolidin-4-one,
3-(2,3-dimethyl-phenyl)-5-[4-(2-hydroxy-ethoxy)-3-methyl-benz[Z]ylidene]-2-([Z]-isopropylimino)-thiazolidin-4-one,
3-(2,3-dimethyl-phenyl)-5-[4-(2-hydroxy-ethoxy)-3-methoxy-benz[Z]ylidene]-2-([Z]-isopropylimino)-thiazolidin-4-one,
rac-5-[3-chloro-4-(2,3-dihydroxy-propoxy)-benz[Z]ylidene]-3-(2,3-dimethyl-phenyl)-2-([Z]-isopropylimino)-thiazolidin-4-one,
3-(2,4-dimethyl-phenyl)-5-[4-(2-hydroxy-ethoxy)-benz[Z]ylidene]-2-([Z]-isopropylimino)-thiazolidin-4-one,
5-(2,3-dihydro-benzo[1,4]dioxin-6-[Z]-ylmethylene)-3-(2,6-dimethyl-phenyl)-2-([Z]-isopropylimino)-thiazolidin-4-one,
3-(2,6-dimethyl-phenyl)-5-[4-(2-hydroxy-ethoxy)-benz[Z]ylidene]-2-([Z]-isopropylimino)-thiazolidin-4-one,
3-(2-chloro-phenyl)-5-[4-(2-hydroxy-ethoxy)-benz[Z]ylidene]-2-([Z]-isopropylimino)-thiazolidin-4-one,
5-[3-chloro-4-(2-hydroxy-ethoxy)-benz[Z]ylidene]-3-(2-chloro-phenyl)-2-([Z]-isopropylimino)-thiazolidin-4-one,
5-[3-chloro-4-(2,3-dihydroxy-propoxy)-benz[Z]ylidene]-3-(2-chloro-phenyl)-2-([Z]-isopropylimino)-thiazolidin-4-one,
5-[4-(2-hydroxy-ethoxy)-benz[Z]ylidene]-2-([Z]-isopropylimino)-3-(2-methoxy-phenyl)-thiazolidin-4-one,
5-[3-chloro-4-(2-hydroxy-ethoxy)-benz[Z]ylidene]-2-([Z]-isopropylimino)-3-(2-methoxy-phenyl)-thiazolidin-4-one,
5-(2,3-dihydro-benzo[1,4]dioxin-6-[Z]-ylmethylene)-2-([Z]-isopropylimino)-3-methoxy-phenyl)-thiazolidin-4-one,
5-[4-(2-hydroxy-ethoxy)-benz[Z]ylidene]-2-([Z]-isopropylimino)-3-(4-methoxy-phenyl)-thiazolidin-4-one,
5-[3-chloro-4-(2-hydroxy-ethoxy)-benz[Z]ylidene]-2-([Z]-isopropylimino)-3-(4-methoxy-phenyl)-thiazolidin-4-one,
3-allyl-5-[4-(2-hydroxy-ethoxy)-benz[Z]ylidene]-2-([Z]-isopropylimino)-thiazolidin-4-one,
3-allyl-5-[3-chloro-4-(2-hydroxy-ethoxy)-benz[Z]ylidene]-2-([Z]-isopropylimino)-thiazolidin-4-one,
rac-3-allyl-5-[3-chloro-4-(2,3-dihydroxy-propoxy)-benz[Z]ylidene]-2-([Z]-isopropylimino)-thiazolidin-4-one,
5-[4-(2-hydroxy-ethoxy)-benz[Z]ylidene]-3-phenyl-2-([Z]-propylimino)-thiazolidin-4-one,
5-[3-chloro-4-(2-hydroxy-ethoxy)-benz[Z]ylidene]-3-phenyl-2-([Z]-propylimino)-thiazolidin-4-one,
5-[4-(2-hydroxy-ethoxy)-3-methyl-benz[Z]ylidene]-3-phenyl-2-([Z]-propylimino)-thiazolidin-4-one,
rac-5-[3-chloro-4-(2,3-dihydroxy-propoxy)-benz[Z]ylidene]-3-phenyl-2-([Z]-propylimino)-thiazolidin-4-one,
5-[4-(2-hydroxy-ethoxy)-benz[Z]ylidene]-2-([Z]-propylimino)-3-o-tolyl-thiazolidin-4-one,
5-[4-(3-hydroxy-propoxy)-benz[Z]ylidene]-2-([Z]-propylimino)-3-o-tolyl-thiazolidin-4-one,
5-[3-chloro-4-(2-hydroxy-ethoxy)-benz[Z]ylidene]-2-([Z]-propylimino)-3-o-tolyl-thiazolidin-4-one,
5-[4-(2-hydroxy-ethoxy)-3-methyl-benz[Z]ylidene]-2-([Z]-propylimino)-3-o-tolyl-thiazolidin-4-one,
rac-5-[3-chloro-4-(2,3-dihydroxy-propoxy)-benz[Z]ylidene]-2-([Z]-propylimino)-3-o-tolyl-thiazolidin-4-one,
(R)-5-[3-chloro-4-(2,3-dihydroxy-propoxy)-benz[Z]ylidene]-2-([Z]-propylimino)-3-o-tolyl-thiazolidin-4-one,
(S)-5-[3-chloro-4-(2,3-dihydroxy-propoxy)-benz[Z]ylidene]-2-([Z]-propylimino)-3-o-tolyl-thiazolidin-4-one,
3-(2,3-dimethyl-phenyl)-5-[4-(2-hydroxy-ethoxy)-benz[Z]ylidene]-2-([Z]-propylimino)-thiazolidin-4-one,
rac-5-{4-[2-(2,3-dihydroxy-propoxy)-ethoxy]-benz[Z]ylidene}-3-(2,3-dimethyl-phenyl)-2-([Z]-propylimino)-thiazolidin-4-one,
5-[3-chloro-4-(2-hydroxy-ethoxy)-benz[Z]ylidene]-3-(2,3-dimethyl-phenyl)-2-([Z]-propylimino)-thiazolidin-4-one,
3-(2,3-dimethyl-phenyl)-5-[4-(2-hydroxy-ethoxy)-3-methyl-benz[Z]ylidene]-2-([Z]-propylimino)-thiazolidin-4-one,
3-(2,3-dimethyl-phenyl)-5-[4-(2-hydroxy-ethoxy)-3-methoxy-benz[Z]ylidene]-2-([Z]-propylimino)-thiazolidin-4-one,
rac-5-[4-(2,3-dihydroxy-propoxy)-benz[Z]ylidene]-3-(2,3-dimethyl-phenyl)-2-([Z]-propylimino)-thiazolidin-4-one,
rac-5-[3-chloro-4-(2,3-dihydroxy-propoxy)-benz[Z]ylidene]-3-(2,3-dimethyl-phenyl)-2-([Z]-propylimino)-thiazolidin-4-one,
2-([Z]-tert-butylimino)-5-[3-chloro-4-(2-hydroxy-ethoxy)-benz[Z]ylidene]-3-phenyl-thiazolidin-4-one,
2-(dimethyl-hydrazono)-5-[4-(2-hydroxy-ethoxy)-benz[Z]ylidene]-3-phenyl-thiazolidin-4-one,
5-[3-chloro-4-(2-hydroxy-ethoxy)-benz[Z]ylidene]-2-(dimethyl-hydrazono)-3-phenyl-thiazolidin-4-one,
2-([Z]-ethylimino)-5-[4-(2-hydroxy-ethoxy)-benz[Z]ylidene]-3-phenyl-thiazolidin-4-one,
5-[3-chloro-4-(2-hydroxy-ethoxy)-benz[Z]ylidene]-2-([Z]-Ethylimino)-3-phenyl-thiazolidin-4-one,
2-([Z]-ethylimino)-5-[4-(2-hydroxy-ethoxy)-benz[Z]ylidene]-3-o-tolyl-thiazolidin-4-one,
5-[3-chloro-4-(2-hydroxy-ethoxy)-benz[Z]ylidene]-2-([Z]-ethylimino)-3-o-tolyl-thiazolidin-4-one,
3-(2,3-dimethyl-phenyl)-2-([Z]-ethylimino)-5-[4-(2-hydroxy-ethoxy)-benz[Z]ylidene]-thiazolidin-4-one,
5-[3-chloro-4-(2-hydroxy-ethoxy)-benz[Z]ylidene]-3-(2,3-dimethyl-phenyl)-2-([Z]-ethylimino)-thiazolidin-4-one,
2-([Z]-butylimino)-5-[4-(2-hydroxy-ethoxy)-benz[Z]ylidene]-3-phenyl-thiazolidin-4-one,
2-([Z]-butylimino)-5-[3-chloro-4-(2-hydroxy-ethoxy)-benz[Z]ylidene]-3-phenyl-thiazolidin-4-one,
2-([Z]-butylimino)-5-[4-(2-hydroxy-ethoxy)-benz[Z]ylidene]-3-o-tolyl-thiazolidin-4-one,
2-([Z]-butylimino)-5-[3-chloro-4-(2-hydroxy-ethoxy)-benz[Z]ylidene]-3-o-tolyl-thiazolidin-4-one,
2-([Z]-butylimino)-3-(2,3-dimethyl-phenyl)-5-[4-(2-hydroxy-ethoxy)-benz[Z]ylidene]-thiazolidin-4-one,
2-([Z]-butylimino)-5-[3-chloro-4-(2-hydroxy-ethoxy)-benz[Z]ylidene]-3-(2,3-dimethyl-phenyl)-thiazolidin-4-one,
2-([Z]-sec-butylimino)-5-[3-chloro-4-(2-hydroxy-ethoxy)-benz[Z]ylidene]-3-phenyl-thiazolidin-4-one,
2-([Z]-cyclopropylimino)-5-[4-(2-hydroxy-ethoxy)-benz[Z]ylidene]-3-phenyl-thiazolidin-4-one,
3-cyclohexyl-5-[4-(2-hydroxy-ethoxy)-benz[Z]ylidene]-2-([Z]-isopropylimino)-thiazolidin-4-one,
b 5-[3-chloro-4-(2-hydroxy-ethoxy)-benz[Z]ylidene]-3-cyclohexyl-2-([Z]-isopropylimino)-thiazolidin-4-one, 5-[4-(2-Hydroxy-ethoxy)-benz[Z]ylidene]-3-isopropyl-2-([Z]-isopropylimino)-thiazolidin-4-one,
5-[3-chloro-4-(2-hydroxy-ethoxy)-benz[Z]ylidene]-3-isopropyl-2-([Z]-isopropylimino)-thiazolidin-4-one,
rac-5-[3-chloro-4-(2,3-dihydroxy-propoxy)-benz[Z]ylidene]-3-isopropyl-2-([Z]-isopropylimino)-thiazolidin-4-one,
5-[3-chloro-4-(2-hydroxy-ethoxy)-benz[Z]ylidene]-2-([Z]-isopropylimino)-3-phenyl-thiazolidin-4-one,
2-([Z]-allylimino)-5-[4-(2-hydroxy-ethoxy)-benz[Z]ylidene]-3-phenyl-thiazolidin-4-one,
2-([Z]-allylimino)-5-[3-chloro-4-(2-hydroxy-ethoxy)-benz[Z]ylidene]-3-phenyl-thiazolidin-4-one,
3-allyl-2-([Z]-allylimino)-5-[4-(2-hydroxy-ethoxy)-benz[Z]ylidene]-thiazolidin-4-one,
3-allyl-2-([Z]-allylimino)-5-[3-chloro-4-(2-hydroxy-ethoxy)-benz[Z]ylidene]-thiazolidin-4-one,
5-[3-chloro-4-(2-hydroxy-ethoxy)-benz[Z]ylidene]-2-([Z]-methylimino)-3-phenyl-thiazolidin-4-one,
5-[3-chloro-4-(2-hydroxy-ethoxy)-benz[Z]ylidene]-3-(2,3-dimethyl-phenyl)-2-([Z]-methylimino)-thiazolidin-4-one, More specific thiazolidin-4-one derivatives according to formula (II) are:
5-[4-(2-hydroxy-ethoxy)-benz[Z]ylidene]-2-([Z]-isopropylimino)-3-phenyl-thiazolidin-4-one,
5-[3-chloro-4-(2-hydroxy-ethoxy)-benz[Z]ylidene]-2-([Z]-isopropylimino)-3-phenyl-thiazolidin-4-one,
rac-5-[3-chloro-4-(2,3-dihydroxy-propoxy)-benz[Z]ylidene]-2-([Z]-isopropylimino)-3-o-tolyl-thiazolidin-4-one,
5-[3-chloro-4-(2-hydroxy-ethoxy)-benz[Z]ylidene]-3-(2,3-dimethyl-phenyl)-2-([Z]-isopropylimino)-thiazolidin-4-one,
rac-5-[3-chloro-4-(2,3-dihydroxy-propoxy)-benz[Z]ylidene]-3-(2,3-dimethyl-phenyl)-2-([Z]-isopropylimino)-thiazolidin-4-one,
5-[3-chloro-4-(2-hydroxy-ethoxy)-benz[Z]ylidene]-3-phenyl-2-([Z]-propylimino)-thiazolidin-4-one,
5-[4-(2-hydroxy-ethoxy)-3-methyl-benz[Z]ylidene]-3-phenyl-2-([Z]-propylimino)-thiazolidin-4-one,
rac-5-[3-chloro-4-(2,3-dihydroxy-propoxy)-benz[Z]ylidene]-3-phenyl-2-([Z]-propylimino)-thiazolidin-4-one,
rac-5-[3-chloro-4-(2,3-dihydroxy-propoxy)-benz[Z]ylidene]-2-([Z]-propylimino)-3-o-tolyl-thiazolidin-4-one,
(R)-5-[3-chloro-4-(2,3-dihydroxy-propoxy)-benz[Z]ylidene]-2-([Z]-propylimino)-3-o-tolyl-thiazolidin-4-one,
(S)-5-[3-chloro-4-(2,3-dihydroxy-propoxy)-benz[Z]ylidene]-2-([Z]-propylimino)-3-o-tolyl-thiazolidin-4-one,
5-[3-chloro-4-(2-hydroxy-ethoxy)-benz[Z]ylidene]-3-(2,3-dimethyl-phenyl)-2-([Z]-propylimino)-thiazolidin-4-one,
rac-5-[3-chloro-4-(2,3-dihydroxy-propoxy)-benz[Z]ylidene]-3-(2,3-dimethyl-phenyl)-2-([Z]-propylimino)-thiazolidin-4-one,
2-(dimethyl-hydrazono)-5-[4-(2-hydroxy-ethoxy)-benz[Z]ylidene]-3-phenyl-thiazolidin-4-one,
5-[3-chloro-4-(2-hydroxy-ethoxy)-benz[Z]ylidene]-2-([Z]-Ethylimino)-3-phenyl-thiazolidin-4-one,
5-[3-chloro-4-(2-hydroxy-ethoxy)-benz[Z]ylidene]-3-(2,3-dimethyl-phenyl)-2-([Z]-ethylimino)-thiazolidin-4-one,
5-[3-chloro-4-(2-hydroxy-ethoxy)-benz[Z]ylidene]-3-isopropyl-2-([Z]-isopropylimino)-thiazolidin-4-one, Compounds of General Formula (I) and General Formula (II) are suitable for the use as medicament.

Still a further object of the present invention is a process to prepare a pharmaceutical composition comprising a compound of the General Formula (I) or a compound of the General Formula (II) by mixing one or more active ingredients with inert excipients in a manner known per se.

The compounds of General Formulae (I) and (II) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the General Formula (I) and General Formula (II) of the present invention can be prepared according to the general sequence of reactions outlined below. Only a few of the synthetic possibilities leading to compounds of General Formula (I) and General Formula (II) are described as summarized in Scheme 1.

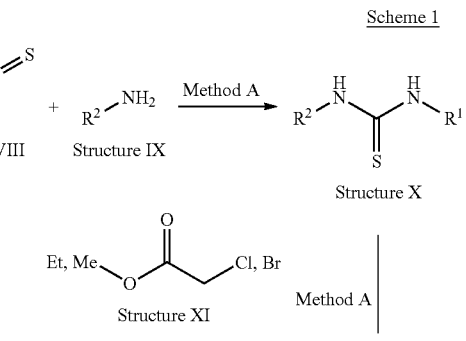

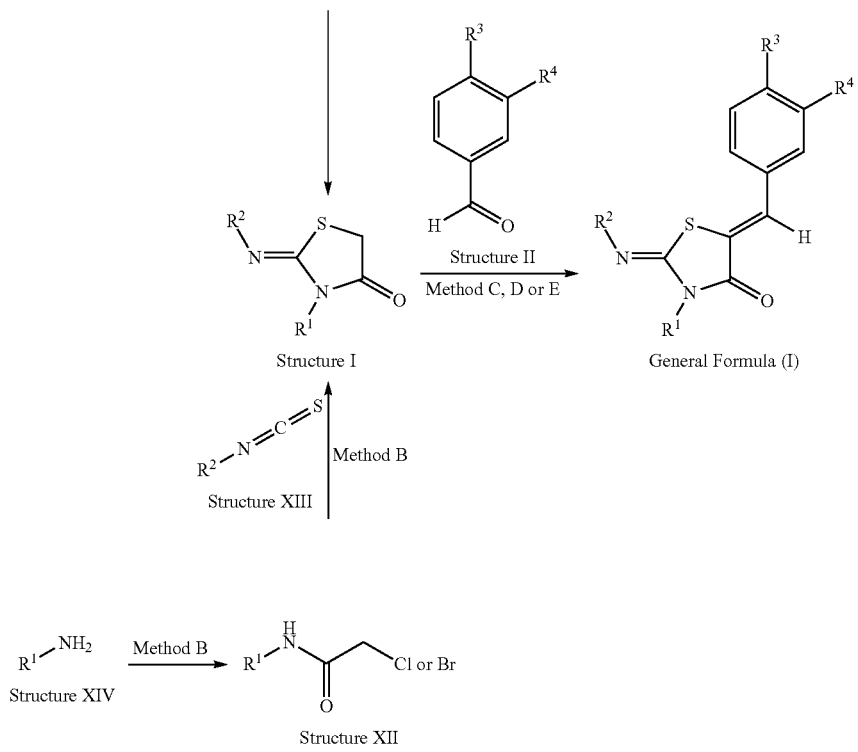

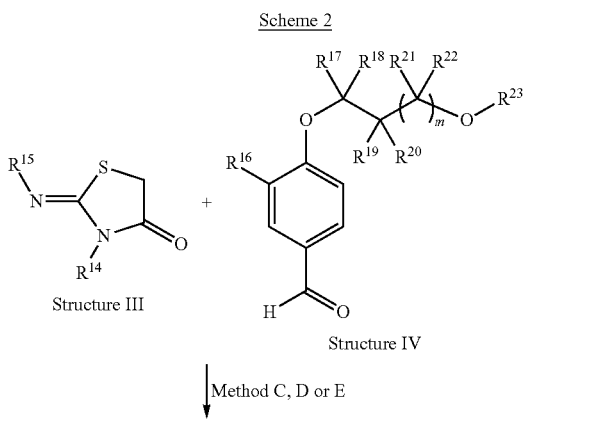

According to Scheme 1, compounds of the General Formula (I) can be prepared by reacting a compound of Structure I with a compound of Structure II, for instance, in acetic acid at elevated temperatures and in the presence of a base such as sodium acetate. The reaction can also be carried out in a non-polar solvent such as toluene or benzene in the presence of an amine such as pyrrolidine or piperidine.

Likewise, compounds of the General Formula (II) can be prepared by reacting a compound of Structure III with a compound of Structure IV (Scheme 2).

-continued

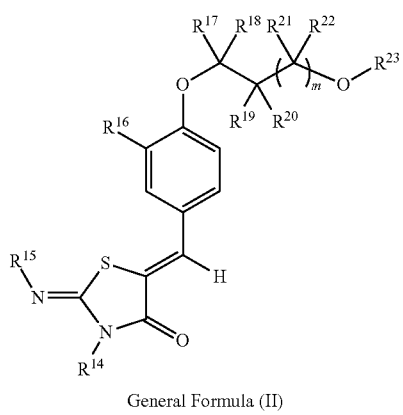

General Formula (II)

Depending on the nature of $R^{23}$, it may be beneficial to prepare the compounds of General Formula (II) by first reacting a compound of Structure III with the compound of Structure V to form a compound of Structure VI (Scheme 3). The compound of Structure VI is then treated with a compound of Structure VII wherein X represents a leaving group such a chlorine, a bromine or an iodine atom, or a sulfonic acid ester group in the presence of a base such as $K_2CO_3$, NaH, or triethylamine in a solvent such as THF, DMF, acetone, or DMSO.

Scheme 3

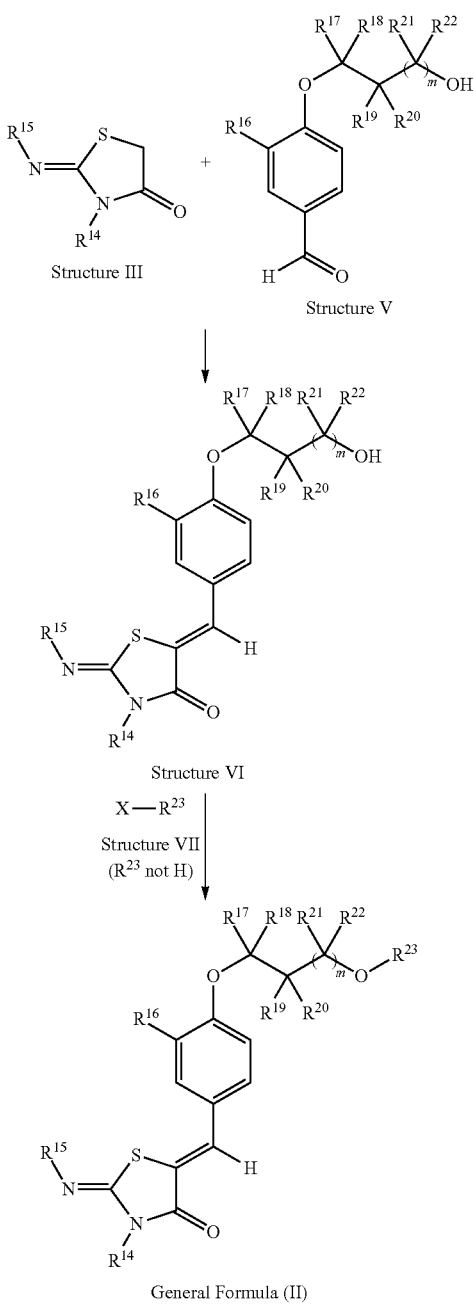

As outlined in Scheme 1, the compounds of Structure I can be prepared by reacting a compound of Structure VIII with a compound of Structure IX to form the intermediate of Structure X which is then cyclised to the compound of Structure I with a bromo- or chloroacetic acid ester of Structure XI. This reaction is ideally performed in a two step-one pot procedure at room temperature using an alcohol such as methanol or ethanol as solvent. The second step can be catalysed by the addition of pyridine.

Alternatively, the compounds of Structure I can also be prepared by reacting a compound of Structure XII with a compound of Structure XIII in the presence of a base such as NaH in a solvent such as THF or DMF. Compounds of the Structure XII are prepared by treating a compound of Structure XIV with chloroacetic acid chloride or bromoacetic acid bromide in a solvent such as THF, DMF or DCM in the presence of a base such as triethylamine, ethyldiisopropylamine at temperatures between −60 and +50° C. (Scheme 4).

Scheme 4

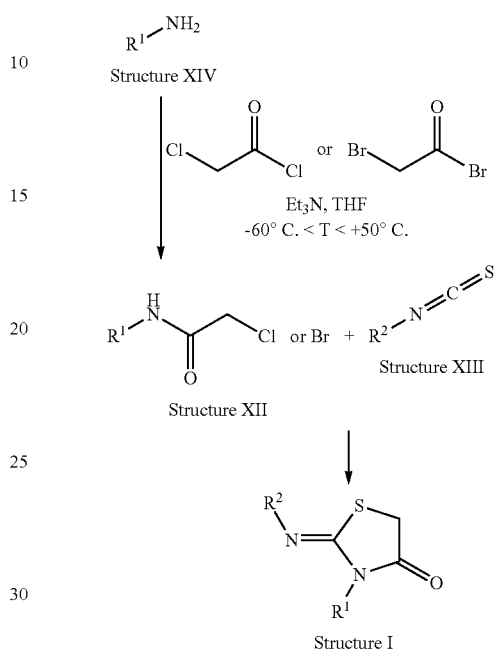

The preparation of compounds of Structure III is in analogy to the preparation of compounds of Structure I.

EXAMPLES

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 m, 120 A, gradient: 5-95% acetonitrile in water, 1 min, with 0.04% trifluoroacetic acid, flow: 4.5 ml/min), $t_R$ is given in min; by TLC (TLC-plates from Merck, Silica gel 60 $F_{254}$); or by melting point. Compounds are purified by preparative HPLC (column: Grom Saphir Rp-C$_{18}$, 110 A, 5 m, 30×30 mm, gradient: 10-95% acetonitrile in water containing 0.5% of formic acid, in 2 min, flow: 75 mL/min) or by MPLC (Labomatic MD-80-100 pump, Linear UVIS-201 detector, column: 350×18 mm, Labogel-RP-18-5s-100, gradient: 10% methanol in water to 100% methanol).

Abbreviations
aq. aqueous
atm atmosphere
DCM dichloromethane
DMF dimethylformamide
DMSO dimethylsulfoxide
EA ethyl acetate
h hour Hex hexane
HV high vacuum conditions
min minutes
THF tetrahydrofuran
rt room temperature
sat. saturated
$t_R$ retention time
tlc thin layer chromatography Typical Procedure for the Preparation of the
2-imino-thiazolidin-4-one Scaffold (Method A)

To a solution of isopropylamine (1.31 g, 22.19 mmol) in methanol (25 mL) is added portionwise phenylisothiocyanate (3.0 g, 22.19 mmol). The solution which becomes slightly warm during the addition is stirred at rt for 4 h before pyridine (2.63 g, 33.29 mmol) and methyl bromoacetate (3.39 g, 22.19 mmol) is added. The mixture is stirred for another 16 h at rt before it is poured onto 1 N aq. HCl (100 mL) and extracted with diethyl ether (150 mL). The aq. layer is neutralised by adding sat. aq. NaHCO$_3$ and extracted with diethyl ether (4×150 mL). The organic extracts are dried over MgSO$_4$ and evaporated. The remaining solid is suspended in diethyl ether/heptane, filtered off, washed with additional diethyl ether/heptane and dried to give 3-phenyl-2-[(Z)-isopropylimino]-thiazolidin-4-one.

Typical Procedure for the Preparation of the
2-imino-thiazolidin-4-one Scaffold (Method B)

a) A solution of aniline (9.31 g, 100 mmol) and triethylamine (15.2 g, 150 mmol) in THF (150 mL) is cooled to −40° C. before chloroacetic acid chloride (11.3 g, 100 mmol) is slowly added in portions such that the temperature does not rise above 0° C. After completion of the addition, the brown suspension is stirred at rt for 1 h. The dark purple mixture is poured onto water (300 mL) and extracted twice with EA (300 mL). The organic extracts are washed with sat. aq. NaHCO$_3$, 0.5 N aq. HCl, followed by water, and evaporated. The brown residue is suspended in diethyl ether, filtered off, washed with additional diethyl ether and dried under high vacuum to give 2-chloro-N-phenyl-acetamide. LC-MS: $t_R$=0.75 min, [M+1]$^+$=170, $^1$H NMR (CDCl$_3$): δ 8.22 (s br, 1H), 7.56-7.51 (m, 2H), 7.40-7.24 (m, 2H), 7.20-7.14 (m, 1H), 4.20 (s, 2H).

b) At rt, NaH (154 mg of 55% dispersion in mineral oil, 3.54 mmol) is added in portions to a solution of n-propylisothiocyanate (596 mg, 5.90 mmol) and the above 2-chloro-N-phenyl-acetamide (1000 mg, 5.90 mmol) in DMF (30 mL). Stirring is continued for 2 h after completion of the addition. The mixture is poured onto EA (150 mL) and is extracted twice with 1 N aq. HCl (200 mL). The aq. layer is neutralised by adding 3 N NaOH followed by sat. aq. NaHCO$_3$, and extracted twice with EA (200 mL). The organic extracts are washed with water (200 mL) and evaporated to give a pale yellow, crystalline solid. This material is suspended in a small amount of diethyl ether/hexane 1:1, filtered, washed with additional diethyl ether/hexane and dried under high vacuum to give 3-phenyl-2-[(Z)-propylimino]-thiazolidin-4-one.

Typical Procedure for the Introduction of the
Benzylidene Substituent (Method C)

A solution of 3-phenyl-2-[(Z)-isopropylimino]-thiazolidin-4-one (150 mg, 0.64 mmol), piperonal (192 mg, 1.28 mmol) and sodium acetate (105 mg, 1.28 mmol) in acetic acid (3 mL) is stirred at 110° C. for 4 h. The dark yellow to brown solution is cooled to rt, diluted with EA (75 mL), washed with sat. aq. NaHCO$_3$, followed by water, and evaporated. The crude product is purified by crystallisation from a small amount of methanol (approx. 5 mL) to give 5-benzo[1,3]dioxol-5-ylmeth-(Z)-ylidene-2-[(Z)-isopropylimino]-3-phenyl-thiazolidin-4-one.

Typical Procedure for the Introduction of the
benz-(Z)-ylidene Substituent (Method D)

A solution of 3-phenyl-2-[(Z)-isopropylimino]-thiazolidin-4-one (150 mg, 0.64 mmol), 4-(2-hydroxyethoxy)benzaldehyde (213 mg, 1.28 mmol) and sodium acetate (105 mg, 1.28 mmol) in acetic acid (3 mL) is stirred at 110° C. for 3 h. The brown solution is cooled to rt, diluted with EA (75 mL), washed with sat. aq. NaHCO$_3$, followed by water, and evaporated. The residue is dissolved in methanol (20 mL) and sodium methylate is added (150 mg). The resulting solution is allowed to stand for 40 min at rt before it is diluted with EA, washed with 10% aq. citric acid, and twice with water. The organic extracts are evaporated and the residue is crystallised from methanol to give (2Z,5Z)-3-phenyl-5-[4-(2-hydroxyethoxy)-benz-(Z)-ylidene]-2-[(Z)-isopropylimino]-thiazolidin-4-one.

Typical Procedure for the Introduction of the
benz-(Z)-ylidene Substituent (Method E)

A solution of 3-(2-methylphenyl)-2-[(Z)-isopropylimino]-thiazolidin-4-one (50 mg, 0.200 mmol), 2,3-dihydro-benzo[1,4]dioxine-6-carbaldehyde (49 mg, 0.300 mmol) and sodium acetate (33 mg, 0.400 mmol) in acetic acid (1 mL) is stirred at 110° C. for 5 h. The reaction mixture is cooled to rt and subjected to prep. HPLC purification. The product containing fractions are evaporated and dried to give 5-(2,3-dihydro-benzo[1,4]dioxin-6-ylmeth-(Z)-ylidene)-2-[(Z)-isopropylimino]-3-o-tolyl-thiazolidin-4-one.

Typical Procedure for the Introduction of the
benz-(Z)-ylidene Substituent (Method F)

A solution of 3-(2-methylphenyl)-2-[(Z)-propylimino]-thiazolidin-4-one (87 mg, 0.351 mmol), 3-chloro-4-((4R)-2,2-dimethyl-[1,3]dioxolan-4-ylmethoxy)-benzaldehyde (190 mg, 0.702 mmol) and sodium acetate (58 mg, 0.702 mmol) in acetic acid (4 mL) is stirred at 110° C. for 4 h. Water is added (50 µL) and stirring is continued at 110° C. for 1 h. The reaction mixture is cooled to rt, diluted with EA (75 mL), washed with sat. aq. NaHCO$_3$, followed by water, and evaporated. The residue is dissolved in methanol (20 mL) and sodium methylate is added (150 mg). The resulting solution is allowed to stand for 40 min at rt before it is diluted with EA, washed with 10% aq. citric acid, and twice with water. The organic extracts are evaporated and the residue is purified on prep. TLC plates using toluene/EA 1:3 to give 5-[3-chloro-4-((2R)-2,3-dihydroxy-propoxy)-benz-(Z)-ylidene]-2-[(Z)-propylimino]-3-o-tolyl-thiazolidin-4-one (98 mg) as a pale yellow foam.

Preparation of rac-4-[2-(2,3-dihydroxy-propoxy)-ethoxy]-benzaldehyde

To a solution of 4-82-hydroxyethoxy)-benzaldehyde (2.50 g, 15.0 mmol) in THF (100 mL) is added NaH (722 mg of 55% dispersion in mineral oil, 16.5 mmol) in two portions. The mixture is stirred at rt for 30 min and allylbromide (2.18 g, 18.0 mmol) is added. After stirring for 1 h at rt the thick mixture is diluted with DMF (20 mL) and stirring is continued for another 2 h. The mixture is diluted with EA (300 mL), washed with sat. aq. NaHCO₃ (150 mL), and water (2×150 mL) and concentrated. The residue is chromatographed on silica gel eluting with heptane/EA 3:2 to afford 4-(2-allyloxy-ethoxy)-benzaldehyde (2.11 g) as an almost colourless oil. LC-MS: $t_R$=0.88 min, $[M+1]^+$=207.

The above material (1.5 g, 7.27 mmol) is dissolved in acetone (40 mL) and treated with a 2.5% solution of OsO₄ in tert.-butanol (1.48 mL, 0.146 mmol). N-Methylmorpholine-N-oxide (1.03 g, 8.73 mmol) followed by water (1 mL) is added and the resulting yellow to green solution is stirred at rt for 4.5 h before it is diluted with EA (250 mL) and washed with 10% aq. citric acid solution (100 mL) and water (2×200 mL). The washings are extracted back once with EA (200 mL). The combined organic extracts are concentrated to leave rac-4-[2-(2,3-dihydroxy-propoxy)-ethoxy]-benzaldehyde (1.26 g) as a brownish oil. This material which reversibly polymerizes upon standing is used without further purification in the next step. LC-MS: $t_R$=0.62 min, $[M+1]^+$=241.

Preparation of
3-chloro-4-(2-acetoxy-ethoxy)-benzaldehyde

A mixture of 3-chloro-4-hydroxybenzaldehyde (10 g, 63.9 mmol), K₂CO₃ (26.5 g, 191.6 mmol) and 2-bromoethyl acetate (26.7 g, 159.7 mmol) in acetone (250 mL) is refluxed for 18 h before it is diluted with diethyl ether (200 mL) and washed with water (3×200 mL). The washings are extracted with diethyl ether (200 mL). The combined organic extracts are dried over MgSO₄ and concentrated. The remaining residue is purified by column chromatography on silica gel eluting with heptane/EA 1:1 to afford the title compound (6.44 g) as colourless solid. ¹H NMR (CDCl₃): δ 9.85 (s, 1H9, 7.91 (d, J=1.8 Hz, 1H), 7.75 (dd, J=1.8, 8.2 Hz, 1H), 7.03 (d, J=8.8 Hz, 1H), 4.53-4.49 (m, 2H), 4.35-4.31 (m, 2H), 2.12 (s, 3H).

Preparation of
4-(2-acetoxy-ethoxy)-3-fluoro-benzaldehyde

A mixture of 3-fluoro-4-hydroxybenzaldehyde (2.0 g, 14.3 mmol), K₂CO₃ (5.92 g, 42.8 mmol) and 2-bromoethyl acetate (4.77 g, 28.5 mmol) in acetone (30 mL) is stirred at 55° C. for 24 h before it is diluted with diethyl ether (150 mL) and washed with water (3×50 mL). The organic extract is dried over MgSO₄ and concentrated. The remaining residue is chromatographed on silica gel to give the title aldehyde (1.65 g) as a colourless oil. ¹H NMR (CDCl₃): δ 9.85 (s, 1H), 7.64-7.58 (m, 2H), 7.07 (t, J=8.2 Hz, 1H), 4.49-4.45 (m, 2H), 4.35-4.30 (m, 2H), 2.10 (s, 3H).

Preparation of
4-(2-acetoxy-ethoxy)-3-methylbenzaldehyde

A mixture of 4-hydroxy-3-methyl-benzaldehyde (7.0 g, 51.4 mmol), K₂CO₃ (21.32 g, 154.2 mmol) and 2-bromoethyl acetate (25.8 g, 154.2 mmol) in acetone (250 mL) is refluxed for 18 h before it is diluted with diethyl ether (300 mL) and washed with water (3×250 mL). The washings are extracted with diethyl ether (200 mL). The combined organic extracts are dried over MgSO₄ and concentrated. The remaining residue is purified by column chromatography on silica gel eluting with heptane/EA 1:1 to afford the title compound (11.14 g) as colourless solid. ¹H NMR (CDCl₃): δ 9.85 (s, 1H), 7.72-7.67 (m, 2H), 6.92-6.88 (m, 1H), 4.51-4.46 (m, 2H), 4.29-4.25 (m, 2H), 2.27 (s, 3H), 2.11 (s, 3H).

Preparation of
4-(2-acetoxy-ethoxy)-3-methoxy-benzaldehyde

A mixture of 4-hydroxy-3-methoxy-benzaldehyde (2.5 g, 16.4 mmol), K₂CO₃ (6.81 g, 49.3 mmol) and 2-bromoethyl acetate (5.49 g, 32.9 mmol) in acetone (50 mL) is refluxed for 48 h before it is diluted with diethyl ether (250 mL) and washed with water (2×200 mL). The washings are extracted with diethyl ether (200 mL). The combined organic extracts are dried over MgSO₄ and concentrated. The remaining residue is purified by column chromatography on silica gel eluting with heptane/EA 1:1 to afford the title compound (2.94 g) as colourless solid. ¹H NMR (CDCl₃): δ 9.85 (s, 1H), 7.45-7.41 (m, 2H), 6.99 (d, J=7.6 Hz, 1H), 4.51-4.47 (m, 2H), 4.34-4.30 (m, 2H), 3.94 (s, 3H), 2.11 (s, 3H).

Preparation of 4-(3-hydroxy-propoxy)-benzaldehyde

To a solution of 3-(4-hydroxymethylphenoxy)propionic acid (4.00 g, 20.40 mmol) in THF (20 mL) is added a solution of LiAlH₄ (10 mL, 1 M in THF). The mixture becomes warm and is diluted with THF (20 mL) before it is refluxed. After 1 and 2 h two further portions of LiAlH₄ (2×10 mL, 1 M in THF) are added. The mixture is refluxed overnight, cooled to rt and carefully quenched by the addition of water (1.2 g), 15% aq. NaOH (1.2 g) and water (3.2 g). The white precipitate is filtered off, and the filtrate is evaporated and dried to give 3-(4-hydroxymethyl-phenoxy)-propan-1-ol. ¹H NMR (D₆-DMSO): δ 7.21-7.15 (m, 2H), 6.86-6.81 (m, 2H), 5.00 (t, J=5.9 Hz, 1H), 4.51 (t, J=5.3 Hz, 1H), 4.39 (d, J=5.3 Hz, 2H), 3.99 (t, J=6.4 Hz, 2H), 3.57-3.50 (m, 2H), 1.83 (p, J 0 6.4 Hz, 2H).

To a suspension of the above 3-(4-hydroxymethyl-phenoxy)-propan-1-ol (1.50 g, 8.23 mmol) in acetonitrile (25 mL) is added N-methylmorpholine-N-oxide (1.50 g, 12.38 mmol) followed by tetrapropylammonium perruthenate (140 mg, 0.43 mmol). The dark solution is stirred at rt for 2 h before the solvent is removed in vacuo. The crude product is purified by column chromatography on silica gel (heptane/EA) to give 4-(3-hydroxy-propoxy)-benzaldehyde. ¹H NMR (D₆-DMSO): δ 9.83 (s, 1H), 7.85-7.81 (m, 2H), 7.12-7.07 (m, 2H9, 4.56 (t, J=5.3 Hz, 1H), 4.14 (t, J=6.4 Hz, 2H), 3.57-3.51 (m, 2H), 1.88 (p, J=6,4 Hz, 2H).

Preparation of
rac-4-(2,3-dihydroxy-propoxy)-benzaldehyde

To a solution of 4-allyloxybenzaldehyde (1.0 g, 6.17 mmol) in acetone (40 mL) and water (5 mL) is added a 2.5% solution of OsO₄ in tert. butanol (1.25 mL) followed by N-methyl morpholine-N-oxide (867 mg, 7.4 mmol). The pale yellow solution is stirred at rt for 6 h, diluted with EA (250 mL) and washed with 10% aq. citric acid solution (100 mL) and water (2×100 mL). The washings are extracted with EA (150 mL). The combined organic extracts are concentrated and purified by column chromatography on silica gel to give the title compound (731 mg) as a turbid oil. The title compound reversibly polymerizes upon standing. LC-MS: $t_R$=0.58 min, $[M+1+CH_3CN]^+$=238.

Preparation of rac-4-(2,3-dihydroxy-propoxy)-3-chloro-benzaldehyde

To a solution of 3-chloro-4-hydroxybenzaldehyde (5.0 g, 31.9 mmol) in DMF/THF 1:3 (120 mL) is added NaH (1.67 g of a 55% dispersion in mineral oil, 38.3 mmol) in four portions. The mixture is stirred at rt for 1 h before allylbromide (9.66 g, 79.8 mmol) is added. The reaction mixture is heated to 65° C. for 18 h, diluted with water (250 mL) and extracted with diethyl ether (3×250 mL). The organic extracts are washed with water (250 mL), combined and concentrated. The remaining oil is chromatographed on silic gel with heptane/EA 4:1 to afford 4-allyloxy-3-chlorobenzaldehyde (5.37 g) as an almost colourless oil. LC: $t_R$=0.95 min. The above 4-allyloxy-3-chloro-benzaldehyde (5.37 g, 27.3 mmol) is dissolved in acetone (100 mL) and water (10 mL) and treated with a 2.5% solution of $OsO_4$ in tert.-butanol (1.71 mL, 0.137 mmol $OsO_4$). N-methyl morpholine-N-oxide (3.87 g, 32.8 mmol) is added and the reaction mixture is stirred at rt for 20 h before it is diluted with EA (300 mL) and washed with 10% aq. citric acid solution (200 mL) and water (2×150 mL). The washings are extracted with EA (300 mL) and the combined organic extracts are dried over $MgSO_4$, filtered and concentrated to furnish the title compound (6.02 g) as beige foam which was used in the following steps without further purification. LC: $t_R$=0.67 min.

Preparation of 3-chloro-4-((4R)-2,2-dimethyl-[1,3]dioxolan-4-ylmethoxy)-benzaldehyde To a solution of 3-chloro-4-hydroxybenzaldehyde (4.21 g, 27 mmol) in degassed toluene (100 mL) is added ((4R)-2,2-dimethyl-[1,3]dioxolan-4-yl)-methanol (5.35 g, 40.5 mmol), 1,1'-(azodicarbonyl)dipiperidide (13.63 g, 54 mmol) followed by tributylphosphine (10.93 g, 54 mmol). The mixture becomes slightly warm and a precipitate forms. The reaction mixture is diluted with degassed toluene (500 mL) and is stirred at rt for 2 h, then at 60° C. for further 18 h before it is washed with 1 N aq. NaOH (3×150 mL) and water (150 mL). The organic phase is dried over $MgSO_4$, filtered and concentrated to leave a dark brown oil which is chromatographed on silica gel eluting with hexane/EA 4:1 to give the title compound (4.30 g) as yellow oil. $^1$H NMR (CDCl$_3$): δ 9.82 (s, 1H), 7.89 (d, J=1.8 Hz, 1H), 7.74 (dd, J=1.8, 8.2 Hz, 1H), 7.05 (d, J=8.2 Hz, 1H), 4.56-4.43 (m, 1H), 4.23-4.17 (m, 2H), 4.14-4.08 (m, 1H), 4.06-4.00 (m, 1H), 1.47 (s, 3H), 1.41 (s, 3H).

Preparation of 3-chloro-4-((4S)-2,2-dimethyl-[1,3]dioxolan-4-ylmethoxy)-benzaldehyde The title compound (174 mg) is obtained as a pale yellow oil starting from 3-chloro-4-hydroxybenzaldehyde (500 mg, 3.20 mmol), ((4S)-2,2-dimethyl-[1,3]dioxolan-4-yl)-methanol (633 mg, 4.79 mmol), 1,1'-(azodicarbonyl)dipiperidide (1.61 g, 6.39 mmol), and tributylphosphine (1.29 g, 6.39 mmol) following the procedure given for the (R)-enantiomer above using THF as solvent, however.

Preparation of rac-2-hydroxymethyl-2,3-dihydro-benzo[1,4]dioxine-6-carbaldehyde

To a cold (5° C.) solution of 3,4-dihydroxybenzaldehyde (3.20 g, 23.2 mmol) in DMF (70 mL) is carefully added NaH (1.96 g 55% in mineral oil, 48.5 mmol) in portions. The temperature rises to 12° C. Upon completion of the addition, the cooling is removed and a solution of 2-chloromethyl-oxirane (2.57 g, 27.7 mmol) in DMF (3 mL) is added. The reaction mixture is stirred at rt overnight. The mixture is diluted with 1N aq. NaOH (150 mL) and extracted with EA (2×200 mL). The organic extracts are washed with 1 M aq. NaOH (2×200 mL) and water (200 mL) combined, dried over $MgSO_4$, filtered and concentrated. The remaining residue is purified by column chromatography on silica gel eluting with heptene/EA 5:1 to 1:1 to afford the title aldehyde (0.53 g) as a solid. LC: $t_R$=0.69 min. $^1$H NMR (D$_6$-DMSO): δ 9.77 (s, 1H), 7.41 (dd, J=2.3, 8.2 Hz, 1H), 7.36 (d, J=2.3 Hz, 1H), 7.04 (d, J=8.2 Hz, 1H), 5.10 (t, J=5.9 Hz, 1H, D$_2$O exchangeable), 4.37 (dd, J=2.3, 11.1 Hz, 1H), 4.30-4.23 (m, 1H), 4.05 (dd, J=7.6, 11.1 Hz, 1H), 3.67-3.60 (m, 2H).

Scaffold 1

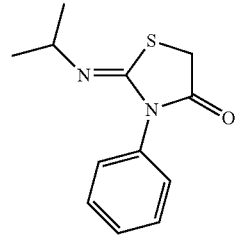 [SMILES: CC(C)/N=C1\SCC(=O)N1c1ccccc1]

2-[(Z)-Isopropylimino]-3-phenyl-thiazolidin-4-one is prepared as described in Method A. LC-MS: $t_R$=0.58 min, [M+1]$^+$=235. $^1$H NMR (CDCl$_3$): δ 7.50-7.36 (m, 3H), 7.29-7.24 (m, 2H), 3.98 (s, 2H), 3.51 (hept, J=6.4 Hz, 1H), 1.14 (d, J=5.9 Hz, 6H).

Scaffold 2

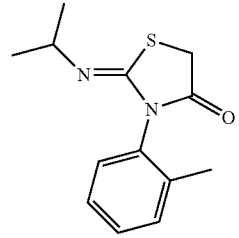 [SMILES: Cc1ccccc1N1C(=O)CS/C1=N\C(C)C]

2-[(Z)-Isopropylimino]-3-o-tolyl-thiazolidin-4-one is obtained following Method A and starting from o-tolyl-isothiocyanate (3.0 g, 20.10 mmol), isopropylamine (1.19 g, 20.10 mmol), and methyl bromoacetate (3.08 g, 20.1 mmol). LC-MS: $t_R$=0.67 min, [M+1]$^+$=249; $^1$H NMR (CDCl$_3$): δ 7.34-7.26 (m, 3H), 7.14-7.08 (m, 1H), 4.00 (s, 2H), 3.50 (hept, J=6.4 Hz, 1H), 2.16 (s, 3H), 1.12 (d, J=6.4 Hz, 3H), 1.11 (d, J=6.4 Hz, 3H).

Scaffold 3

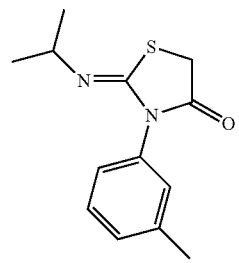 [SMILES: Cc1cccc(N2C(=O)CS/C2=N\C(C)C)c1]

2-[(Z)-Isopropylimino]-3-m-tolyl-thiazolidin-4-one is obtained following Method A and starting from m-tolyl-isothiocyanate (3.0 g, 20.10 mmol), isopropylamine (1.19 g, 20.10 mmol), and methyl bromoacetate (3.08 g, 20.1 mmol). LC-MS: $t_R$=0.65 min, [M+1]$^+$=249; $^1$H NMR (CDCl$_3$): δ 7.37-7.30 (m, 1H), 7.21-7.17 (m, 1H), 7.08-7.03 (m, 2H), 3.96 (s, 2H), 3.50 (hept, J=6.4 Hz, 1H), 2.40 (s, 3H), 1.14 (d, J=6.4 Hz, 6H).

Scaffold 4

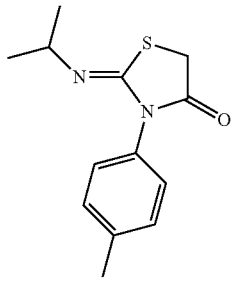 [SMILES: Cc1ccc(N2C(=O)CS/C2=N\C(C)C)cc1]

2-[(Z)-Isopropylimino]-3-p-tolyl-thiazolidin-4-one is obtained following Method A and starting from p-tolyl-isothiocyanate (3.0 g, 20.10 mmol), isopropylamine (1.19 g, 20.10 mmol), and methyl bromoacetate (3.08 g, 20.1 mmol). LC-MS: $t_R$=0.64 min, [M+1]$^+$=249; $^1$H NMR (CDCl$_3$): δ 7.28-7.24 (m, 2H), 7.16-7.12 (m, 2H), 3.96 (s, 2H), 3.50 (hept, J=6.4 Hz, 1H), 2.39 (s, 3H), 1.14 (d, J=6.4 Hz, 6H).

Scaffold 5

2-[(Z)-Isopropylimino]-3-(2,3-dimethylphenyl)-thiazolidin-4-one is obtained following Method A and starting from 2,3-dimethylphenylisothiocyanate (3.0 g, 18.38 mmol), isopropylamine (1.09 g, 18.38 mmol), and methyl bromoacetate (2.81 g, 18.38 mmol). LC-MS: $t_R$=0.74 min, [M+1]$^+$=263; $^1$H NMR (CDCl$_3$): δ 7.22-7.14 (m, 2H), 6.98-6.93 (m, 1H), 3.98 (s, 2H), 3.48 (hep, J=6.4 Hz, 1H), 2.32 (s, 3H), 2.02 (s, 3H), 1.10 (d, J=6.4 Hz, 6H).

Scaffold 6

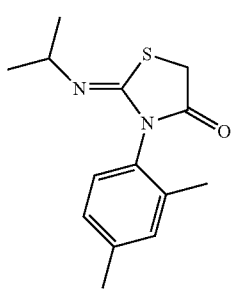 [SMILES: Cc1ccc(N2C(=O)CS/C2=N\C(C)C)c(C)c1]

2-[(Z)-Isopropylimino]-3-(2,4-dimethylphenyl)-thiazolidin-4-one is obtained following Method A and starting from 2,4-dimethylphenylisothiocyanate (3.0 g, 18.38 mmol), isopropylamine (1.64 g, 27.57 mmol), and methyl bromoacetate (2.81 g, 18.38 mmol). LC-MS: $t_R$=0.75 min, [M+1]$^+$=263; $^1$H NMR (CDCl$_3$): δ 7.12-7.06 (m, 2H), 6.98 (d, J=8.2 Hz, 1H), 3.98 (s, 2H), 3.49 (hept, J=6.0 Hz, 1H), 2.35 (s, 3H), 2.12 (s, 3H), 1.12 (d, J=5.9 Hz, 3H), 1.11 (d, J=6.4 Hz, 3H).

Scaffold 7

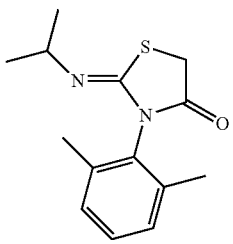 [SMILES: Cc1cccc(C)c1N1C(=O)CS/C1=N\C(C)C]

2-[(Z)-Isopropylimino]-3-(2,6-dimethylphenyl)-thiazolidin-4-one is obtained following Method A and starting from 2,6-dimethylphenylisothiocyanate (3.0 g, 18.38 mmol), isopropylamine (1.09 g, 18.38 mmol), and methyl bromoacetate (2.81 g, 18.38 mmol). LC-MS: $t_R$=0.80 min, [M+1]$^+$=263; $^1$H NMR (CDCl$_3$): δ 7.24-7.10 (m, 3H), 4.00 (s, 2H), 3.48 (hept, J=6.4 Hz, 1H), 2.14 (s, 6H), 1.10 (d, J=6.4 Hz, 6H).

Scaffold 8

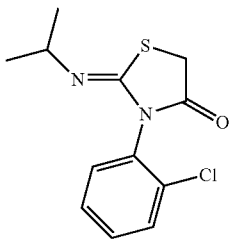 [SMILES: CC(C)/N=C1\SCC(=O)N1c1ccccc1Cl]

2-[(Z)-Isopropylimino]-3-(2-chlorophenyl)-thiazolidin-4-one is obtained following Method A and starting from 2-chlorophenylisothiocyanate (3.0 g, 17.68 mmol), isopropylamine (1.04 g, 17.68 mmol), and methyl bromoacetate (2.70 g, 17.68 mmol). LC-MS: $t_R$=0.81 min, [M+1]$^+$=269; $^1$H NMR (CDCl$_3$): δ 7.53-7.48 (m, 1H), 7.40-7.34 (m, 2H), 7.30-7.24 (m, 1H), 4.07-3.93 (m, 2H), 3.48 (hept, J=6.4 Hz, 1H), 1.11 (d, J=6.4 Hz, 3H), 1.10 (d, J=6.4 Hz, 3H).

Scaffold 9

2-[(Z)-Isopropylimino]-3-(2-methoxyphenyl)-thiazolidin-4-one is obtained following Method A and starting from 2-methoxyphenylisothiocyanate (3.0 g, 18.16 mmol), isopropylamine (1.08 g, 18.16 mmol), and methyl bromoacetate (2.78 g, 18.16 mmol). LC-MS: $t_R$=0.62 min, [M+1]$^+$=265; $^1$H NMR (CDCl$_3$): δ 7.42-7.35 (m, 1H), 7.19-7.14 (m, 1H), 7.06-6.98 (m, 2H), 3.80 (s, 3H), 3.55-3.42 (m, 1H), 1.11 (t, 5.9 Hz, 6H).

Scaffold 10

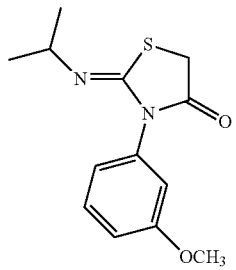 [SMILES: COc1cccc(N2C(=O)CS/C2=N\C(C)C)c1]

2-[(Z)-Isopropylimino]-3-(3-methoxyphenyl)-thiazolidin-4-one is obtained following Method A and starting from 3-methoxyphenylisothiocyanate (3.0 g, 18.16 mmol), isopropylamine (1.08 g, 18.16 mmol), and methyl bromoacetate (2.78 g, 18.16 mmol). LC-MS: $t_R$=0.65 min, [M+1]$^+$=265; $^1$H NMR (CDCl$_3$): δ 7.35 (t, J=7.8 Hz, 1H), 6.95-6.90 (m, 1H), 6.87-6.83 (m, 1H), 6.82-6.80 (m, 1H), 3.96 (s, 2H), 3.82 (s, 3H), 3.54-3.45 (m, 1H), 1.13 (d, J=5.9 Hz, 6H).

Scaffold 11

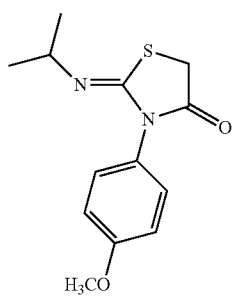 [SMILES: COc1ccc(N2C(=O)CS/C2=N\C(C)C)cc1]

2-[(Z)-Isopropylimino]-3-(4-methoxyphenyl)-thiazolidin-4-one is obtained following Method A and starting from 4-methoxyphenylisothiocyanate (3.0 g, 18.16 mmol), isopropylamine (1.08 g, 18.16 mmol), and methyl bromoacetate (2.78 g, 18.16 mmol). LC-MS: $t_R$=0.62 min, [M+1]$^+$=265; $^1$H NMR (CDCl$_3$): δ 7.20-7.14 (m, 2H), 7.00-6.94 (m, 2H), 3.96 (s, 2H), 3.84 (s, 3H), 3.51 (hept, J=6.4 Hz, 1H), 1.14 (d, J=6.4 Hz, 6H).

Scaffold 12

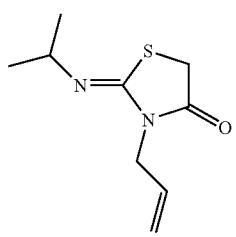

2-[(Z)-Isopropylimino]-3-allyl-thiazolidin-4-one is obtained following Method A and starting from allylisothiocyanate (5.95 g, 60 mmol), isopropylamine (3.55 g, 60 mmol), and methyl bromoacetate (9.18 g, 60 mmol). LC-MS: $t_R$=0.55 min, [M+1]$^+$=199; $^1$H NMR (CDCl$_3$): δ 5.82-5.69 (m, 1H), 5.10-5.02 (m, 2H), 4.17-4.13 (m, 2H), 4.01 (s, 2H), 3.39 (hept, J=6.1 Hz, 1H), 1.10 (d, J=5.9 Hz, 6H).

Scaffold 13

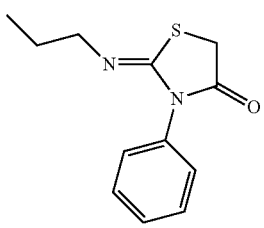 [SMILES: CCC/N=C1\SCC(=O)N1c1ccccc1]

3-Phenyl-2-[(Z)-propylimino]-thiazolidin-4-one is prepared as described in Method B. LC-MS: $t_R$=0.60 min, [M+1]$^+$=235, $^1$H NMR (CDCl$_3$): δ 7.51-7.36 (m, 3H), 7.28-7.24 (m, 2H), 3.99 (s, 2H), 3.27 (t, J=7.0 Hz, 2H), 1.60 (hex, J=7.0 Hz, 2H), 0.91 (t, J=7.6 Hz, 3H).

Scaffold 14

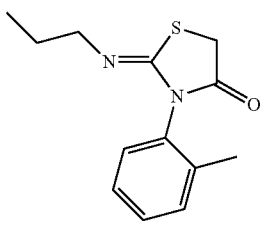 [SMILES: CCC/N=C1\SCC(=O)N1c1ccccc1C]

2-[(Z)-Propylimino]-3-o-tolyl-thiazolidin-4-one is obtained following Method B and starting from toluidine (2.21 g, 20.6 mmol), chloroacetyl chloride (2.32 g, 20.6 mmol) and n-propylisothiocyanate (1.62 g, 16.0 mmol). LC-MS: $t_R$=0.68 min, [M+1]$^+$=249. $^1$H NMR (CDCl$_3$): δ 7.34-7.26 (m, 3H), 7.14-7.09 (m, 1H), 4.01 (s, 2H), 3.34-3.18 (m, 2H), 2.18 (s, 3H), 1.58 (hept, J=7.0 Hz, 2H), 0.88 (t, J=7.0 Hz, 3H).

Scaffold 15

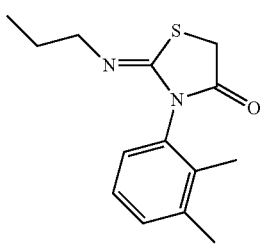 [SMILES: CCC/N=C1\SCC(=O)N1c1cccc(C)c1C]

2-[(Z)-Propylimino]-3-(2,3-dimethylphenyl)-thiazolidin-4-one is obtained following Method B and starting from 2,3-dimethylaniline (3.36 g, 27.8 mmol), chloroacetyl chloride (3.14 g, 27.7 mmol) and n-propylisothiocyanate (2.05 g, 20.2 mmol). LC-MS: $t_R$=0.71 min, [M+1]$^+$=263. $^1$H NMR (CDCl$_3$): δ 7.22-7.16 (m, 2H), 6.98-6.94 (m, 1H), 4.00 (s, 2H), 3.34-3.18 (m, 2H), 2.32 (s, 3H), 2.05 (s, 3H), 1.57 (hex, J=7.3 Hz, 2H), 0.88 (t, J=7.6 Hz, 3H).

Scaffold 16

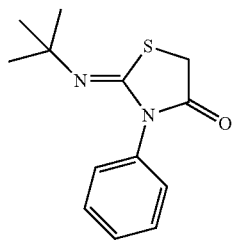 [SMILES: CC(C)(C)/N=C1\SCC(=O)N1c1ccccc1]

2-[(Z)-tert.-Butylimino]-3-o-tolyl-thiazolidin-4-one (6.79 g) is obtained as an off-white crystalline powder following Method A and starting from phenylisothiocyanate (5.0 g, 37.0 mmol), tert. butylamine (2.71 g, 37.0 mmol), and methyl bromoacetate (5.66 g, 37.0 mmol). LC-MS: $t_R$=0.69 min, [M+1]$^+$=249, $^1$H NMR (CDCl$_3$): δ 7.46-7.31 (m, 3H), 7.24-7.19 (m, 2H), 3.98 (s, 2H), 1.26 (s, 9H).

Scaffold 17

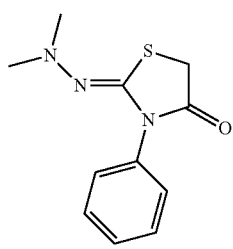 [SMILES: CN(C)/N=C1\SCC(=O)N1c1ccccc1]

2-[(Z)-(Dimethyl-hydrazono)]-3-phenyl-thiazolidin-4-one is obtained following Method A and starting from phenylisothiocyanate (4.05 g, 30.0 mmol), dimethylhydrazine (asym.) (1.80 g, 30.0 mmol), and methyl bromoacetate (4.59 g, 30.0 mmol). LC-MS: $t_R$=0.69 min, [M+1]$^+$=236, $^1$H NMR (CDCl$_3$): δ 7.50-7.36 (m, 3H), 7.32-7.28 (m, 2H), 3.82 (s, 2H), 2.48 (s, 6H).

Scaffold 18

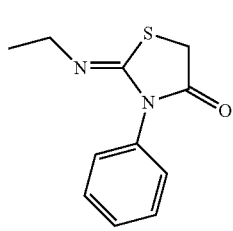

2-[(Z)-Ethylimino]-3-phenyl-thiazolidin-4-one (1.02 g) is obtained as an off-white powder following Method B and starting from 2-chloro-N-phenyl-acetamide (7.50 g, 44.2 mmol) and ethylisothiocyanate (3.85 g, 44.2 mmol). LC-MS: $t_R$=0.48 min, [M+1]$^+$=221. $^1$H NMR (CDCl$_3$): δ 7.52-7.37 (m, 3H), 7.29-7.27 (m, 2H), 4.01 (s, 2H), 3.37 (q, J=7.6 Hz, 2H), 1.20 (t, J=7.6 Hz, 3H).

Scaffold 19

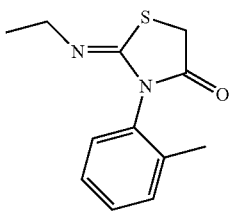 [SMILES: CC/N=C1\SCC(=O)N1c1ccccc1C]

2-[(Z)-Ethylimino]-3-(2-methylphenyl)-thiazolidin-4-one is prepared following Method B and starting from o-tolylamine, chloroacetyl chloride and ethylisothiocyanate. LC-MS: $t_R$=0.59 min, [M+1]$^+$=235, $^1$H NMR (CDCl$_3$): δ 7.36-7.28 (m, 3H), 7.15-7.10 (m, 1H), 4.01 (s, 2H), 3.41-3.30 (m, 2H), 2.19 (s, 3H), 1.20-1.13 (m, 3H).

Scaffold 20

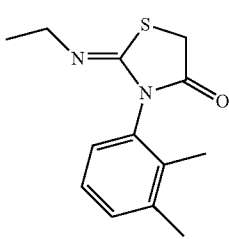 [SMILES: CC/N=C1\SCC(=O)N1c1cccc(C)c1C]

2-[(Z)-Ethylimino]-3-(2,3-dimethylphenyl)-thiazolidin-4-one is prepared following Method B and starting from 2,3-dimethylaniline, chloroacetyl chloride and ethylisothiocyanate. LC-MS: $t_R$=0.66 min, [M+1]$^+$=249, $^1$H NMR (CDCl$_3$): δ 7.24-7.19 (m, 2H), 7.00-6.96 (m, 1H), 4.01 (s, 2H), 3.45-3.27 (m, 2H), 2.34 (s, 3H), 2.05 (s, 3H), 1.16 (t, J=7.0 Hz, 3H).

Scaffold 21

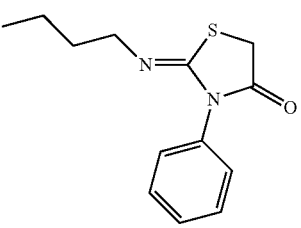 [SMILES: CCCC/N=C1\SCC(=O)N1c1ccccc1]

2-[(Z)-n-butylimino]-3-phenyl-thiazolidin-4-one (1.80 g) is obtained as a pale beige powder following Method B and starting from 2-chloro-N-phenyl-acetamide (7.50 g, 44.2 mmol) and n-butylisothiocyanate (5.09 g, 44.2 mmol). LC-MS: $t_R$=0.69 min, [M+1]$^+$=249. $^1$H NMR (CDCl$_3$): δ 7.51-7.37 (m, 3H), 7.29-7.25 (m, 2H), 4.00 (s, 2H), 3.31 (t, J=7.0 Hz, 2H), 1.62-1.52 (m, 2H), 1.41-1.28 (m, 2H), 0.92 (t, J=7.0 Hz, 3H).

Scaffold 22

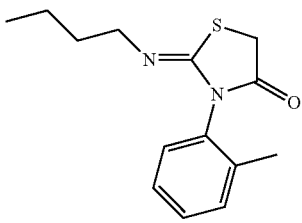 [SMILES: CCCC/N=C1\SCC(=O)N1c1ccccc1C]

2-[(Z)-n-butylimino]-3-(2-methylphenyl)-thiazolidin-4-one is prepared following Method B and starting from o-tolylamine, chloroacetyl chloride and n-butylisothiocyanate. LC-MS: $t_R$=0.77 min, [M+1]$^+$=263, $^1$H NMR (CDCl$_3$): δ 7.35-7.28 (m, 3H), 7.14-7.10 (m, 1H), 4.01 (s, 2H), 3.38-3.22 (, 2H), 2.18 (s, 3H), 1.59-1.47 (m, 2H), 1.38-1.25 (m, 2H), 0.90 (t, J=7.0 Hz, 3H).

Scaffold 23

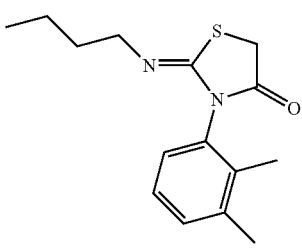 [SMILES: CCCC/N=C1\SCC(=O)N1c1cccc(C)c1C]

2-[(Z)-n-butylimino]-3-(2,3-dimethylphenyl)-thiazolidin-4-one is prepared following Method B and starting from 2,3-dimethylaniline, chloroacetyl chloride and n-butylisothiocyanate. LC-MS: $t_R$=0.80 min, [M+1]$^+$=277, $^1$H NMR (CDCl$_3$): δ 7.23-7.16 (m, 2H), 6.99-6.94 (m, 1H), 4.01 (s, 2H), 3.38-3.23 (m, 2H), 2.33 (s, 3H), 2.05 (s, 3H), 1.59-1.49 (m, 2H), 1.38-1.25 (m, 2H), 0.91 (t, J=7.0 Hz, 3H).

Scaffold 24

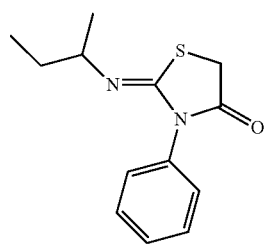 [SMILES: CCC(C)/N=C1\SCC(=O)N1c1ccccc1]

rac-2-[(Z)-sec-Butylimino]-3-phenyl-thiazolidin-4-one (6.98 g) is obtained as a white powder following Method A and starting from sec-butylamine (2.70 g, 36.98 mmol), phenylisothiocyanate (5.00 g, 36.98 mmol) and methyl bromoacetate (5.66 g, 36.98 mmol). LC-MS: $t_R$=0.68 min, [M+1]$^+$=249, $^1$H NMR (CDCl$_3$): δ 7.48-7.33 (m, 3H), 7.28-7.23 (m, 2H), 3.96 (s, 2H), 3.21 (hex, J=6.4 Hz, 1H), 1.52-1.39 (m, 2H), 1.09 (d, J=6.4 Hz, 3H), 0.82 (t, J=7.3 Hz, 3H).

Scaffold 25

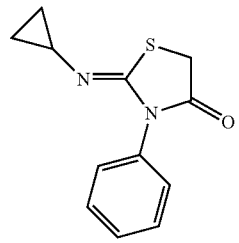 [SMILES: O=C1CS/C(=N\C2CC2)N1c1ccccc1]

2-[(Z)-Cyclopropylimino]-3-phenyl-thiazolidin-4-one (1.62 g) is obtained as a white powder following Method A and starting from cyclopropylamine (0.84 g, 14.8 mmol), phenylisothiocyanate (2.00 g, 14.8 mmol) and methyl bromoacetate (2.26 g, 14.8 mmol). LC-MS: $t_R$=0.64 min, [M+1]$^+$=233, $^1$H NMR (CDCl$_3$): δ 7.47-7.33 (m, 3H), 7.24-7.20 (m, 2H), 4.00 (s, 2H), 2.67 (hept, J=3.5 Hz, 1H), 0.82-0.75 (m, 2H), 0.64-0.59 (m, 2H).

Scaffold 26

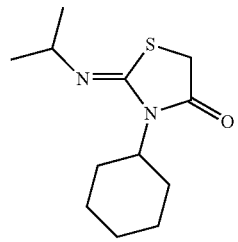 [SMILES: CC(C)/N=C1\SCC(=O)N1C1CCCCC1]

3-Cyclohexyl-2-[(Z)-isopropylimino]-thiazolidin-4-one is prepared starting from cyclohexylamine, chloroacetyl chloride and isopropylisothiocyanate following Method B. LC-MS: $t_R$=0.83 min, [M+1]$^+$=241, $^1$H NMR (CDCl$_3$): δ 4.30 (tt, J=3.6, 12.0 Hz, 1H), 3.69 (s, 2H), 3.37 (hep, J=6.4 Hz, 1H), 2.40-2.25 (m, 2H), 1.84-1.75 (m, 2H), 1.64-1.50 (m, 2H), 1.40-1.20 (m, 4H), 1.14 (d, J=6.4 Hz, 6H).

Scaffold 27

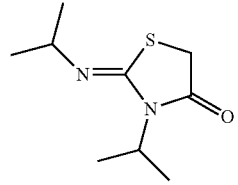

2-[(Z)-Isopropylimino]-3-isopropyl-thiazolidin-4-one (2.68 g) is obtained as a colourless oil following Method A and starting from isopropylamine (1.17 g, 19.8 mmol), isopropylisothiocyanate (2.00 g, 19.8 mmol) and methyl bromoacetate (3.02 g, 19.8 mmol). LC-MS: $t_R$=0.61 min, [M+1]$^+$=201, $^1$H NMR (CDCl$_3$): δ 4.73 (hept, J=7.0 Hz, 1H), 3.71 (s, 2H), 3.40 (hept, J=6.0 Hz, 1H), 1.42 (d, J=7.0 Hz, 6H), 1.17 (d, J=6.0 Hz, 6H).

Scaffold 28

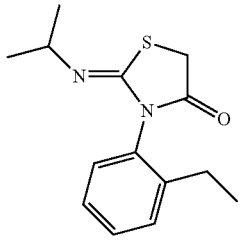 [SMILES: CCc1ccccc1N1C(=O)CS/C1=N\C(C)C]

2-[(Z)-Isopropylimino]-3-(2-ethylphenyl)-thiazolidin-4-one (5.07 g) is obtained as an off-white powder following Method A and starting from isopropylamine (1.98 g, 33.5 mmol), 2-ethylphenylisothiocyanate (5.0 g, 30.8 mmol) and methyl bromoacetate (5.12 g, 33.5 mmol). LC-MS: $t_R$=0.90 min, [M+1]$^+$=223, $^1$H NMR (CDCl$_3$): δ 7.41-7.26 (m, 3H), 7.08 (d, J=7.6 Hz, 1H), 3.99 (s, 2H), 3.48 (hept, J=6.4 Hz, 1H), 2.49 (q, J=7.6 Hz, 2H), 1.19 (t, J=7.6 Hz, 3H), 1.09 (d, J=6.4 Hz, 6H).

Scaffold 29

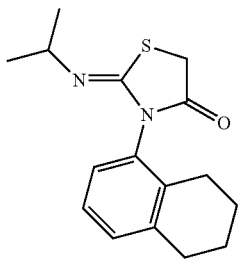 [SMILES: CC(C)/N=C1\SCC(=O)N1c1cccc2c1CCCC2]

2-[(Z)-Isopropylimino]-3-(5,6,7,8-tetrahydro-naphthalen-1-yl)-thiazolidin-4-one is obtained as a yellow solid following Method B and starting from 5,6,7,8-tetrahydro-naphthalen-1-ylamine, chloroacetyl chloride and isopropylisothiocyanate. LC-MS: $t_R$=0.81 min, [M+1]$^+$=289, $^1$H NMR (CDCl$_3$): δ 7.23-7.13 (m, 2H), 6.96-6.91 (m, 1H), 3.99 (s, 2H), 3.50 (hept, J=6.4 Hz, 1H), 2.86-2.80 (m, 2H), 2.52-2.45 (m, 2H), 1.84-1.74 (m, 4H), 1.13 (d, J=6.4 Hz, 6H).

Scaffold 30

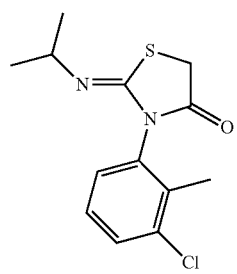 [SMILES: Cc1c(Cl)cccc1N1C(=O)CS/C1=N\C(C)C]

2-[(Z)-Isopropylimino]-3-(3-chloro-2-methylphenyl)-thiazolidin-4-one (2.7 g) is obtained as an oil following Method A and starting from isopropylamine (1.29 g, 21.8 mmol), 3-chloro-2-methylphenylisothiocyanate (4.0 g, 21.8 mmol) and methyl bromoacetate (3.33 g, 21.8 mmol). LC-MS: $t_R$=086 min, [M+1]$^+$=283, $^1$H NMR (CDCl$_3$): δ 7.48-7.44 (m, 1H), 7.30-7.23 (m, 1H), 7.10-7.06 (m, 1H), 3.51 (hept, J=6.2 Hz, 1H), 2.21 (s, 3H), 1.15 (d, J=6.2 Hz, 3H), 1.13 (d, J=6.2 Hz, 3H).

Scaffold 31

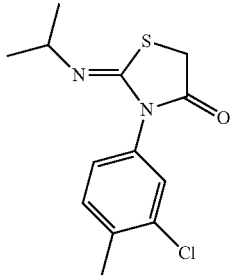 [SMILES: Cc1ccc(N2C(=O)CS/C2=N\C(C)C)cc1Cl]

2-[(Z)-Isopropylimino]-3-(3-chloro-4-methylphenyl)-thiazolidin-4-one (4.0 g) is obtained as pale yellow solid following Method A and starting from isopropylamine (1.72 g, 29.0 mmol), 3-chloro-4-methylphenylisothiocyanate (5.33 g, 29.0 mmol) and methyl bromoacetate (4.44 g, 29.0 mmol). LC-MS: $t_R$=0.80 min, [M+1]$^+$=283, $^1$H NMR (CDCl$_3$): δ 7.33 (s, 1H), 7.30-7.27 (m, 2H), 3.96 (s, 2H), 3.49 (hept, J=6.4 Hz, 1H), 2.40 (s, 3H), 1.14 (d, J=6.4 Hz, 6H).

Scaffold 32

2-[(Z)-Isopropylimino]-3-(3-trifluoromethylphenyl)-thiazolidin-4-one (2.77 g) is obtained as an oil following Method A and starting from isopropylamine (1.50 g, 25.4 mmol), 3-trifluoromethylphenylisothiocyanate (5.17 g, 25.4 mmol) and methyl bromoacetate (3.89 g, 25.4 mmol). LC-MS: $t_R$=0.88 min, [M+1]$^+$=303, $^1$H NMR (CDCl$_3$): δ 7.65-7.46 (m, 4H), 3.98 (s, 2H), 3.50 (hept, J=6.4 Hz, 1H), 1.13 (d, J=6.4 Hz, 6H).

Scaffold 33

2-[(Z)-Isopropylimino]-3-(3-chlorophenyl)-thiazolidin-4-one (1.0 g) is obtained as an oil following Method A and starting from isopropylamine (1.67 g, 28.3 mmol), 3-chlorophenylisothiocyanate (4.80 g, 28.3 mmol) and methyl bromoacetate (4.33 g, 28.3 mmol). LC-MS: $t_R$=0.77 min, [M+1]$^+$=269, $^1$H NMR (CDCl$_3$): δ 7.41-7.28 (m, 3H), 7.20-7.15 (m, 1H), 3.96 (s, 2H), 3.53-3.44 (m, 1H), 1.13 (d, 5.9 Hz, 6H).

Scaffold 34

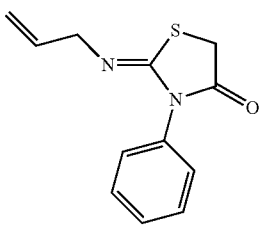 [SMILES: C=CC/N=C1\SCC(=O)N1c1ccccc1]

2-[(Z)-allyl]-3-phenyl-thiazolidin-4-one is obtained as a yellow powder following Method B and starting from aniline, chloroacetyl chloride and allylisothiocyanate. LC-MS: $t_R$=0.63 min, [M+1]$^+$=233, $^1$H NMR (CDCl$_3$): δ 7.52-7.38 (m, 3H), 7.31-7.25 (m, 2H), 5.96-5.82 (m, 1H), 5.20-5.06 (m, 2H), 4.01 (s, 2H), 3.99-3.95 (m, 2H).

Scaffold 35

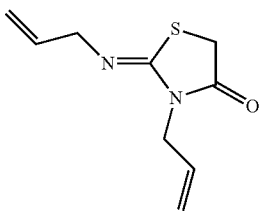

2-[(Z)-allylimino]-3-allyl-thiazolidin-4-one (3.12 g) is obtained as a pale yellow oil following Method A and starting from allylamine (1.15 g, 20.2 mmol), allylisothiocyanate (2.0 g, 20.2 mmol) and methyl bromoacetate (3.08 g, 20.2 mmol). LC-MS: $t_R$=0.66 min, [M+1]$^+$=197; $^1$H NMR (CDCl$_3$): δ 6.02-5.79 (m, 2H), 5.29-5.25 (m, 1H), 5.22-5.18 (m, 1H), 5.17-5.09 (m, 2H), 4.38-4.35 (m, 2H), 3.95 (dt, $J_d$=5.3 Hz, $J_t$=1.7 Hz, 2H), 3.83 (s, 2H).

Scaffold 36

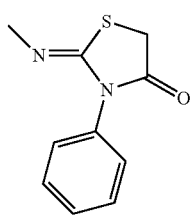

2-[(Z)-Methylimino]-3-phenyl-thiazolidin-4-one is obtained as a beige solid following Method B and starting from aniline, chloroacetyl chloride and methylisothiocyanate. LC-MS: $t_R$=0.37 min, [M+1]$^+$=207, $^1$H NMR (CDCl$_3$): δ 7.52-7.38 (m, 3H), 7.28-7.24 (m, 2H), 4.01 (s, 2H), 3.13 (s, 3H).

Scaffold 37

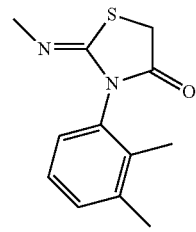 [SMILES: C/N=C1\SCC(=O)N1c1cccc(C)c1C]

2-[(Z)-Methylimino]-3-(2,3-dimethylphenyl)-thiazolidin-4-one is obtained as a pale orange solid following Method B and starting from 2,3-dimethylaniline, chloroacetyl chloride and methylisothiocyanate. LC-MS: $t_R$=0.59 min, [M+1]$^+$=235, $^1$H NMR (CDCl$_3$): δ 7.24-7.19 (m, 2H), 7.00-6.95 (m, 1H), 4.04 (s, 2H), 3.12 (s, 3H), 2.33 (s, 3H), 2.06 (s, 3H).

Example 1

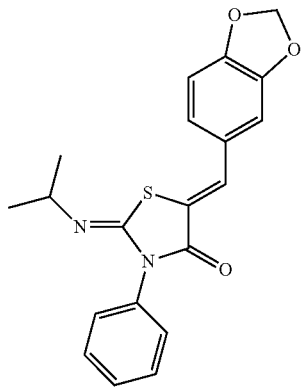 [SMILES: CC(C)/N=C1\S/C(=C\c2ccc3c(c2)OCO3)C(=O)N1c1ccccc1]

5-Benzo[1,3]dioxol-5-ylmeth-(Z)-ylidene-2-[(Z)-isopropylimino]-3-phenyl-thiazolidin-4-one is prepared as described in Method C.

LC-MS: $t_R$=1.06 min, [M+1]$^+$=367.

$^1$H NMR (CDCl$_3$): δ 7.70 (s, 1H), 7.52-7.32 (m, 5H), 7.12-7.07 (m, 2H), 6.92 (d, J=7.6 Hz, 1H), 6.06 (s, 2H), 3.61 (hept, J=6.1 Hz, 1H), 1.21 (d, J=6.4 Hz, 6H).

Example 2

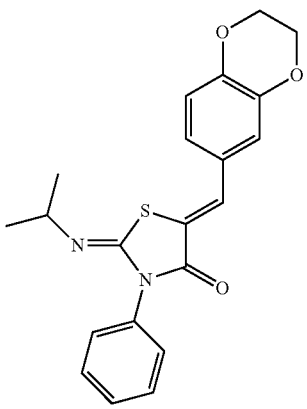 [SMILES: CC(C)/N=C1\S/C(=C\c2ccc3c(c2)OCCO3)C(=O)N1c1ccccc1]

5-(2,3-Dihydro-benzo[1,4]dioxin-6-ylmeth-(Z)-ylidene)-2-[(Z)-isopropylimino]-3-phenyl-thiazolidin-4-one is obtained starting from Scaffold 1 (19 mg, 0.08 mmol) and 2,3-dihydro-benzo[1,4]dioxine-6-carbaldehyde (26 mg, 0.16 mmol) following Method E.

LC-MS: $t_R$=1.05 min, $[M+1]^+$=381.

Example 3

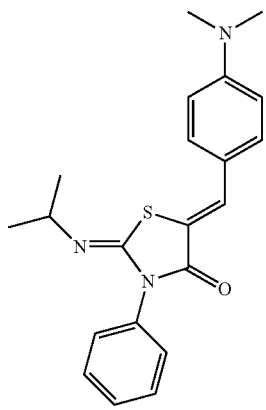 [SMILES: CC(C)/N=C1\S/C(=C\c2ccc(N(C)C)cc2)C(=O)N1c1ccccc1]

5-(4-Dimethylamino-benz-(Z)-ylidene)-2-[(Z)-isopropylimino]-3-phenyl-thiazolidin-4-one is obtained starting from Scaffold 1 (19 mg, 0.08 mmol) and 4-dimethylamino-benzaldehyde (24 mg, 0.16 mmol) following Method E. LC-MS: $t_R$=1.09 min, $[M+1]^+$=379.

Example 4

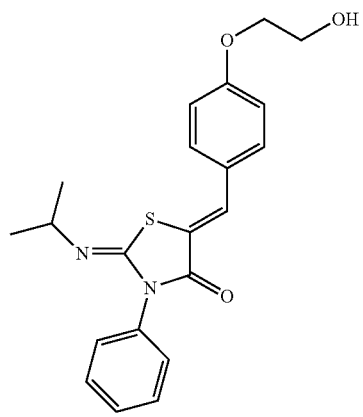 [SMILES: CC(C)/N=C1\S/C(=C\c2ccc(OCCO)cc2)C(=O)N1c1ccccc1]

5-[4-(2-Hydroxy-ethoxy)-benz-(Z)-ylidene]-2-[(Z)-isopropylimino]-3-phenyl-thiazolidin-4-one is prepared as described in Method D.

LC-MS: $t_R$=0.94 min, $[M+1]^+$=383.

$^1$H NMR (CDCl$_3$): δ 7.74 (s, 1H), 7.56-7.44 (m, 4H), 7.42-7.32 (m, 3H), 7.04-6.99 (m, 2H), 4.17-4.13 (m, 2H), 4.03-3.97 (m, 2H), 3.60 (hept, J=6.4 Hz, 1H), 2.01 (s br, 1H), 1.19 (d, J=6.4 Hz, 6H).

Example 5

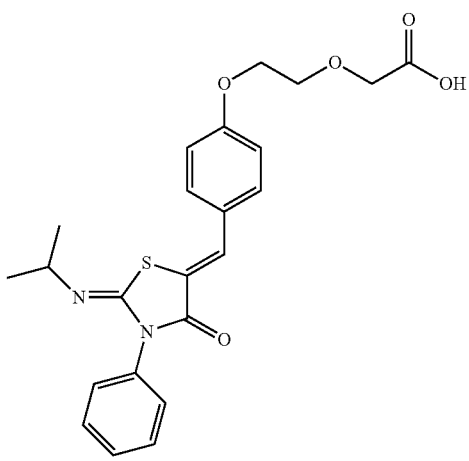 [SMILES: CC(C)/N=C1\S/C(=C\c2ccc(OCCOCC(=O)O)cc2)C(=O)N1c1ccccc1]

A mixture of 5-[4-(2-Hydroxy-ethoxy)-benz-(Z)-ylidene]-2-[(Z)-isopropylimino]-3-phenyl-thiazolidin-4-one (75 mg, 0.196 mmol, Example 4), K$_2$CO$_3$ (81 mg, 0.588 mmol), and methyl chloroacetate (250 L) in DMF (2 mL) is stirred at 60° C. for 96 h before it is diluted with EA (75 mL) and washed with 10% aq. citric acid (50 mL) and water (2×50 mL). The organic layer is evaporated and the resulting residue is purified by prep. TLC (heptane/EA 1:1) followed by crystallisation from a small amount of methanol to give {2-[4-(2-[(Z)-isopropylimino]-4-oxo-3-phenyl-thiazolidin-5-ylidenemethyl)-phenoxy]-ethoxy}-acetic acid. LC-MS: $t_R$=1.06 min, $[M+1]^+$=441. $^1$H NMR (CDCl$_3$): δ 7.73 (s, 1H), 7.55-7.44 (m, 4H), 7.42-7.32 (m, 3H), 7.03-6.98 (m, 2H), 4.55-4.50 (m, 2H), 4.29-4.25 (m, 2H), 3.83 (s, 2H), 3.60 (hept, J=6.4 Hz, 1H), 1.19 (d, J=6.4 Hz, 6H).

Example 6

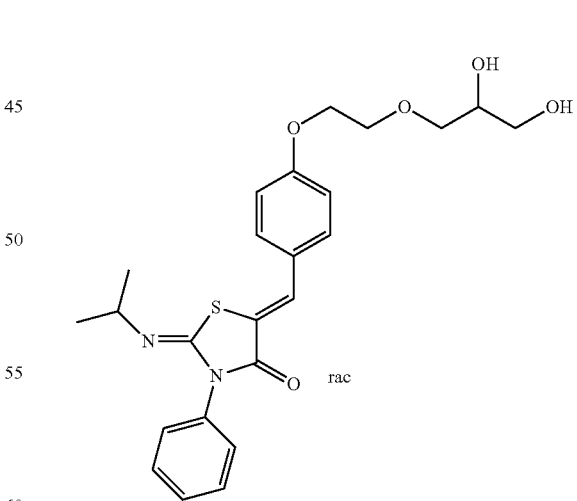

After purification on prep. TLC plates, rac-5-{4-[2-(2,3-dihydroxy-propoxy)-ethoxy]-benz-(Z)-ylidene}-2-[(Z)-isopropylimino]-3-phenyl-thiazolidin-4-one is obtained as a pale beige foam starting from Scaffold 1 (150 mg, 0.604 mmol) and rac-4-[2-(2,3-dihydroxy-propoxy)-ethoxy]-benzaldehyde (290 mg, 1.208 mmol) following Method D. LC- MS: $t_R$=0.99 min, [M+1]$^+$=471; $^1$H NMR (CDCl$_3$): δ 7.73 (s, 1H), 7.55-7.51 (m, 2H), 7.35-7.28 (m, 3H), 7.20-7.15 (m, 1H), 7.04-6.98 (m, 2H), 4.20 (t, J=4.7 Hz, 2H), 3.94-3.88 (m, 3H), 3.77-3.55 (m, 5H), 2.65 (s br, 1H), 2.19 (s, 3H), 2.08 (s br, 1H), 1.17 (d, J=6.4 Hz, 3H), 1.16 (d, J=6.4 Hz, 3H).

Example 7

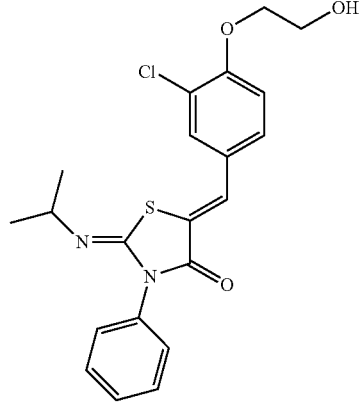 [SMILES: CC(C)/N=C1\S/C(=C\c2ccc(OCCO)c(Cl)c2)C(=O)N1c1ccccc1]

5-[3-Chloro-4-(2-hydroxy-ethoxy)-benz-(Z)-ylidene]-2-[(Z)-isopropylimino]-3-phenyl-thiazolidin-4-one is obtained as pale yellow powder starting from 3-chloro-4-(2-acetoxy-ethoxy)-benzaldehyde (311 mg, 1.28 mmol) and Scaffold 1 (150 mg, 0.64 mmol) following Method D. LC-MS: $t_R$=1.01 min, [M+1]$^+$=417; $^1$H NMR (CDCl$_3$): δ 7.654 (s, 1H), 7.61 (d, J=2.3 Hz, 1H), 7.51-7.32 (m, 6H), 7.03 (d, J=8.8 Hz, 1H), 4.24-4.20 (m, 2H), 4.06-4.01 (m, 2H), 3.60 (hept, J=6.4 Hz, 1H), 2.15 (s br, 1H), 1.19 (d, J=6.4 Hz, 6H).

Example 8

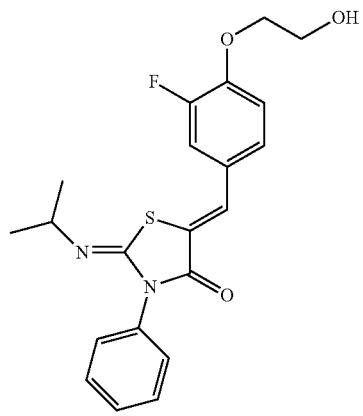 [SMILES: CC(C)/N=C1\S/C(=C\c2ccc(OCCO)c(F)c2)C(=O)N1c1ccccc1]

5-[3-Fluoro-4-(2-hydroxy-ethoxy)-benz-(Z)-ylidene]-2-[(Z)-isopropylimino]-3-phenyl-thiazolidin-4-one is prepared following Method D and starting from 4-(2-acetoxy-ethoxy)-3-fluoro-benzaldehyde (390 mg, 1.7 mmol) and Scaffold 1 (200 mg, 0.85 mmol). LC-MS: $t_R$=0.98 min, [M+1]$^+$=401; $^1$H NMR (CDCl$_3$): δ 7.66 (s, 1H), 7.51-7.28 (m, 7H), 7.06 (t, J=8.2 Hz, 1H), 4.24-4.20 (m, 2H), 4.06-4.00 (m, 2H), 3.60 (hept, J=6.4 Hz, 1H), 2.11 (t br, 1H), 1.19 (d, J=6.4 Hz, 6H).

Example 9

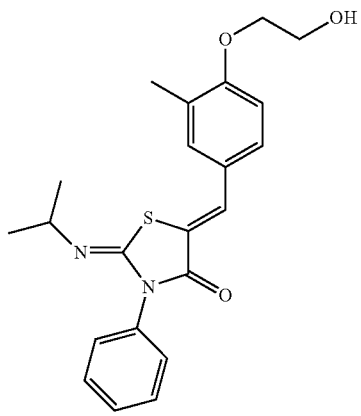 [SMILES: Cc1cc(/C=C2\S/C(=N\C(C)C)N(c3ccccc3)C2=O)ccc1OCCO]

5-[4-(2-Hydroxy-ethoxy)-3-methyl-benz-(Z)-ylidene]-2-[(Z)-isopropylimino]-3-phenyl-thiazolidin-4-one is obtained as an off-white powder starting from 4-(2-acetoxy-ethoxy)-3-methylbenzaldehyde (284 mg, 1.28 mmol) and Scaffold 1 (150 mg, 0.64 mmol) following Method D. LC-MS: $t_R$=0.98 min, [M+1]$^+$=397; $^1$H NMR (CDCl$_3$): δ 7.69 (s, 1H), 7.49-7.30 (m, 7H), 6.90 (d, J=8.2 Hz, 1H), 4.17-4.12 (m, 2H), 4.03-3.98 (m, 2H), 3.59 (hept, J=6,4 Hz, 1H), 2.30 (s, 3H), 1.95 (s br, 1H), 1.17 (d, J=6.4 Hz, 6H).

Example 10

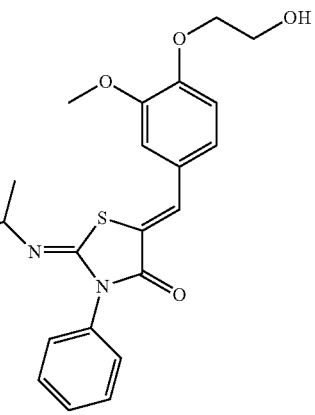

5-[4-(2-Hydroxy-ethoxy)-3-methoxy-benz-(Z)-ylidene]-2-[(Z)-isopropylimino]-3-phenyl-thiazolidin-4-one is obtained as a pale yellow powder starting from 4-(2-acetoxy-ethoxy)-3-methoxy-benzaldehyde (305 mg, 1.28 mmol) and Scaffold 1 (150 mg, 0.64 mmol) following Method D. LC-MS: $t_R$=0.95 min, [M+1]$^+$=413; $^1$H NMR (CDCl$_3$): δ 7.72 (s, 1H), 7.51-7.45 (m, 2H), 7.42-7.39 (m, 1H), 7.37-7.32 (m, 2H), 7.18 (dd, J=2.3, 8.2 Hz, 1H), 7.08 (d, J=2.3 Hz, 1H), 7.00 (d, J=8.2 Hz, 1H), 4.22-4.17 (m, 2H), 4.06-3.98 (m, 3H), 3.95 (s, 3H), 3.60 (hept, J=6.4 Hz, 1H), 1.22 (d, J=6.4 Hz, 3H), 1.19 (d, J=6.4 Hz, 3H).

Example 11

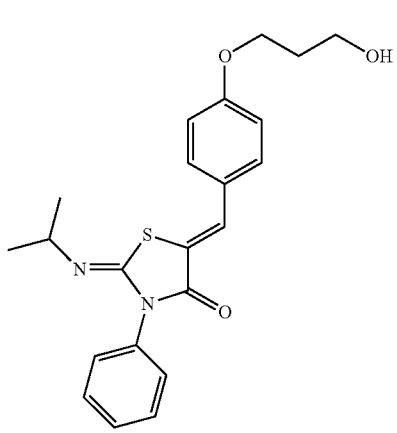 [SMILES: CC(C)/N=C1\S/C(=C\c2ccc(OCCCO)cc2)C(=O)N1c1ccccc1]

5-[4-(3-Hydroxy-propoxy)-benz-(Z)-ylidene]-2-[(Z)-isopropylimino]-3-phenyl-thiazolidin-4-one is obtained starting from Scaffold 1 (150 mg, 0.640 mmol) and 4-(3-hydroxy-propoxy)-benzaldehyde (173 mg, 0.960 mmol) following Method D. LC-MS: $t_R$=0.97 min, [M+1]$^+$=397. $^1$H NMR (CDCl$_3$): δ 7.73 (s, 1H), 7.55-7.33 (m, 7H), 7.02-6.97 (m, 2H), 4.19 (t, J=5.9 Hz, 2H), 3.89 (t, J=5.9 Hz, 2H), 3.60 (hept, J=6.4 Hz, 1H), 2.09 (p, J=5.9 Hz, 2H), 1.19 (d, J=6.4 Hz, 6H).

Example 12

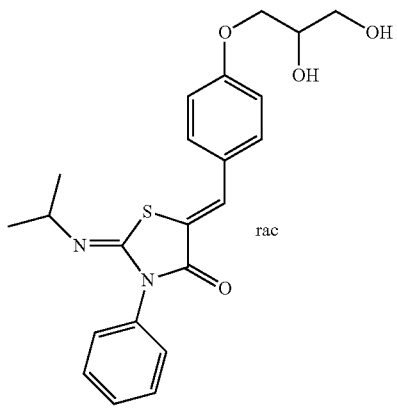 [SMILES: CC(C)/N=C1\S/C(=C\c2ccc(OCC(O)CO)cc2)C(=O)N1c1ccccc1]

rac-5-[4-(2,3-Dihydroxy-propoxy)-benz-(Z)-ylidene]-2-[(Z)-isopropylimino]-3-o-tolyl-thiazolidin-4-one is obtained as an off-white powder starting from rac-4-(2,3-dihydroxy-propoxy)-benzaldehyde (335 mg, 1.70 mmol) and Scaffold 1 (200 mg, 0.85 mmol) following Method D. LC-MS: $t_R$=0.86 min, [M+1]$^+$=413. $^1$H NMR (CDCl$_3$): δ 7.73 (s, 1H), 7.55-7.45 (m, 4H), 7.43-7.32 (m, 3H), 7.03-6.99 (m, 2H), 4.16-4.10 (m, 3H), 3.91-3.84 (m, 1H), 3.81-3.74 (m, 1H), 3.60 (hept, J=6.4 Hz, 1H), 2.56 (s br, 1H), 1.95 (s br, 1H); 1.19 (d, J=6.4 Hz, 6H).

Example 13

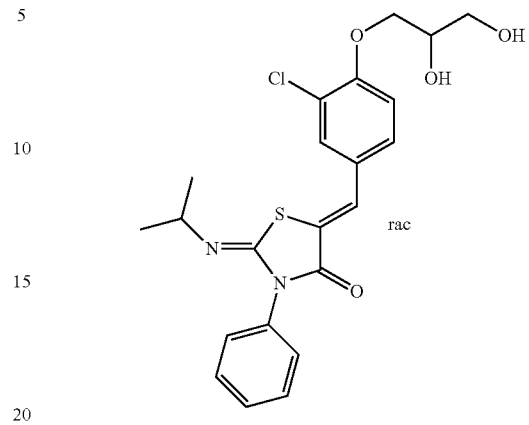

rac-5-[3-Chloro-4-(2,3-dihydroxy-propoxy)-benz-(Z)-ylidene]-2-[(Z)-isopropylimino]-3-phenyl-thiazolidin-4-one is obtained as pale olive powder starting from rac-4-(2,3-dihydroxy-propoxy)-3-chloro-benzaldehyde (295 mg, 1.28 mmol) and Scaffold 1 (150 mg, 0.64 mmol) following Method D. LC-MS: $t_R$=0.94 min, [M+1]$^+$=447. $^1$H NMR (CDCl$_3$): δ 7.64 (s, 1H), 7.59 (d, J=2.3 Hz, 1H), 7.50-7.30 (m, 6H), 7.01 (d, J=8.2 Hz, 1H), 4.25-4.13 (m, 3H), 3.92-3.80 (m, 2H), 3.59 (hept, J=6.4 Hz, 1H), 2.70 (s br, 1H), 2.05 (s br, 1H), 1.18 (d, J=6.4 Hz, 6H).

Example 14

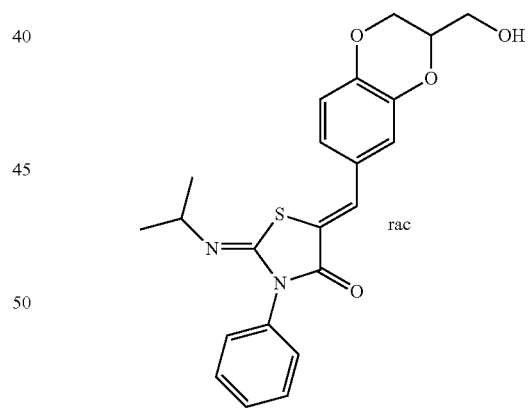

rac-5-(3-Hydroxymethyl-2,3-dihydro-benzo[1,4]dioxin-6-ylmeth-(Z)-ylene)-2-[(Z)-isopropylimino-3-phenyl-thiazolidin-4-one is obtained as almost colourless crystals (EA/methanol) starting from rac-2-hydroxymethyl-2,3-dihydro-benzo[1,4]dioxine-6-carbaldehyde (210 mg, 1.08 mmol) and Scaffold 1 (150 mg, 0.64 mmol) following Method D. LC-MS: $t_R$=0.97 min, [M+1]$^+$=411. $^1$H NMR (CDCl$_3$): δ 7.58 (s, 1H), 7.42-7.35 (m, 2H), 7.33-7.24 (m, 3H), 7.06-7.01 (m, 2H), 6.92-6.89 (m, 1H), 4.42-4.35 (m, 1H), 4.30-4.23 (m, 3H), 4.03 (dd, J=7.0, 11.1, 1H), 3.51 (hept, J=6.4 Hz, 1H), 1.10 (d, J=6.4 Hz, 6H).

Examples 15 to 25
Starting from Scaffold 2, the following examples are prepared:
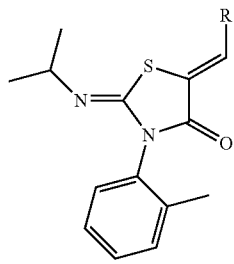
| Example | R | Method | Scale (mmol) | LC-MS $t_R$ | $[M+1]^+$ |
|---|---|---|---|---|---|
| 15 | benzo[1,3]dioxol-5-yl | C | 0.604 | 1.10 | 381 |
| 16 | 2,3-dihydrobenzo[1,4]dioxin-6-yl | E | 0.200 | 1.09 | 395 |
| 17 | 4-(dimethylamino)phenyl | C | 0.604 | 1.03 | 380 |
| 18 | 4-(2-hydroxyethoxy)phenyl | D | 0.400 | 0.98 | 397 |
| 19 | 4-(2-(2,3-dihydroxypropoxy)ethoxy)phenyl | D | 0.604 | 0.91 | 471 |

-continued
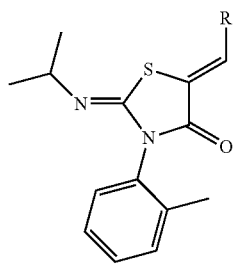
| Example | R | Method | Scale (mmol) | LC-MS $t_R$ | $[M+1]^+$ |
|---|---|---|---|---|---|
| 20 | 2-chloro-4-(2-hydroxyethoxy)phenyl | D | 0.604 | 1.04 | 431 |
| 21 | 2-methyl-4-(2-hydroxyethoxy)phenyl | D | 0.604 | 1.02 | 411 |
| 22 | 2-methoxy-4-(2-hydroxyethoxy)phenyl | D | 0.604 | 0.98 | 427 |
| 23 | 4-(3-hydroxypropoxy)phenyl | D | 0.604 | 1.01 | 411 |
| 24 | 2-chloro-4-(2,3-dihydroxypropoxy)phenyl | D | 0.604 | 0.96 | 461 |

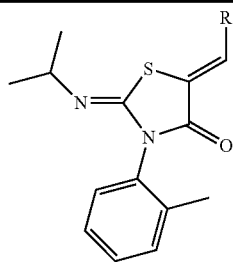

| Example | R | Method | Scale (mmol) | LC-MS $t_R$ | [M + 1]$^+$ |
|---|---|---|---|---|---|
| 25 | HO— (2,3-dihydro-1,4-benzodioxin-2-yl)methanol group | D | 0.650 | 1.01 | 425 |

Example 15

$^1$H NMR (CDCl$_3$): δ 7.69 (s, 1H), 7.34-7.27 (m, 3H), 7.20-7.14 (m, 1H), 7.12-7.07 (m, 2H), 6.91 (d, J=7.6 Hz, 1H), 6.06 (s, 2H), 3.58 (hept, J=6.4 Hz, 1H), 2.19 (s, 3H), 1.18 (d, J=5.9 Hz, 3H), 1.17 (d, J=5.9 Hz, 3H).

Example 20

$^1$H NMR (CDCl$_3$): δ 7.65 (s, 1H), 7.62 (d, J=2.3 Hz, 1H), 7.45 (dd, J=2.3, 8.2 Hz, 1H), 7.36-7.29 (m, 3H), 7.20-7.15 (m, 1H), 7.03 (d, J=8.8 Hz, 1H), 4.24-4.20 (m, 2H), 4.07-4.01 (m, 2H), 3.59 (hept, J=5.9 Hz, 1H), 2.18 (s, 3H), 2.14 (s br, 1H), 1.18 (d, J=5.9 Hz, 3H), 1.16 (d, J=5.9 Hz, 3H).

Example 23

$^1$H NMR (CDCl$_3$): δ 7.73 (s, 1H), 7.55-7.50 (m, 2H), 7.35-7.27 (m, 3H), 7.20-7.15 (m, 1H), 7.02-6.98 (m, 2H), 4.20 (t, J=5.9 Hz, 2H), 3.88 (t, J=5.9 Hz, 2H), 3.58 (hept, J=6.4 Hz, 1H), 2.18 (s, 3H), 2.09 (p, J=5.9 Hz, 2H), 1.17 (d, J=6.4 Hz, 3H), 1.16 (d, J=6.4 Hz, 3H).

Example 24

$^1$H NMR (CDCl$_3$): δ 7.63 8s, 1H), 7.59 8d, J=2.3 Hz, 1H), 7.43 (dd, J=2.3, 8.8 Hz, 1H), 7.35-7.26 (m, 3H), 7.17-7.13 (m, 1H), 7.01 (d, J=8.8 Hz, 1H), 4.24-4.13 (m, 3H), 3.91-3.79 (m, 2H), 3.57 (hept, J=5.9 Hz, 1H), 2.74 (s br, 1H), 2.16 (s, 3H), 1.17 (d, J=5.9 Hz, 3H), 2.15 (d, J=5.9 Hz, 3H).

Examples 26 to 31

Starting from Scaffold 3, the following examples are prepared:

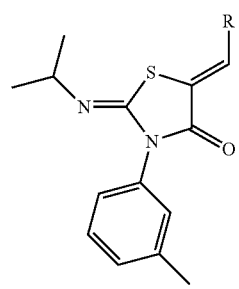

| Example | R | Method | Scale (mmol) | LC-MS $t_R$ | [M + 1]$^+$ |
|---|---|---|---|---|---|
| 26 | 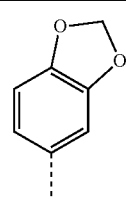 | E | 0.200 | 1.08 | 381 |
| 27 | 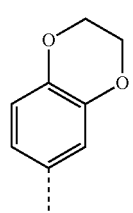 | E | 0.200 | 1.08 | 395 |

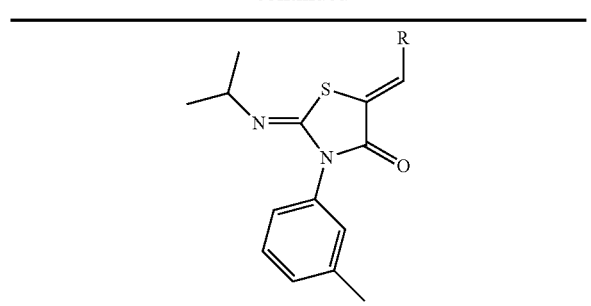
| Example | R | Method | Scale (mmol) | LC-MS $t_R$ | [M+1]$^+$ |
|---|---|---|---|---|---|
| 28 | 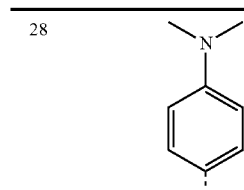 | E | 0.200 | 1.01 | 380 |
| 29 | 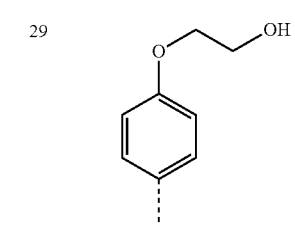 | D | 0.400 | 0.97 | 397 |
| 30 | 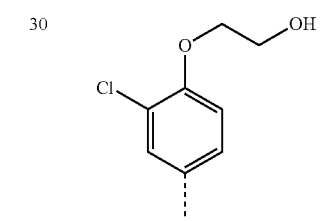 | D | 0.604 | 1.04 | 431 |
| 31 | 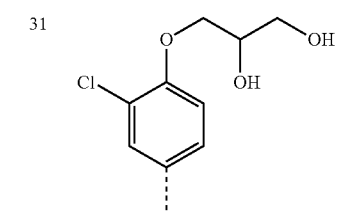 | D | 0.604 | 0.97 | 461 |
Example 31
$^1$H NMR (CDCl$_3$) ∈ 7.64 (s, 1H), 7.60 (d, J=2.3 Hz, 1H), 7.44 (dd, J=2.3, 8.8 Hz, 1H), 7.39-7.33 (m, 1H), 7.23-7.19 (m, 1H), 7.15-7.10 (m, 2H), 7.02 (d, J=8.8 Hz, 1H), 4.25-4.15 (m, 3H), 3.93-3.80 (m, 2H), 3.60 (hept, J=6.4 Hz, 1H), 2.75 (s br, 1H), 2.41 (s, 3H), 1.85 (s br, 1H), 1.21 (d, J=6.4 Hz, 6H).
Examples 32 to 36
Starting from Scaffold 4, the following examples have been prepared:
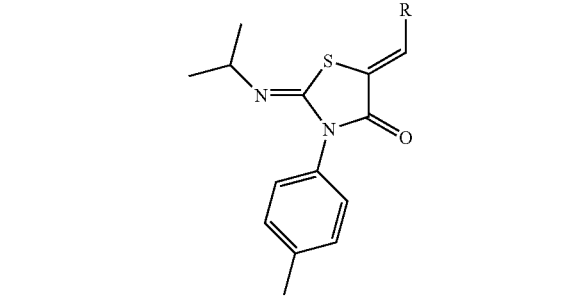
| Example | R | Method | Scale (mmol) | LC-MS $t_R$ | [M+1]$^+$ |
|---|---|---|---|---|---|
| 32 | 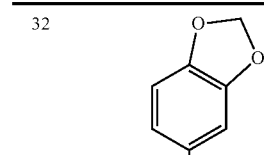 | E | 0.200 | 1.09 | 381 |
| 33 | 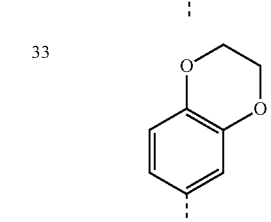 | E | 0.200 | 1.09 | 395 |
| 34 | 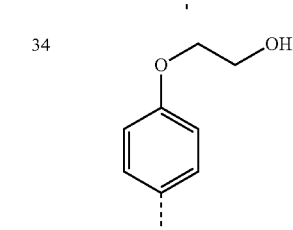 | D | 0.400 | 0.97 | 397 |
| 35 | 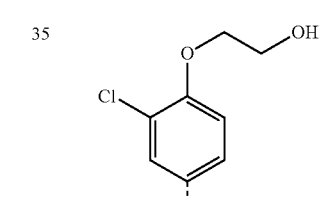 | D | 0.604 | 1.05 | 431 |
| 36 | 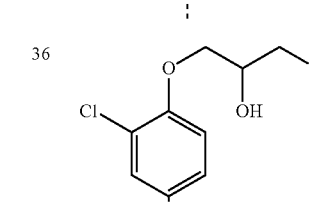 | D | 0.604 | 0.98 | 461 |
Example 35
$^1$H NMR (CDCl$_3$): δ 7.64 (s, 1H), 7.60 (d, J=2.3 Hz, 1H), 7.44 (dd, J=2.3, 8.2 Hz, 1H), 7.30-7.19 (m, 4H), 7.02 (d, J=8.2 Hz, 1H), 4.23-4.19 (m, 2H), 4.07-4.00 (m, 2H), 3.59 (hept, J=6.4 Hz, 1H), 2.40 (s, 3H), 2.14 (s br, 1H), 1.19 (d, J=6.4 Hz, 6H).

Examples 37 to 47
Starting from Scaffold 5, the following examples have been prepared:
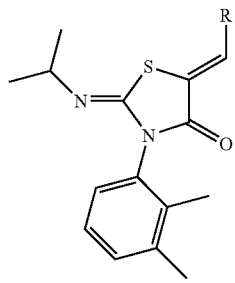
| Example | R | Method | Scale (mmol) | LC-MS $t_R$ | $[M + 1]^+$ |
|---|---|---|---|---|---|
| 37 | benzo[1,3]dioxole | E | 0.200 | 1.11 | 395 |
| 38 | 2,3-dihydrobenzo[1,4]dioxine | E | 0.200 | 1.11 | 409 |
| 39 | 4-(dimethylamino)phenyl | E | 0.200 | 1.05 | 394 |
| 40 | 4-(2-hydroxyethoxy)phenyl | D | 0.763 | 0.99 | 411 |
| 41 | 4-(2-(2,3-dihydroxypropoxy)ethoxy)phenyl | D | 0.572 | 0.93 | 485 |

-continued
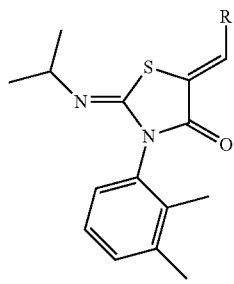
| Example | R | Method | Scale (mmol) | LC-MS $t_R$ | $[M+1]^+$ |
|---|---|---|---|---|---|
| 42 | 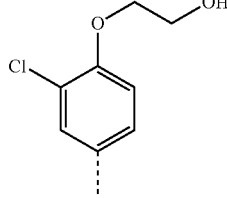 | D | 0.572 | 1.06 | 445 |
| 43 | 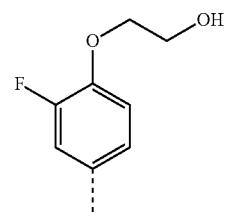 | D | 0.572 | 1.03 | 429 |
| 44 | 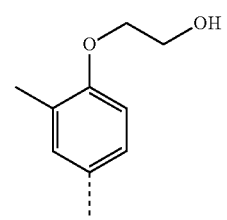 | D | 0.572 | 1.03 | 425 |
| 45 | 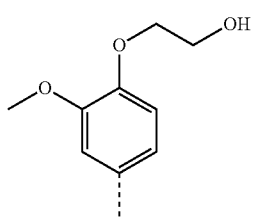 | D | 0.572 | 1.00 | 441 |

-continued

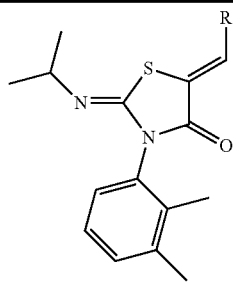

| Example | R | Method | Scale (mmol) | LC-MS $t_R$ | $[M + 1]^+$ |
|---|---|---|---|---|---|
| 46 | ![structure with Cl, O, OH, OH] | D | 0.572 | 0.98 | 475 |
| 47 | ![benzodioxane with HO-CH2] | D | 0.650 | 1.00 | 439 |

Example 40

$^1$H NMR (CDCl$_3$): δ 7.73 (s, 1H), 7.56-7.51 (m, 2H), 7.24-7.18 (m, 2H), 7.06-7.00 (m, 3H), 4.18-4.14 (m, 2H), 4.04-3.98 (m, 2H), 3.50 (hep, J=6.4 Hz, 1H), 2.35 (s, 3H), 2.05 (s, 3H), 2.00 (s br, 1H), 1.18 (d, J=6.4 Hz, 3H), 1.17 (d, J=6.4 Hz, 3H).

Example 47

$^1$H NMR (CDCl$_3$): δ 7.57 (s, 1H), 7.17-7.00 (m, 4H), 6.97-6.85 (m, 2H), 4.30-4.18 (m, 2H), 4.11-4.03 (m, 1H), 3.86-3.70 (m, 2H), 3.49 (hept, J=6.4 Hz, 1H), 2.26 (s, 3H), 1.95 (s, 3H), 1.07 (d, J=6.4 Hz, 6H).

Examples 48 and 49

Starting from Scaffold 6, the following examples are prepared:

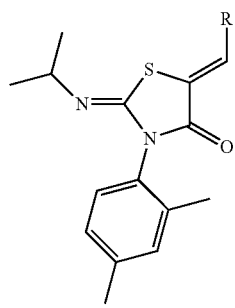

| Example | R | Method | Scale (mmol) | LC-MS $t_R$ | $[M + 1]^+$ |
|---|---|---|---|---|---|
| 48 | 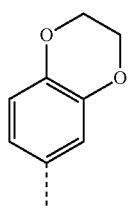 | E | 0.200 | 1.12 | 409 |

-continued

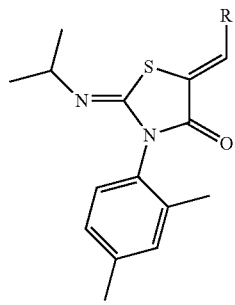

| Example | R | Method | Scale (mmol) | LC-MS $t_R$ | $[M + 1]^+$ |
|---|---|---|---|---|---|
| 49 | (structure: 4-(2-hydroxyethoxy)phenyl) | D | 0.762 | 1.00 | 411 |

Example 48

$^1$H NMR (CDCl$_3$): δ 7.72 (s, 1H), 7.56-7.50 (m, 2H), 7.14-6.98 (m, 5H), 4.17-4.12 (m, 2H), 4.02-3.96 (m, 2H), 3.58 (hept, J=6.2 Hz, 1H), 2.37 (s, 3H), 2.14 (s, 3H), 2.04 (s br, 1H), 1.17 (d, J=6.2 Hz, 3H), 1.16 (d, J=6.2 Hz, 3H).

Examples 50 to 51

Starting from Scaffold 7, the following examples are prepared:

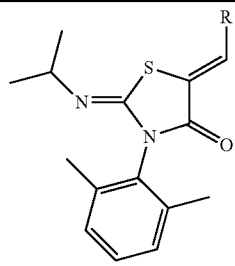

| Example | R | Method | Scale (mmol) | LC-MS $t_R$ | $[M + 1]^+$ |
|---|---|---|---|---|---|
| 50 | (2,3-dihydro-1,4-benzodioxin-6-yl) | E | 0.200 | 1.13 | 409 |

-continued

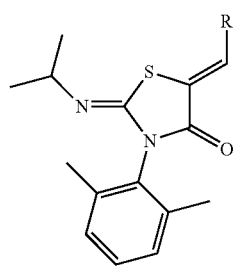

| Example | R | Method | Scale (mmol) | LC-MS $t_R$ | $[M + 1]^+$ |
|---|---|---|---|---|---|
| 51 | (4-(2-hydroxyethoxy)phenyl) | D | 0.762 | 1.02 | 411 |

Example 51

$^1$H NMR (CDCl$_3$): δ 7.73 (s, 1H), 7.57-7.52 (m, 2H), 7.27-7.21 (m, 1H), 7.17-7.12 (m, 2H), 7.04-6.99 (m, 2H), 4.18-4.13 (m, 2H), 4.03-3.98 (m, 2H), 3.57 (hept, J=6.1 Hz, 1H), 2.15 (s, 6H), 2.01 (s br, 1H), 1.16 (d, J=6.4 Hz, 6H).

Examples 52 to 57

Starting from Scaffold 8, the following examples are prepared:

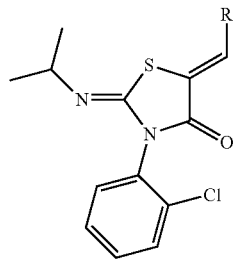

| Example | R | Method | Scale (mmol) | LC-MS $t_R$ | $[M + 1]^+$ |
|---|---|---|---|---|---|
| 52 | (1,3-benzodioxol-5-yl) | E | 0.200 | 1.11 | 401 |

-continued

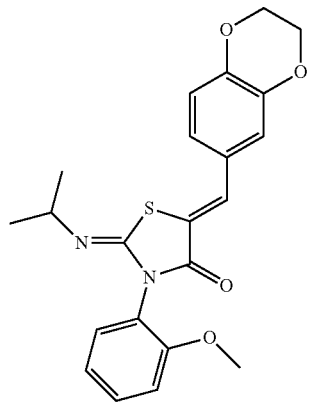 [SMILES: COc1ccccc1N1C(=O)/C(=C/c2ccc3c(c2)OCCO3)S/C1=N\C(C)C]

| Example | R | Method | Scale (mmol) | LC-MS $t_R$ | $[M+1]^+$ |
|---|---|---|---|---|---|
| 53 | (2,3-dihydro-benzo[1,4]dioxin-6-yl) | E | 0.200 | 1.11 | 415 |
| 54 | (4-dimethylaminophenyl) | E | 0.200 | 1.09 | 400 |
| 55 | (4-(2-hydroxyethoxy)phenyl) | D | 0.744 | 0.99 | 417 |
| 56 | (3-chloro-4-(2-hydroxyethoxy)phenyl) | D | 0.558 | 1.05 | 451 |
| 57 | (3-chloro-4-(2,3-dihydroxypropoxy)phenyl) | D | 0.558 | 0.98 | 481 |

Example 55

$^1$H NMR (CDCl$_3$): δ 7.74 (s, 1H), 7.56-7.50 (m, 3H), 7.41-7.32 (m, 3H), 7.04-7.00 (m, 2H), 4.18-4.13 (m, 2H), 4.04-3.98 (m, 2H), 3.58 (hept, J=6.1 Hz, 1H), 2.01 (s br, 1H), 1.17 (d, J=5.9 Hz, 3H), 1.16 (d, J=6.4 Hz, 3H).

Example 58

5-(2,3-Dihydro-benzo[1,4]dioxin-6-ylmeth-(Z)-ylidene)-2-[(Z)-isopropylimino]-3-(2-methoxyphenyl)-thiazolidin-4-one is obtained starting from Scaffold 9 (53 mg, 0.200 mmol) and 2,3-dihydro-benzo[1,4]dioxine-6-carbaldehyde (49 mg, 0.300 mmol) following Method C. LC-MS: $t_R$=1.03 min, [M+1]$^+$=411.

Examples 58 to 60

Starting from Scaffold 9, the following examples are prepared:

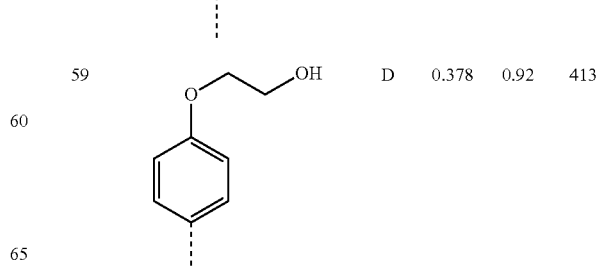

| Example | R | Method | Scale (mmol) | LC-MS $t_R$ | $[M+1]^+$ |
|---|---|---|---|---|---|
| 58 | (2,3-dihydro-benzo[1,4]dioxin-6-yl) | C | 0.200 | 1.03 | 411 |
| 59 | (4-(2-hydroxyethoxy)phenyl) | D | 0.378 | 0.92 | 413 |

Example 60

| Example | R | Method | Scale (mmol) | LC-MS $t_R$ | LC-MS $[M + 1]^+$ |
|---|---|---|---|---|---|
| 60 | 2-chloro-4-(2-hydroxyethoxy)phenyl | D | 0.567 | 0.99 | 447 |

Example 60

$^1$H NMR (CDCl$_3$): δ 7.55 (s, 1H), 7.52 (d, J=2.3 Hz, 1H), 7.38-7.29 (m, 2H), 7.15 (dd, J=1.8, 7.6 Hz, 1H), 7.00-6.92 (m, 3H), 4.15-4.11 (m, 2H), 3.98-3.93 (m, 2H), 3.72 (s, 3H), 3.50 (hept, J=6.4 Hz, 1H), 2.08 (s br, 1H), 1.09 (d, J=6.4 Hz, 3H), 1.08 (d, J=6.4 Hz, 3H).

Examples 61 and 62

Starting from Scaffold 10, the following examples are prepared:

| Example | R | Method | Scale (mmol) | LC-MS $t_R$ | LC-MS $[M + 1]^+$ |
|---|---|---|---|---|---|
| 61 | 2,3-dihydro-1,4-benzodioxin-6-yl | E | 0.200 | 1.06 | 411 |
| 62 | 4-(2-hydroxyethoxy)phenyl | D | 0.380 | 0.95 | 413 |

Example 63 to 65

Starting from Scaffold 11, the following examples are prepared:

| Example | R | Method | Scale (mmol) | LC-MS $t_R$ | LC-MS $[M + 1]^+$ |
|---|---|---|---|---|---|
| 63 | 2,3-dihydro-1,4-benzodioxin-6-yl | E | 0.200 | 1.05 | 411 |

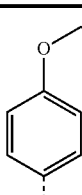
| Example | R | Method | Scale (mmol) | LC-MS $t_R$ | [M + 1]$^+$ |
|---|---|---|---|---|---|
| 64 | 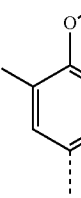 | D | 0.380 | 0.93 | 413 |
| 65 | 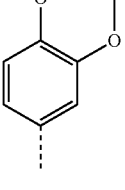 | D | 0.567 | 0.99 | 447 |
Example 66 to 71
Starting from Scaffold 12, the following examples are prepared:
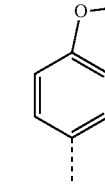
| Example | R | Method | Scale (mmol) | LC-MS $t_R$ | [M + 1]$^+$ |
|---|---|---|---|---|---|
| 66 | 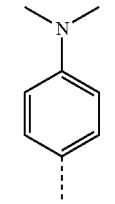 | E | 0.200 | 1.07 | 331 |
| 67 | 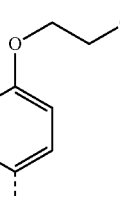 | E | 0.080 | 1.05 | 345 |
| 68 | 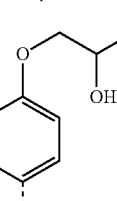 | C | 20.0 | 0.99 | 330.2 |
| 69 | 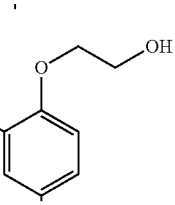 | D | 0.757 | 0.94 | 347 |
| 70 | | D | 0.756 | 1.02 | 381 |
| 71 | | D | 0.756 | 0.94 | 411 |
Example 68
$^1$H NMR (D$_6$-DMSO): δ 7.55 (s, 1H), 7.46-7.42 (m, 2H), 6.82-6.76 (m, 2H), 5.90-5.76 (m, 1H), 5.13-5.02 (m, 2H), 4.36-4.27 (m, 2H), 3.50 (hept, J=6.0 Hz, 1H), 2.99 (s, 6H), 1.16 (d, J=5.9 Hz, 6H).

Example 69

$^1$H NMR (CDCl$_3$): δ 7.66 (s, 1H), 7.51-7.46 (m, 2H), 7.01-6.96 (m, 2H), 5.96-5.83 (m, 1H), 5.28-5.14 (m, 2H), 4.49-4.44 (m, 2H), 4.16-4.12 (m, 2H), 4.03-3.96 (m, 2H), 3.55 (hept, J=6.1 Hz, 1H), 2.01 (t br, J=5 Hz, 1H), 1.24 (d, J=5.9 Hz, 6H).

Examples 72 to 77

Starting from Scaffold 13, the following examples are prepared:

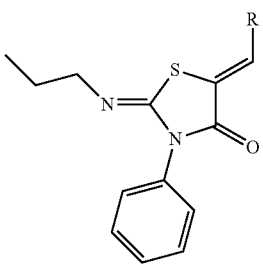

| Example | R | Method | Scale (mmol) | LC-MS $t_R$ | [M + 1]$^+$ |
|---|---|---|---|---|---|
| 72 | benzo[1,3]dioxol-5-yl | C | 0.640 | 1.06 | 367 |
| 73 | 2,3-dihydrobenzo[1,4]dioxin-6-yl | C | 0.333 | 1.05 | 381 |
| 74 | 4-(2-hydroxyethoxy)phenyl | D | 0.854 | 0.95 | 383 |
| 75 | 2-chloro-4-(2-hydroxyethoxy)phenyl | D | 1.067 | 1.01 | 417 |
| 76 | 2-methyl-4-(2-hydroxyethoxy)phenyl | D | 1.067 | 0.97 | 397 |
| 77 | 2-chloro-4-(2,3-dihydroxypropoxy)phenyl | D | 0.640 | 0.94 | 447 |

Example 74

$^1$H NMR (CDCl$_3$): δ 7.74 (s, 1H), 7.56-7.44 (m, 4H), 7.43-7.32 (m, 3H), 7.03-6.98 (m, 2H), 4.18-4.13 (m, 2H), 4.04-3.96 (m, 2H), 3.38 (t, J=6.6 Hz, 2H), 2.01 (s br, 1H), 1.72-1.59 (m, 2H), 0.95 (t, J=7.6 Hz, 3H).

Example 76

$^1$H NMR (CDCl$_3$): δ 7.72 (s, 1H), 7.53-7.33 (m, 7H), 6.93 (d, J=8.8 Hz, 1H), 4.19-4.15 (m, 2H), 4.06-4.00 (m, 2H), 3.40 (t, J=7.0 Hz, 2H), 2.33 (s, 3H), 1.98 (t br, J=6 Hz, 1H), 1.67 (hex, J=7.0 Hz, 2H), 0.96 (t, J=7.0 Hz, 3H).

Example 78 to 86

Starting from Scaffold 14, the following examples are prepared:

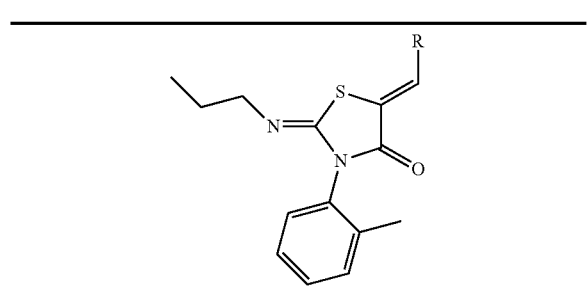
| Example | R | Method | Scale (mmol) | LC-MS $t_R$ | [M+1]+ |
|---|---|---|---|---|---|
| 78 | 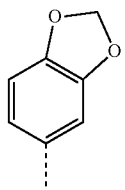 | C | 0.805 | 1.08 | 381 |
| 79 | 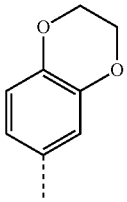 | C | 0.805 | 1.08 | 395 |
| 80 | 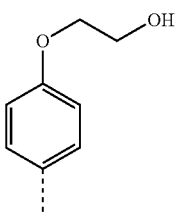 | D | 0.805 | 0.96 | 397 |
| 81 | 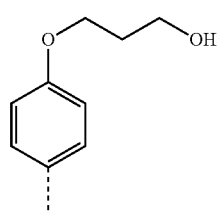 | D | 0.427 | 0.99 | 411 |
| 82 | 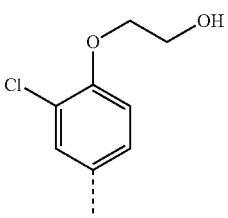 | D | 0.805 | 1.03 | 431 |
| 83 | 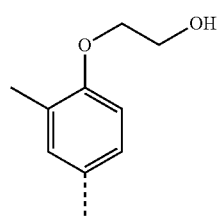 | D | 0.604 | 1.01 | 411 |
-continued
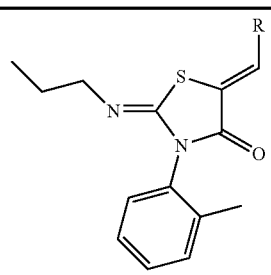
| Example | R | Method | Scale (mmol) | LC-MS $t_R$ | [M+1]+ |
|---|---|---|---|---|---|
| 84 | 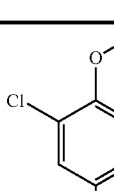 | D | 0.604 | 0.96 | 461 |
| 85 | (S)-isomer | F | 0.351 | 0.96 | 461 |
| 86 | (R)-isomer | F | 0.314 | 0.96 | 461 |
Example 80
$^1$H-NMR (CDCl$_3$): δ 7.74 (s, 1H), 7.57-7.52 (m, 2H), 7.36-7.28 (m, 3H), 7.20-7.16 (m, 1H), 7.05-7.00 (m, 2H), 4.18-4.14 (m, 2H), 4.04-3.98 (m, 2H), 3.46-3.30 (m, 2H), 2.20 (s, 3H), 2.00 (s br, 1H), 1.68-1.56 (m, 2H), 0.93 (t, J=7.0 Hz, 3H).
Example 81
$^1$H NMR (CDCl$_3$): δ 7.74 (s, 1H), 7.56-7.51 (m, 2H), 7.35-7.28 (m, 3H), 7.20-7.15 (m, 1H), 7.03-6.98 (m, 2H), 4.20 (t, J=5.9 Hz, 2H), 3.89 (t, J=5.9 Hz, 2H), 3.49-3.30 (m, 2H), 2.20 (s, 3H), 2.15-2.03 (m, 2H), 1.68-1.55 (m, 2H), 0.92 (t, J=7.6 HZ, 3H).
Example 86
$^1$H NMR (CDCl$_3$): δ 7.66 (s, 1H), 7.62 (d, J=2.3 Hz, 1H), 7.47 (dd, J=2.3, 8.8 Hz, 1H), 7.36-7.28 (m, 3H), 7.21-7.16 (m, 1H), 7.05 (d, J=8.8 Hz, 1H), 4.25-4.16 (m, 3H), 3.94-3.82 (m, 2H), 3.45-3.30 (m, 2H), 2.72 (d, J=4.1 Hz, 1H), 2.20 (s, 3H), 2.07 (t, J=6.2 Hz, 1H), 1.63 (hex, J=7.0 Hz, 2H), 0.93 (t, J=7.0 Hz, 3H).

Example 87 to 95
Starting from Scaffold 15, the following examples are prepared:
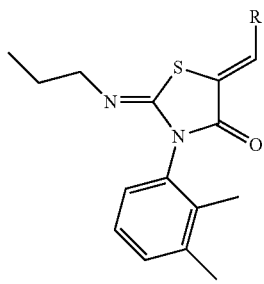
| Example | R | Method | Scale (mmol) | LC-MS $t_R$ | $[M+1]^+$ |
|---|---|---|---|---|---|
| 87 | benzo[1,3]dioxole | C | 0.762 | 1.09 | 395 |
| 88 | 2,3-dihydrobenzo[1,4]dioxine | C | 0.762 | 1.10 | 409 |
| 89 | 4-(2-hydroxyethoxy)phenyl | D | 0.762 | 0.98 | 411 |
| 90 | 4-(2,3-dihydroxypropoxyethoxy)phenyl | D | 0.762 | 0.92 | 485 |
| 91 | 2-chloro-4-(2-hydroxyethoxy)phenyl | D | 1.906 | 1.05 | 445 |

-continued

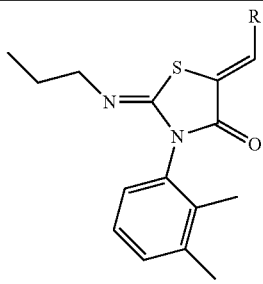

| Example | R | Method | Scale (mmol) | LC-MS $t_R$ | [M + 1]$^+$ |
|---|---|---|---|---|---|
| 92 | (2-methylphenoxy)ethanol group | D | 0.572 | 1.02 | 425 |
| 93 | (2-methoxyphenoxy)ethanol group | D | 0.762 | 0.99 | 441 |
| 94 | (phenoxy)propane-2,3-diol group | D | 0.762 | 0.90 | 441 |
| 95 | (2-chlorophenoxy)propane-2,3-diol group | D | 0.572 | 0.98 | 475 |

Example 87

$^1$H NMR (CDCl$_3$): δ 7.69 (s, 1H), 7.23-7.18 (m, 2H), 7.13-7.08 (m, 2H), 7.04-7.00 (m, 1H), 6.93-6.90 (m, 1H), 6.06 (s, 2H), 3.46-3.30 (m, 2H), 2.34 (s, 3H), 2.07 (s, 3H), 1.70-1.55 (m, 2H), 0.92 8t, J=7.6 Hz, 3H).

Example 89

$^1$H NMR (CDCl$_3$): δ 7.74 (s, 1H), 7.57-7.52 (m, 2H), 7.23-7.20 (m, 2H), 7.05-7.00 (m, 3H), 4.18-4.14 (m, 2H), 4.03-3.98 (m, 2H), 3.48-3.30 (m, 2H), 2.35 (s, 3H), 2.07 (s, 3H), 1.67-1.57 (m, 2H), 0.93 (t, J=7.6 Hz, 3H).

Examples 96 and 97

Starting from Scaffold 16 the following examples are prepared:

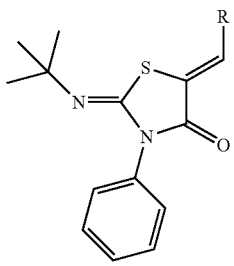

| Example | R | Method | Scale (mmol) | LC-MS $t_R$ | [M + 1]+ |
|---|---|---|---|---|---|
| 96 | (benzodioxine) | C | 0.08 | 1.11 | 395 |
| 97 | (2-chloro-4-(2-hydroxyethoxy)phenyl) | D | 0.604 | 1.08 | 431 |

Example 98 to 101

Starting from Scaffold 17, the following examples are prepared:

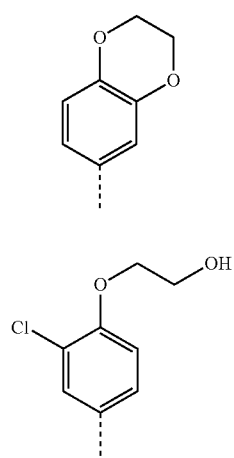

| Example | R | Method | Scale (mmol) | LC-MS $t_R$ | [M + 1]++ |
|---|---|---|---|---|---|
| 98 | (benzodioxole) | C | 0.850 | 1.06 | 368 |
| 99 | (benzodioxine) | E | 0.08 | 1.04 | 382 |
| 100 | (4-(2-hydroxyethoxy)phenyl) | D | 0.850 | 0.95 | 384 |
| 101 | (2-chloro-4-(2-hydroxyethoxy)phenyl) | D | 0.638 | 1.01 | 418 |

Example 98

$^1$H NMR (CDCl$_3$): δ 7.68 (s, 1H), 7.53-7.35 (m, 5H), 7.14-7.10 (m, 2H), 6.92-6.88 (m, 1H), 6.05 (s, 2H), 2.60 (s, 6H).

Example 99

$^1$H NMR (CDCl$_3$): δ 7.65 (s, 1H), 7.54-7.35 (m, 5H), 7.15-7.09 (m, 2H), 6.94 (d, J=8.2 Hz, 1H), 4.35-4.29 (m, 4H), 2.58 (s, 6H).

Example 100

$^1$H NMR (CDCl$_3$): δ 7.74 (s, 1H), 7.58-7.35 (m, 7H), 7.04-6.99 (m, 2H), 4.17-4.13 (m, 2H), 4.03-3.98 (m, 2H), 2.62 (s, 6H), 2.00 (s br, 1H).

Example 102 and 103

Starting from Scaffold 18, the following examples are prepared:

| Ex-ample | R | Meth-od | Scale (mmol) | LC-MS $t_R$ | [M + 1]$^{++}$ |
|---|---|---|---|---|---|
| 102 | 4-(2-hydroxyethoxy)phenyl | D | 0.681 | 0.89 | 369 |
| 103 | 3-chloro-4-(2-hydroxyethoxy)phenyl | D | 1.815 | 0.96 | 403 |

Example 103

$^1$H NMR (CDCl$_3$): δ 7.67 (s, 1H), 7.62 (d, J=2.3 Hz, 1H), 7.54-7.33 (m, 6H), 7.04 (d, J=8.8 Hz, 1H), 4.25-4.20 (m, 2H), 4.09-4.02 (m, 2H), 3.49 (q, J=7.0 Hz, 2H), 2.16 (s br, 1H), 1.25 (t, J=7.0 Hz, 3H).

Example 104 to 108

Starting from Scaffold 19, the following examples are prepared:

| Ex-ample | R | Meth-od | Scale (mmol) | LC-MS $t_R$ | [M + 1]$^{++}$ |
|---|---|---|---|---|---|
| 104 | benzo[1,3]dioxol-5-yl | E | 0.200 | 1.05 | 367 |
| 105 | 2,3-dihydro-benzo[1,4]dioxin-6-yl | E | 0.200 | 1.05 | 381 |
| 106 | 4-(dimethylamino)phenyl | E | 0.200 | 0.98 | 366 |
| 107 | 4-(2-hydroxyethoxy)phenyl | D | 0.200 | 0.92 | 383 |
| 108 | 3-chloro-4-(2-hydroxyethoxy)phenyl | D | 0.640 | 1.00 | 417 |

Example 109 and 110

Starting from Scaffold 20, the following examples are prepared:

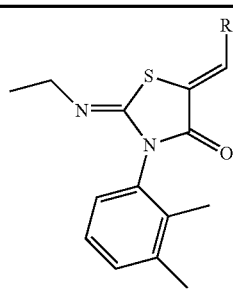
| Example | R | Method | Scale (mmol) | LC-MS $t_R$ | [M+1]++ |
|---|---|---|---|---|---|
| 109 | 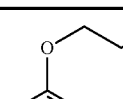 | D | 0.604 | 0.94 | 397 |
| 110 | 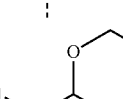 | D | 0.604 | 1.02 | 431 |
Example 110
$^1$H NMR (CDCl$_3$): δ 7.67 (s, 1H), 7.63 (d, J=2.3 Hz, 1H), 7.46 (dd, J=2.3, 8.8 Hz, 1H), 7.25-7.19 (m, 2H), 7.07-7.01 (m, 2H), 4.25-4.20 (m, 2H), 4.08-4.02 (m, 2H), 3.55-3.43 (m, 2H), 2.35 (s, 3H), 2.15 (s br, 1H), 2.07 (s, 3H), 1.25-1.19 (m, 3H).
Example 111 and 112
Starting from Scaffold 21, the following examples are prepared:
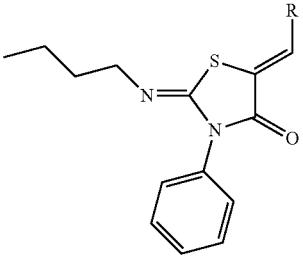
| Example | R | Method | Scale (mmol) | LC-MS $t_R$ | [M+1]++ |
|---|---|---|---|---|---|
| 111 | 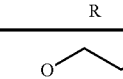 | D | 0.604 | 0.98 | 397 |
| 112 | 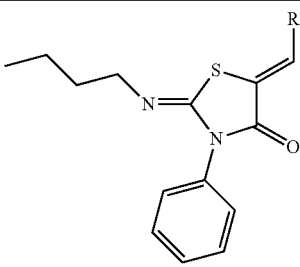 | D | 0.604 | 1.05 | 431 |
Example 113 and 114
Starting from Scaffold 22, the following examples are prepared:
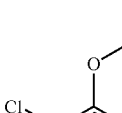
| Example | R | Method | Scale (mmol) | LC-MS $t_R$ | [M+1]++ |
|---|---|---|---|---|---|
| 113 | 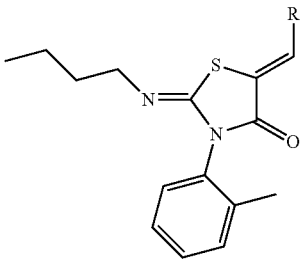 | D | 0.572 | 1.01 | 411 |
| 114 | 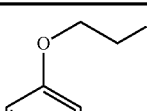 | D | 0.572 | 1.07 | 445 |

Example 114

$^1$H NMR (CDCl$_3$): δ 7.67 (s, 1H), 7.62 (d, J=2.3 Hz, 1H), 7.46 (dd, J=2.3, 8.2 Hz, 1H), 7.39-7.29 (m, 3H), 7.20-7.16 (m, 1H), 7.05 (d, J=8.8 Hz, 1H), 4.25-4.20 (m, 2H), 4.07-7.02 (m, 2H), 3.51-3.35 (m, 2H), 2.20 (s, 3H), 2.14 (s br, 1H), 1.65-1.55 (m, 2H), 1.43-4.30 (m, 2H), 0.93 (t, J=7.3 Hz, 3H).

Example 115 and 116

Starting from Scaffold 23, the following examples are prepared:

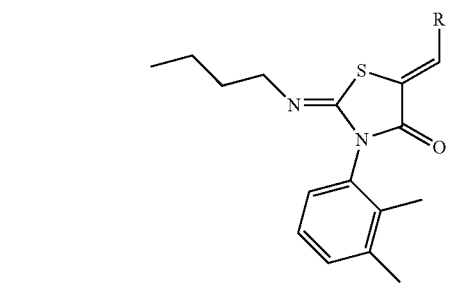

| Example | R | Method | Scale (mmol) | LC-MS $t_R$ | [M + 1]$^{++}$ |
|---|---|---|---|---|---|
| 115 | | D | 0.543 | 1.03 | 425 |
| 116 | | D | 0.543 | 1.09 | 459 |

Examples 117 to 120

Starting from Scaffold 24, the following examples are prepared:

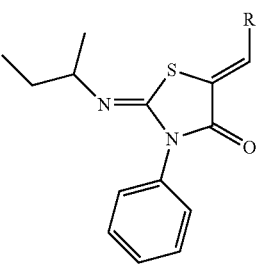

| Example | R | Method | Scale (mmol) | LC-MS $t_R$ | [M + 1]$^{++}$ |
|---|---|---|---|---|---|
| 117 | benzodioxole | E | 0.200 | 1.12 | 381 |
| 118 | benzodioxine | E | 0.200 | 1.10 | 395 |
| 119 | 4-(dimethylamino)phenyl | E | 0.200 | 1.02 | 380 |
| 120 | 2-chloro-4-(2-hydroxyethoxy)phenyl | D | 0.604 | 1.04 | 431 |

Example 120

$^1$H NMR (CDCl$_3$): δ 7.65 (s, 1H), 7.61 (d, J=2.3 Hz, 1H), 7.51-7.32 (m, 6H), 7.03 (d, J=8.2 Hz, 1H), 4.24-4.20 (m, 2H), 4.06-4.01 (m, 2H), 3.32 (hex, J=6.4 Hz, 1H), 2.15 (s br, 1H), 1.60-1.49 (m, 2H), 1.17 (d, J=6.4 Hz, 3H), 0.87 (t, J=7.3 Hz, 3H).

Examples 121 to 123

Starting from Scaffold 25, the following examples are prepared:

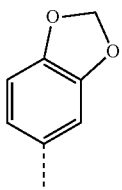

| Example | R | Method | Scale (mmol) | LC-MS $t_R$ | $[M + 1]^{++}$ |
|---|---|---|---|---|---|
| 121 |  | E | 0.200 | 1.08 | 365 |
| 122 | 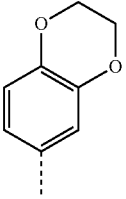 | E | 0.200 | 1.08 | 379 |
| 123 | 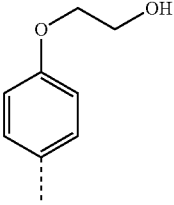 | D | 0.200 | 0.96 | 381 |

Examples 124 and 125

Starting from Scaffold 26, the following examples are prepared:

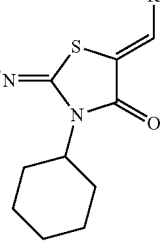

| Example | R | Method | Scale (mmol) | LC-MS $t_R$ | $[M + 1]^{++}$ |
|---|---|---|---|---|---|
| 124 |  | D | 0.283 | 1.08 | 389 |
| 125 |  | D | 0.283 | 1.14 | 423 |

Example 124

$^1$H NMR (CDCl$_3$): δ 7.60 (s, 1H), 7.51-7.46 (m, 2H), 7.01-6.96 (m, 2H), 4.49 (tt, J=3.5, 11.8 Hz, 1H), 4.16-4.11 (m, 2H), 4.02-3.96 (m, 2H), 3.51 (hept, J=6.4 Hz, 1H), 2.50-2.35 (m, 2H), 1.99 (s br, 1H), 1.90-1.80 (m, 2H), 1.70-1.35 (m, 6H), 1.25 (d, J=6.4 Hz, 6H).

Example 126 to 131

Starting from Scaffold 27, the following examples are prepared:

| Example | R | Method | Scale (mmol) | LC-MS $t_R$ | $[M + 1]^{++}$ |
|---|---|---|---|---|---|
| 126 |  | E | 0.200 | 1.12 | 333 |

Example 131

¹H NMR (CDCl₃): δ 7.55 (d, J=2.3 Hz, 1H), 7.52 (s, 1H), 7.40 (dd, J=2.3, 8.2 Hz, 1H), 7.00 (d, J=8.2 Hz, 1H), 4.91 (hept, J=7.0 Hz, 1H), 4.25-4.14 (m, 3H), 3.94-3.81 (m, 2H), 3.53 (hept, J=6.4 Hz, 1H), 2.72 (s br, 1H), 2.09 (s br, 1H), 1.50 (d, J=7.0 Hz, 6H), 1.26 (d, J=6.4 Hz, 6H).

Example 132 to 134

Starting from Scaffold 28, the following examples are prepared:

| Example | R | Method | Scale (mmol) | $t_R$ | $[M+1]^{++}$ |
|---|---|---|---|---|---|
| 127 | 2,3-dihydro-1,4-benzodioxin-6-yl | E | 0.200 | 1.12 | 347 |
| 128 | 4-(dimethylamino)phenyl | E | 0.200 | 1.07 | 332 |
| 129 | 4-(2-hydroxyethoxy)phenyl | D | 0.200 | 0.95 | 345 |
| 130 | 3-chloro-4-(2-hydroxyethoxy)phenyl | D | 0.499 | 1.07 | 383 |
| 131 | 3-chloro-4-(2,3-dihydroxypropoxy)phenyl | D | 0.750 | 0.99 | 413 |
| 132 | 2,3-dihydro-1,4-benzodioxin-6-yl | E | 0.200 | 1.11 | 409 |
| 133 | 4-(dimethylamino)phenyl | E | 0.200 | 1.06 | 394 |
| 134 | 3-chloro-4-(2-hydroxyethoxy)phenyl | D | 0.572 | 1.07 | 445 |

Examples 135 and 136

Starting from Scaffold 29, the following examples are prepared:

|  | | | Scale | LC-MS | |
|---|---|---|---|---|---|
| Example | R | Method | (mmol) | $t_R$ | $[M+1]^{++}$ |
| 135 | [1,3-benzodioxole] | E | 0.160 | 1.14 | 421 |
| 136 | [2,3-dihydro-1,4-benzodioxine] | E | 0.160 | 1.14 | 435 |

Examples 137 and 139

Starting from Scaffold 30, the following examples are prepared:

|  | | | Scale | LC-MS | |
|---|---|---|---|---|---|
| Example | R | Method | (mmol) | $t_R$ | $[M+1]^{++}$ |
| 137 | [1,3-benzodioxole] | E | 0.200 | 1.14 | 415 |
| 138 | [2,3-dihydro-1,4-benzodioxine] | E | 0.200 | 1.15 | 429 |
| 139 | [N,N-dimethylaniline] | E | 0.200 | 1.12 | 414 |

Example 140 to 142

Starting from Scaffold 31, the following examples are prepared:

|  | | | Scale | LC-MS | |
|---|---|---|---|---|---|
| Example | R | Method | (mmol) | $t_R$ | $[M+1]^{++}$ |
| 140 | [1,3-benzodioxole] | E | 0.200 | 1.14 | 415 |
| 141 | [2,3-dihydro-1,4-benzodioxine] | E | 0.200 | 1.15 | 429 |
| 142 | [N,N-dimethylaniline] | E | 0.200 | 1.10 | 414 |

Example 143 to 145

Starting from Scaffold 32, the following examples are prepared:

[Structure: isopropyl-N=C thiazolidinone scaffold with N-phenyl(3-CF3) and =CH-R substituent]

| Example | R | Method | Scale (mmol) | LC-MS $t_R$ | $[M + 1]^{++}$ |
|---|---|---|---|---|---|
| 143 | benzo[1,3]dioxol-5-yl | E | 0.200 | 1.14 | 435 |
| 144 | 2,3-dihydrobenzo[1,4]dioxin-6-yl | E | 0.200 | 1.15 | 449 |
| 145 | 4-(dimethylamino)phenyl | E | 0.200 | 1.13 | 434 |

Examples 146 to 148

Starting from Scaffold 33, the following examples are prepared:

[Structure: isopropyl-N=C thiazolidinone scaffold with N-phenyl(3-Cl) and =CH-R substituent]

| Example | R | Method | Scale (mmol) | LC-MS $t_R$ | $[M + 1]^{++}$ |
|---|---|---|---|---|---|
| 146 | benzo[1,3]dioxol-5-yl | E | 0.200 | 1.12 | 401 |
| 147 | 2,3-dihydrobenzo[1,4]dioxin-6-yl | E | 0.200 | 1.12 | 415 |
| 148 | 4-(dimethylamino)phenyl | E | 0.200 | 1.09 | 400 |

Examples 149 and 150

Starting from Scaffold 34, the following examples are prepared:

87

[Structure: allyl-imino thiazolidinone with N-phenyl and =CH-R substituent]

| Example | R | Method | Scale (mmol) | LC-MS $t_R$ | [M + 1]++ |
|---|---|---|---|---|---|
| 149 | 4-(2-hydroxyethoxy)phenyl | D | 0.650 | 0.95 | 381 |
| 150 | 2-chloro-4-(2-hydroxyethoxy)phenyl | D | 0.650 | 1.01 | 415 |

Example 150

$^1$H NMR (CDCl$_3$): δ 7.69 (s, 1H), 7.62 (d, J=2.3 Hz, 1H), 7.55-7.34 (m, 4H), 7.05 (d, J=8.2 Hz, 1H), 6.01-5.88 (m, 1H), 5.25-5.10 (m, 2H), 4.26-4.20 (m, 2H), 4.12-4.08 (m, 2H), 4.07-4.02 (m, 2H).

Examples 151 to 155

Starting from Scaffold 35, the following examples are prepared:

88

[Structure: allyl-imino thiazolidinone with N-allyl and =CH-R substituent]

| Example | R | Method | Scale (mmol) | LC-MS $t_R$ | [M + 1]++ |
|---|---|---|---|---|---|
| 151 | benzo[1,3]dioxol-5-yl | E | 0.200 | 1.06 | 329 |
| 152 | 2,3-dihydrobenzo[1,4]dioxin-6-yl | E | 0.200 | 1.07 | 343 |
| 153 | 4-(dimethylamino)phenyl | E | 0.200 | 1.05 | 328 |
| 154 | 4-(2-hydroxyethoxy)phenyl | D | 0.200 | 0.95 | 345 |
| 155 | 2-chloro-4-(2-hydroxyethoxy)phenyl | D | 0.764 | 1.01 | 379 |

Example 155

$^1$H NMR (CDCl$_3$): δ 7.62 (s, 1H), 7.57 (d, J=2.3 Hz, 1H), 7.41 (dd, J=2.3, 8.2 Hz, 1H), 7.02 (d, J=8.2 Hz, 1H), 6.06-5.85

(m, 2H), 5.33-5.15 (m, 4H), 4.55-4.50 (m, 2H), 4.24-4.19 (m, 2H), 4.10-4.08 (m, 2H), 4.07-4.01 (m, 2H), 2.13 (s br, 1H).

Example 156

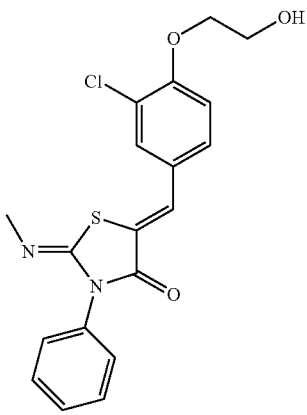 [SMILES: C/N=C1\S/C(=C\c2ccc(OCCO)c(Cl)c2)C(=O)N1c1ccccc1]

5-[3-Chloro-4-(2-hydroxy-ethoxy)-benz-(Z)-ylidene]-2-[(Z)-methylimino]-3-phenyl-thiazolidin-4-one is obtained as an off-white powder starting from Scaffold 36 (150 mg, 0.727 mmol) and 3-chloro-4-(2-acetoxy-ethoxy)-benzaldehyde (353 mg, 1.45 mmol) following Method D. LC-MS: $t_R$=0.91 min, [M+1]$^+$=389. $^1$H NMR (CDCl$_3$): δ 7.69 (s, 1H), 7.63 (d, J=2.3 Hz, 1H), 7.55-7.40 (m, 4H), 7.35-7.30 (m, 2H), 7.05 (d, J=8.2 Hz, 1H), 4.25-4.20 (m, 2H), 4.08-4.00 (m, 2H), 3.27 (s, 3H).

Example 157

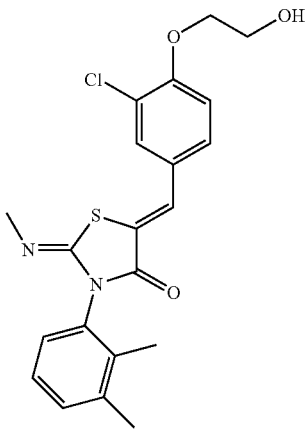 [SMILES: C/N=C1\S/C(=C\c2ccc(OCCO)c(Cl)c2)C(=O)N1c1cccc(C)c1C]

5-[3-Chloro-4-(2-hydroxy-ethoxy)-benz-(Z)-ylidene]-2-[(Z)-methylimino]-3-(2,3-dimethylphenyl)-thiazolidin-4-one is obtained as a pale yellow powder starting from Scaffold 37 (150 mg, 0.640 mmol) and 3-chloro-4-(2-acetoxy-ethoxy)-benzaldehyde (311 mg, 1.28 mmol) following Method D. LC-MS: $t_R$=0.97 min, [M+1]$^+$=417. $^1$H NMR (CDCl$_3$): δ 7.69 (s, 1H), 7.64 (d, J=2.3 Hz, 1H), 7.47 (dd, J=2.3, 8.8 Hz, 1H), 7.25-7.20 (m, 2H), 7.06-7.01 (m, 2H), 4.25-4.20 (m, 2H), 4.07-4.02 (m, 2H), 3.25 (s, 3H), 2.35 (s, 3H), 2.07 (s, 3H).

The invention claimed is:

1. A method for reducing the number of circulating lymphocytes in an animal comprising administering an effective amount of a pharmaceutical composition containing at least one thiazolidin-4-one derivative of the General Formula (II)

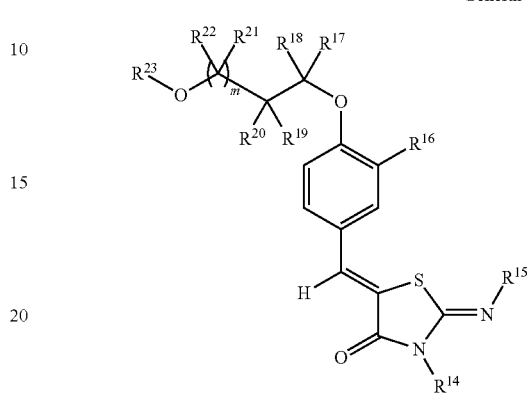

General Formula (II)

wherein:
$R^{14}$ represents lower alkyl; lower alkenyl; cycloalkyl; 5,6,7,8-tetrahydronaphth-1-yl; 5,6,7,8-tetrahydronaphth-2-yl; a phenyl group; or a phenyl group mono-, di- or tri-substituted independently with lower alkyl, halogen, lower alkoxy, or —CF$_3$;
$R^{15}$ represents lower alkyl; allyl; cyclopropyl; cyclobutyl; cyclopentyl; or mono- or di-lower alkylamino;
$R^{16}$ represents hydrogen; hydroxy; lower alkoxy; lower alkyl; or halogen;
$R^{17}$ represents hydrogen, lower alkyl, or hydroxymethyl;
$R^{18}$, $R^{19}$, $R^{21}$ and $R^{22}$ each represents independently hydrogen or methyl;
$R^{20}$ represents hydrogen or lower alkyl; and in case m represents the integer 1, $R^{20}$ in addition represents lower alkoxy, hydroxy, —NH$_2$, —NHR$^5$ or —NR$^5$R$^6$, wherein R$^5$ and R$^6$ each represents independently lower alkyl;
$R^{23}$ represents hydrogen; lower alkyl; hydroxycarbonyl-lower alkyl; 1-glyceryl; or 2-glyceryl;
m represents the integer 0 or 1,
in free or pharmaceutically acceptable salt form.

2. The method according to claim 1, wherein said thiazolidin-4-one derivative is the (Z,Z) isomer.

3. The method according to claim 1, wherein $R^{14}$ represents an unsubstituted, or a mono- or di-substituted phenyl group.

4. The method according to claim 1, wherein $R^{14}$ represents an unsubstituted, or a mono- or di-substituted phenyl group, substituted with methyl or halogen.

5. The method according to claim 1, wherein $R^{15}$ represents lower alkyl.

6. The method according to claim 1, wherein $R^{16}$ represents halogen or methyl.

7. The method according to claim 1, wherein m represents the integer 0, and $R^{17}$, $R^{18}$, $R^{19}$ and $R^{20}$ represent hydrogen.

8. The method according to claim 1, wherein m represents the integer 1, $R^{17}$, $R^{18}$, $R^{19}$, $R^{21}$ and $R^{22}$ represent hydrogen, and $R^{20}$ represents hydroxy.

9. The method according to claim 1, wherein $R^{23}$ represents hydrogen.

10. The method according to claim 1, wherein m represents the integer 0, and $R^{17}$, $R^{18}$, $R^{19}$, $R^{20}$ and $R^{23}$ represent hydrogen.

11. The method according to claim 1, wherein m represents the integer 1, $R^{17}$, $R^{18}$, $R^{19}$, $R^{21}$, $R^{22}$ and $R^{23}$ represent hydrogen, and $R^{20}$ represents hydroxy.

12. The method according to claim 1, wherein $R^{14}$ represents an unsubstituted, or a mono- or di-substituted phenyl group, substituted with methyl or halogen, and $R^{15}$ represents lower alkyl.

13. The method according to claim 1, wherein $R^{14}$ represents an unsubstituted, or a mono- or di-substituted phenyl group, substituted with methyl or halogen, m represents the integer 0, and $R^{17}$, $R^{18}$, $R^{19}$, $R^{20}$ and $R^{23}$ represent hydrogen.

14. The method according to claim 1, wherein $R^{14}$ represents an unsubstituted, or a mono- or di-substituted phenyl group, substituted with methyl or halogen, m represents the integer 1, $R^{17}$, $R^{18}$, $R^{19}$, $R^{21}$, $R^{22}$ and $R^{23}$ represent hydrogen, and $R^{20}$ represents hydroxy.

15. The method according to claim 1, wherein $R^{14}$ represents an unsubstituted, or a mono- or di-substituted phenyl group, substituted with methyl or halogen, $R^{15}$ represents lower alkyl, $R^{16}$ represents methyl or halogen, m represents the integer 0, and $R^{17}$, $R^{18}$, $R^{19}$, $R^{20}$ and $R^{23}$ each represent hydrogen.

16. The method according to claim 1, wherein $R^{14}$ represents an unsubstituted, or a mono- or di-substituted phenyl group, substituted with methyl or halogen, $R^{15}$ represents lower alkyl, $R^{16}$ represents methyl or halogen, m represents the integer 1, $R^{17}$, $R^{18}$, $R^{19}$, $R^{21}$ $R^{22}$ and $R^{23}$ represent hydrogen, and $R^{20}$ represents hydroxy.

17. The method according to claim 1, wherein the thiazolidin-4-one derivative is selected from the group consisting of:

5-[4-(2-hydroxy-ethoxy)-benz[Z]ylidene]-2-([Z]-isopropylimino)-3-phenyl-thiazolidin-4-one,
{2-[4-(2-([Z]-isopropylimino)-4-oxo-3-phenyl-thiazolidin-[Z]-ylidenemethyl)-phenoxy]-ethoxy}-acetic acid,
5-{4-[2-(2,3-dihydroxy-propoxy)-ethoxy]-benz[Z]ylidene}-2-([Z]-isopropylimino)-3-phenyl-thiazolidin-4-one,
5-[3-chloro-4-(2-hydroxy-ethoxy)-benz[Z]ylidene]-2-([Z]-isopropylimino)-3-phenyl-thiazolidin-4-one,
5-[3-fluoro-4-(2-hydroxy-ethoxy)-benz[Z]ylidene]-2-([Z]-isopropylimino)-3-phenyl-thiazolidin-4-one,
5-[4-(2-hydroxy-ethoxy)-3-methyl-benz[Z]ylidene]-2-([Z]-isopropylimino)-3-phenyl-thiazolidin-4-one,
5-[4-(2-hydroxy-ethoxy)-3-methoxy-benz[Z]ylidene]-2-([Z]-isopropylimino)-3-phenyl-thiazolidin-4-one,
5-[4-(3-hydroxy-propoxy)-benz[Z]ylidene]-2-([Z]-isopropylimino)-3-phenyl-thiazolidin-4-one,
5-[4-(2,3-dihydroxy-propoxy)-benz[Z]ylidene]-2-([Z]-isopropylimino)-3-phenyl-thiazolidin-4-one,
5-[3-chloro-4-(2,3-dihydroxy-propoxy)-benz[Z]ylidene]-2-([Z]-isopropylimino)-3-phenyl-thiazolidin-4-one,
5-[4-(2-hydroxy-ethoxy)-benz[Z]ylidene]-2-([Z]-isopropylimino)-3-o-tolyl-thiazolidin-4-one,
5-{4-[2-(2,3-dihydroxy-propoxy)-ethoxy]-benz[Z]ylidene}-2-([Z]-isopropylimino)-3-o-tolyl-thiazolidin-4-one,
5-[3-chloro-4-(2-hydroxy-ethoxy)-benz[Z]ylidene]-2-([Z]-isopropylimino)-3-o-tolyl-thiazolidin-4-one,
5-[4-(2-hydroxy-ethoxy)-3-methoxy-benz[Z]ylidene]-2-([Z]-isopropylimino)-3-o-tolyl-thiazolidin-4-one,
5-[4-(3-hydroxy-propoxy)-benz[Z]ylidene]-2-([Z]-isopropylimino)-3-o-tolyl-thiazolidin-4-one,
5-[3-chloro-4-(2,3-dihydroxy-propoxy)-benz[Z]ylidene]-2-([Z]-isopropylimino)-3-o-tolyl-thiazolidin-4-one,
5-[4-(2-hydroxy-ethoxy)-benz[Z]ylidene]-2-([Z]-isopropylimino)-3-m-tolyl-thiazolidin-4-one,
5-[3-chloro-4-(2-hydroxy-ethoxy)-benz[Z]ylidene]-2-([Z]-isopropylimino)-3-m-tolyl-thiazolidin-4-one,
5-[3-chloro-4-(2,3-dihydroxy-propoxy)-benz[Z]ylidene]-2-([Z]-isopropylimino)-3-m-tolyl-thiazolidin-4-one,
5-[4-(2-hydroxy-ethoxy)-benz[Z]ylidene]-2-([Z]-isopropylimino)-3-p-tolyl-thiazolidin-4-one,
5-[3-chloro-4-(2-hydroxy-ethoxy)-benz[Z]ylidene]-2-([Z]-isopropylimino)-3-p-tolyl-thiazolidin-4-one,
5-[3-chloro-4-(2,3-dihydroxy-propoxy)-benz[Z]ylidene]-2-([Z]-isopropylimino)-3-p-tolyl-thiazolidin-4-one,
3-(2,3-dimethyl-phenyl)-5-[4-(2-hydroxy-ethoxy)-benz[Z]ylidene]-2-([Z]-isopropylimino)-thiazolidin-4-one,
5-{4-[2-(2,3-dihydroxy-propoxy)-ethoxy]-benz[Z]ylidene}-3-(2,3-dimethyl-phenyl)-2-([Z]-isopropylimino)-thiazolidin-4-one,
5-[3-chloro-4-(2-hydroxy-ethoxy)-benz[Z]ylidene]-3-(2,3-dimethyl-phenyl)-2-([Z]-isopropylimino)-thiazolidin-4-one,
3-(2,3-dimethyl-phenyl)-5-[3-fluoro-4-(2-hydroxy-ethoxy)-benz[Z]ylidene]-2-([Z]-isopropylimino)-thiazolidin-4-one,
3-(2,3-dimethyl-phenyl)-5-[4-(2-hydroxy-ethoxy)-3-methyl-benz[Z]ylidene]-2-([Z]-isopropylimino)-thiazolidin-4-one,
3-(2,3-dimethyl-phenyl)-5-[4-(2-hydroxy-ethoxy)-3-methoxy-benz[Z]ylidene]-2-([Z]-isopropylimino)-thiazolidin-4-one,
5-[3-chloro-4-(2,3-dihydroxy-propoxy)-benz[Z]ylidene]-3-(2,3-dimethyl-phenyl)-2-([Z]-isopropylimino)-thiazolidin-4-one,
3-(2,4-dimethyl-phenyl)-5-[4-(2-hydroxy-ethoxy)-benz[Z]ylidene]-2-([Z]-isopropylimino)-thiazolidin-4-one,
3-(2,6-dimethyl-phenyl)-5-[4-(2-hydroxy-ethoxy)-benz[Z]ylidene]-2-([Z]-isopropylimino)-thiazolidin-4-one,
3-(2-chloro-phenyl)-5-[4-(2-hydroxy-ethoxy)-benz[Z]ylidene]-2-([Z]-isopropylimino)-thiazolidin-4-one,
5-[3-chloro-4-(2-hydroxy-ethoxy)-benz[Z]ylidene]-3-(2-chloro-phenyl)-2-([Z]-isopropylimino)-thiazolidin-4-one,
5-[3-chloro-4-(2,3-dihydroxy-propoxy)-benz[Z]ylidene]-3-(2-chloro-phenyl)-2-([Z]-isopropylimino)-thiazolidin-4-one,
5-[4-(2-hydroxy-ethoxy)-benz[Z]ylidene]-2-([Z]-isopropylimino)-3-(2-methoxy-phenyl)-thiazolidin-4-one,
5-[3-chloro-4-(2-hydroxy-ethoxy)-benz[Z]ylidene]-2-([Z]-isopropylimino)-3-(2-methoxy-phenyl)-thiazolidin-4-one,
5-[4-(2-hydroxy-ethoxy)-benz[Z]ylidene]-2-([Z]-isopropylimino)-3-(4-methoxy-phenyl)-thiazolidin-4-one,
5-[3-chloro-4-(2-hydroxy-ethoxy)-benz[Z]ylidene]-2-([Z]-isopropylimino)-3-(4-methoxy-phenyl)-thiazolidin-4-one,
3-allyl-5-[4-(2-hydroxy-ethoxy)-benz[Z]ylidene]-2-([Z]-isopropylimino)-thiazolidin-4-one,
3-allyl-5-[3-chloro-4-(2-hydroxy-ethoxy)-benz[Z]ylidene]-2-([Z]-isopropylimino)-thiazolidin-4-one,
3-allyl-5-[3-chloro-4-(2,3-dihydroxy-propoxy)-benz[Z]ylidene]-2-([Z]-isopropylimino)-thiazolidin-4-one,
5-[4-(2-hydroxy-ethoxy)-benz[Z]ylidene]-3-phenyl-2-([Z]-propylimino)-thiazolidin-4-one,
5-[3-chloro-4-(2-hydroxy-ethoxy)-benz[Z]ylidene]-3-phenyl-2-([Z]-propylimino)-thiazolidin-4-one,
5-[4-(2-hydroxy-ethoxy)-3-methyl-benz[Z]ylidene]-3-phenyl-2-([Z]-propylimino)-thiazolidin-4-one,
5-[3-chloro-4-(2,3-dihydroxy-propoxy)-benz[Z]ylidene]-3-phenyl-2-([Z]-propylimino)-thiazolidin-4-one, 5-[4-(2-hydroxy-ethoxy)-benz[Z]ylidene]-2-([Z]-propylimino)-3-o-tolyl-thiazolidin-4-one,
5-[4-(3-hydroxy-propoxy)-benz[Z]ylidene]-2-([Z]-propylimino)-3-o-tolyl-thiazolidin-4-one,
5-[3-chloro-4-(2-hydroxy-ethoxy)-benz[Z]ylidene]-2-([Z]-propylimino)-3-o-tolyl-thiazolidin-4-one,
5-[4-(2-hydroxy-ethoxy)-3-methyl-benz[Z]ylidene]-2-([Z]-propylimino)-3-o-tolyl-thiazolidin-4-one,
5-[3-chloro-4-(2,3-dihydroxy-propoxy)-benz[Z]ylidene]-2-([Z]-propylimino)-3-o-tolyl-thiazolidin-4-one,
(R)-5-[3-chloro-4-(2,3-dihydroxy-propoxy)-benz[Z]ylidene]-2-([Z]-propylimino)-3-o-tolyl-thiazolidin-4-one,
(S)-5-[3-chloro-4-(2,3-dihydroxy-propoxy)-benz[Z]ylidene]-2-([Z]-propylimino)-3-o-tolyl-thiazolidin-4-one,
3-(2,3-dimethyl-phenyl)-5-[4-(2-hydroxy-ethoxy)-benz[Z]ylidene]-2-([Z]-propylimino)-thiazolidin-4-one,
5-{4-[2-(2,3-dihydroxy-propoxy)-ethoxy]-benz[Z]ylidene}-3-(2,3-dimethyl-phenyl)-2-([Z]-propylimino)-thiazolidin-4-one,
5-[3-chloro-4-(2-hydroxy-ethoxy)-benz[Z]ylidene]-3-(2,3-dimethyl-phenyl)-2-([Z]-propylimino)-thiazolidin-4-one,
3-(2,3-dimethyl-phenyl)-5-[4-(2-hydroxy-ethoxy)-3-methyl-benz[Z]ylidene]-2-([Z]-propylimino)-thiazolidin-4-one,
3-(2,3-dimethyl-phenyl)-5-[4-(2-hydroxy-ethoxy)-3-methoxy-benz[Z]ylidene]-2-([Z]-propylimino)-thiazolidin-4-one,
5-[4-(2,3-dihydroxy-propoxy)-benz[Z]ylidene]-3-(2,3-dimethyl-phenyl)-2-([Z]-propylimino)-thiazolidin-4-one,
5-[3-chloro-4-(2,3-dihydroxy-propoxy)-benz[Z]ylidene]-3-(2,3-dimethyl-phenyl)-2-([Z]-propylimino)-thiazolidin-4-one,
2-([Z]-tert-butylimino)-5-[3-chloro-4-(2-hydroxy-ethoxy)-benz[Z]ylidene]-3-phenyl-thiazolidin-4-one,
2-(dimethyl-hydrazono)-5-[4-(2-hydroxy-ethoxy)-benz[Z]ylidene]-3-phenyl-thiazolidin-4-one,
5-[3-chloro-4-(2-hydroxy-ethoxy)-benz[Z]ylidene]-2-(dimethyl-hydrazono)-3-phenyl-thiazolidin-4-one,
2-([Z]-ethylimino)-5-[4-(2-hydroxy-ethoxy)-benz[Z]ylidene]-3-phenyl-thiazolidin-4-one,
5-[3-chloro-4-(2-hydroxy-ethoxy)-benz[Z]ylidene]-2-([Z]-ethylimino)-3-phenyl-thiazolidin-4-one,
2-([Z]-ethylimino)-5-[4-(2-hydroxy-ethoxy)-benz[Z]ylidene]-3-o-tolyl-thiazolidin-4-one,
5-[3-chloro-4-(2-hydroxy-ethoxy)-benz[Z]ylidene]-2-([Z]-ethylimino)-3-o-tolyl-thiazolidin-4-one,
3-(2,3-dimethyl-phenyl)-2-([Z]-ethylimino)-5-[4-(2-hydroxy-ethoxy)-benz[Z]ylidene]-thiazolidin-4-one,
5-[3-chloro-4-(2-hydroxy-ethoxy)-benz[Z]ylidene]-3-(2,3-dimethyl-phenyl)-2-([Z]-ethylimino)-thiazolidin-4-one,
2-([Z]-butylimino)-5-[4-(2-hydroxy-ethoxy)-benz[Z]ylidene]-3-phenyl-thiazolidin-4-one,
2-([Z]-butylimino)-5-[3-chloro-4-(2-hydroxy-ethoxy)-benz[Z]ylidene]-3-phenyl-thiazolidin-4-one,
2-([Z]-butylimino)-5-[4-(2-hydroxy-ethoxy)-benz[Z]ylidene]-3-o-tolyl-thiazolidin-4-one,
2-([Z]-butylimino)-5-[3-chloro-4-(2-hydroxy-ethoxy)-benz[Z]ylidene]-3-o-tolyl-thiazolidin-4-one,
2-([Z]-butylimino)-3-(2,3-dimethyl-phenyl)-5-[4-(2-hydroxy-ethoxy)-benz[Z]ylidene]-thiazolidin-4-one,
2-([Z]-butylimino)-5-[3-chloro-4-(2-hydroxy-ethoxy)-benz[Z]ylidene]-3-(2,3-dimethyl-phenyl)-thiazolidin-4-one,
2-([Z]-sec-butylimino)-5-[3-chloro-4-(2-hydroxy-ethoxy)-benz[Z]ylidene]-3-phenyl-thiazolidin-4-one,
2-([Z]-cyclopropylimino)-5-[4-(2-hydroxy-ethoxy)-benz[Z]ylidene]-3-phenyl-thiazolidin-4-one,
3-cyclohexyl-5-[4-(2-hydroxy-ethoxy)-benz[Z]ylidene]-2-([Z]-isopropylimino)-thiazolidin-4-one,
5-[3-chloro-4-(2-hydroxy-ethoxy)-benz[Z]ylidene]-3-cyclohexyl-2-([Z]-isopropylimino)-thiazolidin-4-one,
5-[4-(2-hydroxy-ethoxy)-benz[Z]ylidene]-3-isopropyl-2-([Z]-isopropylimino)-thiazolidin-4-one,
5-[3-chloro-4-(2-hydroxy-ethoxy)-benz[Z]ylidene]-3-isopropyl-2-([Z]-isopropylimino)-thiazolidin-4-one,
5-[3-chloro-4-(2,3-dihydroxy-propoxy)-benz[Z]ylidene]-3-isopropyl-2-([Z]-isopropylimino)-thiazolidin-4-one,
2-([Z]-allylimino)-5-[4-(2-hydroxy-ethoxy)-benz[Z]ylidene]-3-phenyl-thiazolidin-4-one,
2-([Z]-allylimino)-5-[3-chloro-4-(2-hydroxy-ethoxy)-benz[Z]ylidene]-3-phenyl-thiazolidin-4-one,
3-allyl-2-([Z]-allylimino)-5-[4-(2-hydroxy-ethoxy)-benz[Z]ylidene]-thiazolidin-4-one,
3-allyl-2-([Z]-allylimino)-5-[3-chloro-4-(2-hydroxy-ethoxy)-benz[Z]ylidene]-thiazolidin-4-one,
5-[3-chloro-4-(2-hydroxy-ethoxy)-benz[Z]ylidene]-2-([Z]-methylimino)-3-phenyl-thiazolidin-4-one, and
5-[3-chloro-4-(2-hydroxy-ethoxy)-benz[Z]ylidene]-3-(2,3-dimethyl-phenyl)-2-([Z]-methylimino)-thiazolidin-4-one.

18. The method according to claim 1, wherein the thiazolidin-4-one derivative is selected from the group consisting of:

5-[4-(2-hydroxy-ethoxy)-benz[Z]ylidene]-2-([Z]-isopropylimino)-3-phenyl-thiazolidin-4-one,
5-[3-chloro-4-(2-hydroxy-ethoxy)-benz[Z]ylidene]-2-([Z]-isopropylimino)-3-phenyl-thiazolidin-4-one,
5-[3-chloro-4-(2,3-dihydroxy-propoxy)-benz[Z]ylidene]-2-([Z]-isopropylimino)-3-o-tolyl-thiazolidin-4-one,
5-[3-chloro-4-(2-hydroxy-ethoxy)-benz[Z]ylidene]-3-(2,3-dimethyl-phenyl)-2-([Z]-isopropylimino)-thiazolidin-4-one,
5-[3-chloro-4-(2,3-dihydroxy-propoxy)-benz[Z]ylidene]-3-(2,3-dimethyl-phenyl)-2-([Z]-isopropylimino)-thiazolidin-4-one,
5-[3-chloro-4-(2-hydroxy-ethoxy)-benz[Z]ylidene]-3-phenyl-2-([Z]-propylimino)-thiazolidin-4-one,
5-[4-(2-hydroxy-ethoxy)-3-methyl-benz[Z]ylidene]-3-phenyl-2-([Z]-propylimino)-thiazolidin-4-one,
5-[3-chloro-4-(2,3-dihydroxy-propoxy)-benz[Z]ylidene]-3-phenyl-2-([Z]-propylimino)-thiazolidin-4-one,
5-[3-chloro-4-(2,3-dihydroxy-propoxy)-benz[Z]ylidene]-2-([Z]-propylimino)-3-o-tolyl-thiazolidin-4-one,
(R)-5-[3-chloro-4-(2,3-dihydroxy-propoxy)-benz[Z]ylidene]-2-([Z]-propylimino)-3-o-tolyl-thiazolidin-4-one,
(S)-5-[3-chloro-4-(2,3-dihydroxy-propoxy)-benz[Z]ylidene]-2-([Z]-propylimino)-3-o-tolyl-thiazolidin-4-one,
5-[3-chloro-4-(2-hydroxy-ethoxy)-benz[Z]ylidene]-3-(2,3-dimethyl-phenyl)-2-([Z]-propylimino)-thiazolidin-4-one,
5-[3-chloro-4-(2,3-dihydroxy-propoxy)-benz[Z]ylidene]-3-(2,3-dimethyl-phenyl)-2-([Z]-propylimino)-thiazolidin-4-one,
2-(dimethyl-hydrazono)-5-[4-(2-hydroxy-ethoxy)-benz[Z]ylidene]-3-phenyl-thiazolidin-4-one, 5-[3-chloro-4-(2-hydroxy-ethoxy)-benz[Z]ylidene]-2-([Z]-ethylimino)-3-phenyl-thiazolidin-4-one, 5-[3-chloro-4-(2-hydroxy-ethoxy)-benz[Z]ylidene]-3-(2,3-dimethyl-phenyl)-2-([Z]-ethylimino)-thiazolidin-4-one, and 5-[3-chloro-4-(2-hydroxy-ethoxy)-benz[Z]ylidene]-3-isopropyl-2-([Z]-isopropylimino)-thiazolidin-4-one.

19. The method according to claim 1, wherein the thiazolidin-4-one derivative is (R)-5-[3-chloro-4-(2,3-dihydroxy-propoxy)-benz[Z]ylidene]-2-([Z]-propylimino)-3-o-tolyl-thiazolidin-4-one.

20. The method according to claim 19, wherein the lymphocytes are T- and B-lymphocytes.

21. The method according to claim 1, wherein the lymphocytes are T- and B-lymphocytes.

* * * * *